US009551005B2

(12) United States Patent
Piller et al.

(10) Patent No.: US 9,551,005 B2
(45) Date of Patent: Jan. 24, 2017

(54) IMMUNOASSAY FOR DETECTING THYROGLOBULIN UTILIZING SOYBEAN PRODUCED RECOMBINANT THYROGLOBULIN

(76) Inventors: Kenneth John Piller, Davidson, NC (US); Kenneth Lee Bost, Davidson, NC (US)

( * ) Notice: Subject to any disclaimer, the term of this patent is extended or adjusted under 35 U.S.C. 154(b) by 788 days.

(21) Appl. No.: 13/254,704

(22) Filed: Sep. 2, 2011

(65) Prior Publication Data

US 2013/0243821 A1    Sep. 19, 2013

Related U.S. Application Data

(63) Continuation-in-part of application No. PCT/US2010/042248, filed on Jul. 16, 2010.

(60) Provisional application No. 61/379,834, filed on Sep. 3, 2010, provisional application No. 61/226,086, filed on Jul. 16, 2009.

(51) Int. Cl.
*C12N 15/82* (2006.01)
*C07K 14/575* (2006.01)

(52) U.S. Cl.
CPC ......... *C12N 15/8257* (2013.01); *C07K 14/575* (2013.01); *C07K 2319/21* (2013.01)

(58) Field of Classification Search
None
See application file for complete search history.

(56) References Cited

FOREIGN PATENT DOCUMENTS

WO    WO 00/20612    *    4/2000    ............. C12N 15/82

OTHER PUBLICATIONS

Ohwovoriole, A. E. Effectiveness of different methods to eliminate interference by thyroglobulin antibodies in the ELISA for thyroid microsomal autoantibodies. (1989) Asian Pacific Journal of Allergy and Immunology; vol. 7; pp. 79-83.*
Erali et al. ELISA for thyroglobulin in serum: recovery studies to evaluate autoantibody interference and reliability of thyroglobulin values. (1996) Clinical Chemistry; vol. 42; pp. 766-770.*
Ng et al. Enzyme immunoassay for simultaneous measurement of autoantibodies against thyroglobulin and thyroid microsome in serum. (1987) Clinical Chemistry; vol. 33; pp. 2286-2288.*
Tate et al. Interferences in immunoassay. (2004) Clinical Biochem. Rev.; vol. 25; pp. 105-120.*
Malthiery et al. *Homo sapiens* thyroglobulin (TG) mRNA, complete cds. (1999) GenBank Accession U93033; pp. 1-6.*
Schmitt et al. Affinity purification of histidine-tagged proteins. (1993) Molecular Biology Reports; vol. 18; pp. 223-230.*
Bost et al. Soybean-derived thyroglobulin as an analyte specific reagent for in vitro diagnostic tests and deviced. (2014) Chapter 2, in Advances in Medicine and Biology, vol. 80; pp. 23-39.*

Slatosky, J., B. Shipton, and H. Wahba. 2000. Thyroiditis: differential diagnosis and management. Am Fam Physician 61:1047.
Wertheimer, A. I., and T. M. Santella. 2005. The levothyroine spectrum: Bioequivalence and cost considerations. Formulary 40:258.
Vladutiu, A. O., and N. R. Rose. 1975. Cellular basis of the genetic control of immune responsiveness to murine thyroglobulin in mice. Cell Immunol 17:106.
Maron, R., R. Zerubavel, A. Friedman, and I. R. Cohen. 1983. T lymphocyte line specific for thyroglobulin produces or vaccinates against autoimmune thyroiditis in mice. J Immunol 131:2316.
Vali, M., N. R. Rose, and P. Caturegli. 2000. Thyroglobulin as autoantigen: structure-function relationships. Rev Endocr Metab Disord 1:69.
Quaratino, S., E. Badami, Y. Y. Pang, I. Bartok, J. Dyson, D. Kioussis, M. Londei, and L. Maiuri. 2004. Degenerate self-reactive human T-cell receptor causes spontaneous autoimmune disease in mice. Nat Med 10:920.
Summary Statement from grant request Application No. 1 R01 DK081875-01 (2008).
Enewold L, Zhu K, Ron E, Marrogi AJ, Stojadinovic A, Peoples GE, et al. Rising thyroid cancer incidence in the United States by demographic and tumor characteristics, 1980-2005. Cancer Epidemiol Biomarkers Prev. Mar. 2009;18(3):784-91.
Davies L, Welch HG. Increasing incidence of thyroid cancer in the United States, 1973-2002. Jama. May 10, 2006;295(18):2164-7.
Benbassat CA, Mechlis-Frish S, Guttmann H, Glaser B, Krausz Y. Current concepts in the follow-up of patients with differentiated thyroid cancer. Isr Med Assoc J. Jul. 2007;9(7):540-5.
Van de Graaf SA, Ris-Stalpers C, Pauws E, Mendive FM, Targovnik HM, de Vijlder JJ. Up to date with human thyroglobulin. The Journal of endocrinology. Aug. 2001;170(2):307-21.
Venkatesh SG, Deshpande V. A comparative review of the structure and biosynthesis of thyroglobulin. Comparative biochemistry and physiology. Jan. 1999;122(1):13-20.
Feldt-Rasmussen U, Profilis C, Colinet E, Black E, Bornet H, Bourdoux P, et al. Human thyroglobulin reference material (CRM 457). 2nd Part: Physicochemical characterization and certification. Annales de biologie clinique. 1996;54(10-11):343-8.
Jun JY, Manni A. Medical management of persistent or recurrent differentiated thyroid carcinoma. Otolaryngologic clinics of North America. Dec. 2008;41(6):1241-60, xi-xii.
Mazzaferri EL, Robbins RJ, Spencer CA, Braverman LE, Pacini F, Wartofsky L, et al. A consensus report of the role of serum (Continued)

*Primary Examiner* — Cathy Kingdon Worley
(74) *Attorney, Agent, or Firm* — Ben Schroeder Law, PLLC

(57) ABSTRACT

The present invention includes novel soybean derived human thyroglobulin, methods of producing human thyroglobulin in plants such as soybean, and novel diagnostic applications for the detection and stratification of endocrine malignancies including thyroid cancer and thyroiditis. The invention also includes the use of soybean-derived human thyroglobulin in affinity matrices to remove autoreactive anti-thyroglobulin antibodies from patient's sera prior to analyses. Moreover, the invention also includes methods and compositions of treating, preventing and or/ameliorating symptoms associated with thyroiditis.

14 Claims, 22 Drawing Sheets

(56) References Cited

OTHER PUBLICATIONS thyroglobulin as a monitoring method for low-risk patients with papillary thyroid carcinoma. The Journal of clinical endocrinology and metabolism. Apr. 2003;88(4):1433-41.

Whitley RJ, Ain KB. Thyroglobulin: a specific serum marker for the management of thyroid carcinoma. Clinics in laboratory medicine. Mar. 2004;24(1):29-47.

Emerson CH, Torres MS. Recombinant human thyroid-stimulating hormone: pharmacology, clinical applications and potential uses. BioDrugs. 2003;17(1):19-38.

Persoon AC, Jager PL, Sluiter WJ, Plukker JT, Wolffenbuttel BH, Links TP. A sensitive Tg assay or rhTSH stimulated Tg: what's the best in the long-term follow-up of patients with differentiated thyroid carcinoma? PLoS ONE. 2007;2(8): e816.

Wong R, Topliss DJ, Bach LA, Hamblin PS, Kalff V, Long F, et al. Recombinant human thyroid-stimulating hormone (Thyrogen) in thyroid cancer follow up: experience at a single institution. Internal medicine journal. Mar. 2009;39(3):156-63.

The Cancer Diagnostics Market: Emerging Opportunities and Business Expansion Strategies: Venture Planning Group Report; Oct. 2008.

Clark PM. Laboratory services for thyroglobulin and implications for monitoring of differentiated thyroid cancer. Journal of clinical pathology. May 2009;62(5):402-6.

Dufour DR. Thyroglobulin and thyroglobulin antibodies. Thyroid Cancer: A Comprehensive Guide to Clinical Management. 2nd ed. Totowa, NJ: Humana Press, Inc. 2008:297-304.

Krahn J, Dembinski T. Thyroglobulin and anti-thyroglobulin assays in thyroid cancer monitoring. Clinical biochemistry. Mar. 2009;42(4-5):416-9.

Spencer CA, Bergoglio LM, Kazarosyan M, Fatemi S, LoPresti JS. Clinical impact of thyroglobulin (Tg) and Tg autoantibody method differences on the management of patients with differentiated thyroid carcinomas. The Journal of clinical endocrinology and metabolism. Oct. 2005;90(10):5566-75.

Spencer CA, Lopresti JS. Measuring thyroglobulin and thyroglobulin autoantibody in patients with differentiated thyroid cancer. Nature clinical practice. Apr. 2008;4(4):223-33.

Barin JG, Talor MV, Sharma RB, Rose NR, Burek CL. Iodination of murine thyroglobulin enhances autoimmune reactivity in the NOD.H2 mouse. Clinical and experimental immunology. Nov. 2005;142(2):251-9.

Latrofa F, Phillips M, Rapoport B, McLachlan SM. Human monoclonal thyroglobulin autoantibodies: epitopes and immunoglobulin genes. The Journal of clinical endocrinology and metabolism. Oct. 2004;89(10):5116-23.

Hollowell JG, Staehling NW, Flanders WD, Hannon WH, Gunter EW, Spencer CA, et al. Serum TSH, T(4), and thyroid antibodies in the United States population (1988 to 1994): National Health and Nutrition Examination Survey (Nhanes III). The Journal of clinical endocrinology and metabolism. Feb. 2002;87(2):489-99.

Liu K. Soybeans: Chemistry, Technology, and Utilization. Gaithersburg, MD: Aspen Publishers, Inc. 1999.

Traynor PL, Adair, D., Irwin, R. A practical guide to containment: Greenhouse research with transgenic plants and microbes. Blacksburg, VA: Information Systems for Biotechnology 2001.

Garg R, Tolbert M, Oakes JL, Clemente TE, Bost KL, Piller KJ. Chloroplast targeting of FanC, the major antigenic subunit of *Escherichia coli* K99 fimbriae, in transgenic soybean. Plant cell reports. Jul. 2007;26(7):1011-23.

Piller KJ, Clemente TE, Jun SM, Petty CC, Sato S, Pascual DW, et al. Expression and immunogenicity of an *Escherichia coli* K99 fimbriae subunit antigen in soybean. Planta. Sep. 2005;222(1):6-18.

Gagnon P. Monoliths seen to revitalize bioseparations. Genetic Engineering & Biotechnology News. 2006;26(17).

Gagnon P. The emerging generation of chromatography tools for virus purification. BioProcess International. 2008; Oct. 2008 supplement:24-30.

Hage DS. Affinity chromatography: a review of clinical applications. Clinical chemistry. May 1999;45(5):593-615.

Mallik R, Hage DS. Affinity monolith chromatography. Journal of separation science. Aug. 2006;29(12):1686-704.

Paz MM, Martinez JC, Kalvig AB, Fonger TM, and Wang K. Improved cotyledonary node method using an alternative explant derived from mature seed for efficient Agrobacterium-mediated soybean transformation. Plant Cell Rep. 2006; 25: 206-213.

Oakes JL, Bost KL, and Piller KJ Stability of a soybean seed-derived vaccine antigen following long-term storage, processing and transport in the absence of a cold chain. J Sci Food Agric 2009; 89: 2191-2199.

Lee, S., N. Scherberg, and L. J. DeGroot. 1998. Induction of oral tolerance in human autoimmune thyroid disease. Thyroid 8:229-234.

Peterson, K. E., and H. Braley-Mullen. 1995. Suppression of murine experimental autoimmune thyroiditis by oral administration of porcine thyroglobulin. Cellular immunology 166:123-130.

Parish, N. M., D. Rayner, A. Cooke, and I. M. Roitt. 1988. An investigation of the nature of induced suppression to experimental autoimmune thyroiditis. Immunology 63:199-203.

Sanker, A. J., C. R. Clark, and R. S. Sundick. 1985. The induction of tolerance to thyroglobulin significantly reduces the severity of thyroiditis in obese strain chickens. J Immunol 135:281-285.

Guimaraes, V. C., J. Quintans, M. E. Fisfalen, F. H. Straus, P. E. Fields, G. Medeiros-Neto, and L. J. DeGroot. 1996. Immunosuppression of thyroiditis. Endocrinology 137:2199-2207.

Guimaraes, V. C., J. Quintans, M. E. Fisfalen, F. H. Straus, K. Wilhelm, A. Medeiros-Neto, and L. J. DeGroot. 1995. Suppression of development of experimental autoimmune thyroiditis by oral administration of thyroglobulin. Endocrinology 136:3353-3359.

Gardine, C. A., F. Gentile, C. Pellegrini, F. Giallauria, G. Torelli, T. Kouki, and L. DeGroot. 2003. Multiple fragments of human TG are capable of inducing oral tolerance to whole human TG. J Endocrinol Invest 26:294-300.

Rapoport, B., and S. M. McLachlan. 1996. Food for thought—is induction of oral tolerance feasible and practical in human thyroid autoimmunity? Endocrinology 137:2197-2198.

Klein, I., and S. Danzi. 2003. Evaluation of the therapeutic efficacy of different levothyroxine preparations in the treatment of human thyroid disease. Thyroid 13:1127-1132.

Clarke, N., and U. M. Kabadi. 2004. Optimizing treatment of hypothyroidism. Treatments in endocrinology 3:217-221.

Evans, T. C. 2003. Thyroid disease. Prim Care 30:625-640.

Hueston, W. J. 2001. Treatment of hypothyroidism. Am Fam Physician 64:1717-1724.

Roberts, C. G., and P. W. Ladenson. 2004. Hypothyroidism. Lancet 363:793-803.

Dayan, C. M., and G. H. Daniels. 1996. Chronic autoimmune thyroiditis. N Engl J Med 335:99.

Pearce, E. N., A. P. Farwell, and L. E. Braverman. 2003. Thyroiditis. N Engl J Med 348:2646.

Rose, N. R., and I. R. Mackay. 1998. The Autoimmune Diseases. Academic Press, San Diego, CA.

Weetman, A. P. 2003. Autoimmune thyroid disease: propagation and progression. Eur J Endocrinol 148:1.

Diez, J. J., I. Molina, and M. T. Ibars. 2003. Prevalence of thyroid dysfunction in adults over age 60 years from an urban community. Exp Clin Endocrinol Diabetes 111:480.

Flynn, R. W., T. M. MacDonald, A. D. Morris, R. T. Jung, and G. P. Leese. 2004. The thyroid epidemiology, audit, and research study: thyroid dysfunction in the general population. J Clin Endocrinol Metab 89:3879.

Russell et al., Biotechnology and Engineering, 89:7 (2005), 775-782.

Leite et al., Molecular Breeding, 6, (2000), 47-53.

Eva Stoger et al., Current Opinion in Biotechnology, 16, 167-173.

Xia et al., PNAs, 107(32), (2010), 14059-14063.

Rosano et al., Frontiers in Microbiology, 5(172), (2014) 1-17.

Uno et al., Genes to Cells, 16, (2011), 842-856.

Victor et al., Malaria Journal, 9(325), (2010), 1-13.

Chromikova et al., Cytotechnology, 67, (2015), 343-356.

(56) References Cited

OTHER PUBLICATIONS

Verburg et al., Thyroid, 23 (10), 2013, Reviews and Scholarly Dialog, pp. 1211-1225.
Spencer et al., Endocrinology, 21(5), 2014, pp. 394-404.
Spencer et al., Best Practice & Research Clinical Endocrinology & Metabolism, 27, 2013, pp. 701-712.
Tsai et al. ACS Cent Sci. 2, 2016 pp. 139-147.
Netzel et al. J Clin Endocrinol Metab. Aug. 2015; 100(8): E1074-E1083.
Hoofnagle et al. J Clin Endocrinol Metab. Apr. 2013; 98(4): 1343-1352.
White et al. Expert Opin Drug Discov. Apr. 2015; 10(4): 427-439.
Cancer Facts & Figures 2016 American Cancer Society. Cancer Facts & Figures 2016. Atlanta: American Cancer Society; 2016.
Forsight Science and Technology Niche Analysis Jan. 27, 2012.
Bost et al., Advances in Medicine and Biology, vol. 80, Editor Lean V. Berhardt, 2014, "Soybean-Derived Thyroglobulin As an Analyte Specific Reagent for In Vitro Diagnostic Tests and Devices", pp. 23-39.

\* cited by examiner

```
Query   1    ATGGCTCTTGTGCTCGAGATTTTCACCCTTCTCGCTTCTATTTGCTGGGTGTCCGCTAAC   60
             ||||| || || || |||||| |||||||| || || || || |||||||||||| || ||
Sbjct   1    ATGGCCCTGGTCCTGGAGATCTTCACCCTGCTGGCCTCCATCTGCTGGGTGTCGGCCAAT   60

Query   61   ATTTTCGAGTACCAGGTTGACGCTCAACCACTTAGACCATGCGAGCTTCAAAGAGAGACT   120
             || |||||||||||||| || || || || ||| | || || ||||| || || || ||
Sbjct   61   ATCTTCGAGTACCAGGTGGATGCCCAGCCCCTTCGTCCCTGTGAGCTGCAGAGGGAAACG   120

Query   121  GCTTTCCTCAAGCAGGCTGATTATGTTCCACAATGCGCTGAGGATGGATCTTTCCAAACT   180
             || || || ||||| || || || || || || || || |||||||||    ||||| |||
Sbjct   121  GCCTTTCTGAAGCAAGCAGACTACGTGCCCCAGTGTGCAGAGGATGGCAGCTTCCAGACT   180

Query   181  GTTCAGTGCCAAAACGATGGAAGATCTTGCTGGTGTGTTGGAGCTAACGGATCTGAGGTT   240
             || |||||||| ||||| || | || |||||||||||||||||||| || || |||||||
Sbjct   181  GTCCAGTGCCAGAACGACGGCCGCTCCTGCTGGTGTGTGGGTGCCAACGGCAGTGAAGTG   240

Query   241  TTGGGATCTAGGCAACCAGGTAGACCAGTTGCTTGCCTTTCTTTCTGCCAGCTTCAGAAG   300
             |||||    ||||| |||||    || || || || || ||||| ||||| |||||
Sbjct   241  CTGGGCAGCAGGCAGCCAGGACGGCCTGTGGCTTGTCTGTCATTTGTCAGCTACAGAAA   300

Query   301  CAGCAGATTCTTCTCTCCGGTTACATCAACTCTACCGACACCTCTTATCTTCCACAGTGC   360
             |||||||| || ||  || ||||| |||   || |||||||| || || || || |||||
Sbjct   301  CAGCAGATCTTACTGAGTGGCTACATTAACAGCACAGACACCTCCTACCTCCCTCAGTGT   360

Query   361  CAGGATTCTGGTGATTACGCTCCAGTTCAATGCGACGTTCAACAAGTTCAATGCTGGTGC   420
             |||||||| || || ||||| || |||| || || || || || || || || |||||||
Sbjct   361  CAGGATTCAGGGGACTACGCGCCTGTCAGTGTGATGTGCAGCAGGTCCAGTGCTGGTGT   420

Query   421  GTTGATGCTGAGGGAATGGAAGTTTACGGAACCAGACAACTTGGAAGGCCAAAGAGATGC   480
             || || || |||||  ||||| || || || || ||| | || || |||||||||  ||||
Sbjct   421  GTGGACGCAGAGGGGATGGAGGTGTATGGGACCCGCCAGCTGGGGAGGCCAAAGCGATGT   480

Query   481  CCAAGATCCTGCGAGATTAGGAACAGAAGGCTTCTTCACGGAGTTGGAGATAAGTCTCCA   540
             |||||   ||| || || || || ||   | ||||| ||||| |||||||||| ||||||
Sbjct   481  CCAAGGAGCTGTGAAATAAGAAATCGTCGTCTTCTCCACGGGGTGGGAGATAAGTCACCA   540

Query   541  CCACAATGCTCTGCTGAAGGCGAGTTCATGCCTGTTCAGTGCAAGTTCGTGAACACCACC   600
             || || || ||||| |||||||||| || ||||||| ||||||||||| || |||||||
Sbjct   541  CCCCAGTGTTCTGCGGAGGGAGAGTTTATGCCTGTCCAGTGCAAATTTGTCAACACCACA   600

Query   601  GACATGATGATTTTCGATCTCGTGCACTCCTATAACAGATTCCCAGATGCCTTCGTGACT   660
             ||||||||||||||| ||||| ||| |||||| | ||||| |||||||||| || |||||
Sbjct   601  GACATGATGATTTTTGATCTGGTCCACAGCTACAACAGGTTCCAGATGCATTTGTGACC   660

Query   661  TTCTCTTCCTTCCAGAGAAGATTCCCAGAGGTTTCAGGATATTGCCACTGCGCTGATTCT   720
             |||    ||||||||||||| ||||| || ||||| ||||| || || |||||||||||||
Sbjct   661  TTCAGTTCCTTCCAGAGGAGGTTCCCTGAGGTATCTGGGTATTGCCACTGTGCTGACAGC   720

Query   721  CAAGGTAGAGAGCTTGCTGAGACTGGACTTGAGCTTCTCCTCGATGAGATCTACGATACC   780
             ||||| | || || || ||||||||| ||  || | | || || || || || || |||
Sbjct   721  CAAGGGCGGGAACTGGCTGAGACAGGTTTGGAGTTGTTACTGGATGAAATTTATGACACC   780

Query   781  ATTTTCGCTGGACTTGATCTTCCATCTACCTTCACCGAGACTACCCTTTACAGGATTCTC   840
             ||||| ||||| || || || || || || ||||||||| || |||||| || |||| ||
Sbjct   781  ATTTTTGCTGGCCTGGACCTTCCTTCCACCTTCACTGAAACCACCCTGTACCGGATACTG   840

Query   841  CAAAGAAGATTCCTGCTGTTCAGTCTGTTATTTCCGGAAGATTCAGGTGCCCAACTAAG   900
             || ||| | ||||||||| || || ||  || ||||| ||||| | |||||  || ||
Sbjct   841  CAGAGACGGTTCCTCGCAGTTCAATCAGTCATCTCTGGCAGATTCCGATGCCCCACAAAA   900
```

Fig. 10A

```
Query   901   TGCGAGGTTGAGAGGTTCACTGCTACTTCATTCGGACATCCATACGTTCCATCTTGCAGA   960
              || || || ||| |||| || || ||    || || || || || ||||||   ||| |
Sbjct   901   TGTGAAGTGGAGCGGTTTACAGCAACCAGCTTTGGTCACCCCTATGTTCCAAGCTGCCGC   960

Query   961   AGAAACGGCGATTACCAGGCTGTTCAATGCCAAACTGAGGGACCATGTTGGTGTGTTGAT  1020
              |||| |||||| || |||| || ||||| || ||||| || || || || |||||||| ||
Sbjct   961   CGAAATGGCGACTATCAGGCGGTGCAGTGCCAGACGGAAGGGCCCTGCTGGTGTGTGGAC  1020

Query  1021   GCCCAGGGAAAAGAAATGCATGGAACCAGGCAACAAGGTGAACCACCATCTTGCGCTGAA  1080
              |||||||| || |||||||||||||||||| |||| |||||| || || |||||||| ||||||
Sbjct  1021   GCCCAGGGGAAGGAAATGCATGGAACCCGGCAGCAAGGGGAGCCGCCATCTTGTGCTGAA  1080

Query  1081   GGACAATCTTGCGCTTCTGAGAGGCAACAAGCTCTTTCTAGGCTCTACTTCGGAACCTCT  1140
              || |||||||| ||  || || || ||||  || || || ||||| ||||||| || |
Sbjct  1081   GGCCAATCTTGTGCCTCCGAAAGGCAGCAGGCCTTGTCCAGACTCTACTTTGGGACCTCA  1140

Query  1141   GGATACTTCTCCCAGCACGATCTTTTCTCTTCACCAGAGAAGAGATGGGCTTCTCCAAGA  1200
              || ||||||  |||||||||||  |||||||||| ||||||| ||||||| |||||||||| ||||||||
Sbjct  1141   GGCTACTTCAGCCAGCACGACCTGTTCTCTTCCCCAGAGAAAAGATGGGCCTCTCCAAGA  1200

Query  1201   GTTGCTAGATTCGCTACTTCTTGCCCACCAACCATCAAAGAGCTTTTCGTTGATTCCGGA  1260
              || || |||||  || ||  ||  ||||||||| || |||||  ||||| ||||| ||  ||
Sbjct  1201   GTAGCCAGATTTGCCACATCCTGCCCACCCACGATCAAGGAGCTCTTTGTGGACTCTGGG  1260

Query  1261   CTTCTTAGGCCAATGGTTGAGGGACAATCTCAGCAGTTCTCTGTGTCTGAGAACCTTCTC  1320
              ||||| |  |||||||||  ||||||||||| |||||||    || |||||  ||  || || || ||||||
Sbjct  1261   CTTCTCCGCCCAATGGTGGAGGGACAGAGCCAACAGTTTTCTGTCTCAGAAAATCTTCTC  1320

Query  1321   AAAGAGGCTATTAGGGCTATTTTCCCATCTAGGGGACTTGCTAGGCTTGCTCTTCAATTC  1380
              ||||| ||| ||  ||  | || ||||| || ||   | || || | ||||| ||||| ||
Sbjct  1321   AAAGAAGCCATCCGAGCAATTTTTCCCTCCCGAGGGCTGGCTCGTCTTGCCCTTCAGTTT  1380

Query  1381   ACCACCAACCCAAAGAGGCTTCAGCAAAACCTTTTCGGAGGAAAGTTCCTCGTTAATGTG  1440
              ||||||||||||||||| || ||||||||||||| ||||||| |||| || ||  | || |||||
Sbjct  1381   ACCACCAACCCAAAGAGACTCCAGCAAAACCTTTTTGGAGGGAAATTTTGGTGAATGTT  1440

Query  1441   GGACAGTTCAACCTTTCTGGTGCTCTTGGAACTAGGGGAACCTTCAACTTCTCTCAGTTC  1500
              || |||||  |||  | |||| || |||| ||  || || || ||  ||  ||||||   ||
Sbjct  1441   GGCCAGTTTAACTTGTCTGGAGCCCTTGGCACAAGAGGCACATTTAACTTCAGTCAATTT  1500

Query  1501   TTCCAGCAACTTGGACTTGCTTCTTTCCTTAACGGTGGCAGGCAAGAGGATCTTGCAAAG  1560
              |||||||||||||||| ||||| |||   || | || || || || || |||| | || |||
Sbjct  1501   TTCCAGCAACTTGGTCTTGCAAGCTTCTTGAATGGAGGGAGACAAGAAGATTGGCCAAG  1560

Query  1561   CCACTTTCTGTGGGACTTGATTCTAACTCTTCCACTGGAACTCCAGAGGCTGCTAAGAAA  1620
              ||||| |||||||||| |||| || |||||||  || ||||||| || || ||||||||||
Sbjct  1561   CCACTCTCTGTGGGATTAGATTCAAATTCTTCCACAGGAACCCCTGAAGCTGCTAAGAAG  1620

Query  1621   GATGGCACCATGAACAAGCCAACTGTGGG-ATCTTTCGGCTTCGAGATCAACCTTCAAGA  1679
              ||||| || || |  |||||||||||||| ||||  |||||| ||  || || || ||||
Sbjct  1621   GATGGTACTATGAATAAGCCAACTGTGGGCAGCTTT-GGCTTTGAAATTAACCTACAAGA  1679

Query  1680   GAACCAGAACGCTCTTAAGTTCCTTGCTTCCCTTCTTGAGCTTCCAGAGTTCCTTCTTTT  1739
              |||||| |  ||  || || || ||||||| | || ||||||||||| || |||||| ||
Sbjct  1680   GAACCAAAATGCCCTCAAATTCCTTGCTTCTCTCCTGGAGCTTCCAGAATTCCTTCTCTT  1739

Query  1740   CCTCCAGCACGCTATTTCTGTTCCAGAGGATGTGGCTAGAGATCTTGGTGATGTGATGGA  1799
              | | || || |||||  ||||  ||||||||||||| || |||  || |||||||||||||
Sbjct  1740   CTTGCAACATGCTATCTCTGTGCCAGAAGATGTGGCAAGAGATTTAGGTGATGTGATGGA  1799

Query  1800   AACCGTGCTTTCTTCTCAAACTTGCGAGCAAACTCCAGAGAGACTTTTCGTTCCTTCTTG  1859
```

Fig. 10B

```
            ||| || ||     || || || || ||||| || || || || || || || || || ||
Sbjct  1800 AACGGTACTCAGCTCCCAGACCTGTGAGCAGACACCTGAAAGGCTATTTGTCCCATCATG  1859

Query  1860 CACTACTGAGGGATCTTACGAGGATGTTCAGTGCTTCTCTGGTGAGTGTTGGTGCGTTAA  1919
            ||| || || |||    || ||||||||| || ||||| || || ||||| ||||| || ||
Sbjct  1860 CACGACAGAAGGAAGCTATGAGGATGTCCAATGCTTTTCCGGAGAGTGCTGGTGTGTGAA  1919

Query  1920 CTCTTGGGGAAAAGAGCTTCCAGGATCAAGAGTTAGAGGTGGACAACCTAGATGCCCAAC  1979
            || |||||| ||||||||||||||| |||||||| |||||||||| || || || ||||||
Sbjct  1920 TTCCTGGGGCAAAGAGCTTCCAGGCTCAAGAGTCAGAGGTGGACAGCCAAGGTGCCCCAC  1979

Query  1980 TGATTGCGAGAAGCAAAGGGCTAGGATGCAATCTCTTATGGGATCTCAGCCAGCTGGATC  2039
            || || || ||||||||||||| ||||||   || ||||| ||||| ||||| || ||
Sbjct  1980 AGACTGTGAAAAGCAAAGGGCTCGCATGCAAAGCCTCATGGGCAGCCAGCCTGCTGGCTC  2039

Query  2040 TACTCTTTTCGTGCCAGCTTGCACTTCTGAAGGACACTTCCTTCCAGTGCAATGCTTCAA  2099
            ||  | || || || ||||| |||   ||| ||||| ||||| || || || ||||||||
Sbjct  2040 CACCTTGTTTGTCCCTGCTTGTACTAGTGAGGGACATTTCCTGCCTGTCCAGTGCTTCAA  2099

Query  2100 CTCTGAGTGCTATTGCGTGGATGCTGAAGGTCAAGCTATTCCAGGAACCAGATCCGCTAT  2159
            ||| |||||||| || || ||||||||| ||||| || ||||| ||||| ||   || ||
Sbjct  2100 CTCAGAGTGCTACTGTGTTGATGCTGAGGGTCAGGCCATTCCTGGAACTCGAAGTGCAAT  2159

Query  2160 TGGCAAGCCAAAGAAGTGCCCAACTCCTTGCCAACTTCAATCTGAGCAGGCTTTCCTTAG  2219
            || ||||| ||||| || || || ||||  | ||  |  || |||||| ||||||||||||
Sbjct  2160 AGGGAAGCCCAAGAAATGCCCCACGCCCTGTCAATTACAGKCTGAGCAAGCTTTCCTCAG  2219

Query  2220 GACTGTTCAGGCTCTTCTTTCCAACTCTTCCATGCTTCCAACCCTTTCCGATACCTACAT  2279
            ||| || ||||| || || || ||||      |||||| || ||||||||| ||||||||
Sbjct  2220 GACGGTGCAGGCCCTGCTCTCTAACTCCAGCATGCTACCCACCCTTTCCGACACCTACAT  2279

Query  2280 TCCACAGTGCTCTACTGATGGACAGTGGAGACAAGTTCAGTGTAACGGACCACCAGAGCA  2339
            |||||||||     ||  || |||||||||||||||  || || || || || || |||||
Sbjct  2280 CCCACAGTGCAGCACCGATGGCAGTGGAGACAAGTGCAATGCAATGGGCCTCCYGAGCA  2339

Query  2340 AGTTTTCGAGCTTTACCAGAGATGGGAGGCTCAAAACAAGGGACAAGATCTCACTCCAGC  2399
            || || ||||| | |||||  |||||||||| |||| |||||| ||||| || || || ||
Sbjct  2340 GGTCTTCGAGTTGTACCAACGATGGGAGGCTCAGAACAAGGGCCAGGATCTGACGCCTGC  2399

Query  2400 TAAGTTGCTCGTGAAGATCATGTCTTACAGAGAGGCTGCTTCTGGAAACTTCAGCCTCTT  2459
            || |||| ||||||||||||||  ||||||||||| |||||| || || |||||||||||
Sbjct  2400 CAAGCTGCTAGTGAAGATCATGAGCTACAGAGAAGCAGCTTCCGGAAACTTCAGTCTCTT  2459

Query  2460 CATCCAGTCACTTTACGAGGCTGGACAGCAAGATGTTTTCCCAGTGCTTTCTCAGTACCC  2519
            || ||    || || ||||||| ||||| || || ||||||| ||||| || || |||||
Sbjct  2460 TATTCAAAGTCTGTATGAGGCTGGCCAGCAAGATGTCTTCCCGGTGCTGTCACAATACCC  2519

Query  2520 ATCTCTTCAGGATGTTCCACTTGCTGCTCTTGAGGGAAAAAGACCACAGCCAAGAGAGAA  2579
            |||||  || |||| ||||| || || || ||  ||  ||| | | |||| || || |||
Sbjct  2520 TTCTCTGCAAGATGTCCCACTAGCAGCACTGGAAGGGAAACGGCCCCAGCCCAGGGAGAA  2579

Query  2580 CATTCTTCTCGAGCCTTACCTCTTCTGGCAGATTCTTAACGGACAGCTTTCACAGTATCC  2639
            || || || |||||||| |||||||||||||| ||  | || ||   ||   ||| ||||
Sbjct  2580 TATCCTCCTGGAGCCCTACCTCTTCTGGCAGATCTTAAATGGCCAACTCAGCCAATACCC  2639

Query  2640 TGGTTCCTACTCTGATTTCTCTACCCCACTCGCTCATTTCGATCTTAGAAACTGCTGGTG  2699
            || |||||||||| |||| ||   ||   | |||||| ||||| ||||| || ||||||||
Sbjct  2640 GGGGTCCTACTCAGACTTCAGCACTCCTTTGGCACATTTTGATCTTCGGAACTGCTGGTG  2699

Query  2700 TGTGGATGAAGCTGGACAAGAGCTTGAGGGAATGAGATCTGAGCCATCTAAGTTGCCAAC  2759
            |||||||||| ||||| ||||| ||||| ||||| | ||||||||   ||| | |||||
```

Fig. 10C

```
Sbjct  2700  TGTGGATGAGGCTGGCCAAGAACTGGAAGGAATGCGGTCTGAGCCAAGCAAGCTCCCAAC  2759

Query  2760  TTGCCCAGGATCTTGCGAGGAAGCTAAGTTGAGAGTGCTCCAGTTCATTAGGGAAACCGA  2819
             ||  || || || || |||||||| |||  |  || || ||||||||||||||||| ||
Sbjct  2760  ATGTCCTGGCTCCTGTGAGGAAGCAAAGCTCCGTGTACTGCAGTTCATTAGGGAAACGGA  2819

Query  2820  GGAAATTGTGTCTGCTTCTAACTCCTCTAGGTTCCCACTTGGAGAGTCTTTCCTTGTGGC  2879
             ||  |||||| || |||||  ||    ||| |||||||| || || |||  |||| |||
Sbjct  2820  AGAGATTGTTTCAGCTTCCAACAGTTCTCGGTTCCCTCTGGGGGAGAGTTTCCTGGTGGC  2879

Query  2880  TAAGGGAATTAGGCTTAGGAACGAGGATCTTGGACTTCCACCACTTTTCCCACCAAGAGA  2939
             ||||||||   ||||  |||||  ||||| ||||| ||||  || ||||  |  || ||
Sbjct  2880  CAAGGGAATCCGGCTGAGGAATGAGGACCTCGGCCTTCCTCCGCTCTTCCCGCCCCGGGA  2939

Query  2940  GGCTTTCGCTGAACAATTCCTCAGGGGTTCCGATTATGCTATTAGGCTTGCTGCTCAGTC  2999
             |||||||||  || |||||||  || ||  ||    || ||| || || || ||||||| 
Sbjct  2940  GGCTTTCGCGGAGCAGTTCTGCGTGGGAGTGATTACGCCATTCGCCTGGCGGCTCAGTC  2999

Query  3000  TACCTTGTCTTTCTACCAGAGAAGAAGGTTCTCTCCAGACGATTCTGCTGGTGCTTCTGC  3059
             ||||| |    ||||| ||||||||  ||||| |  | | || ||||| ||  || || |
Sbjct  3000  TACCTTAAGCTTCTATCAGAGACGCCGCTTTTCCCCGGACGACTCGGCTGGAGCATCCGC  3059

Query  3060  TCTTCTTAGATCCGGACCTTACATGCCACAATGCGACGCTTTTGGATCTTGGGAGCCAGT  3119
             ||||| | || || ||  || |||||||||| || || |||||  |||| ||||||| ||
Sbjct  3060  CCTTCTGCGGTCGGGCCCCTACRTGCCACAGTGTGATGCGTTTGGAAGTTGGGAGCCTGT  3119

Query  3120  TCAATGTCATGCTGGAACTGGACACTGTTGGTGCGTGGATGAGAAGGGCGGTTTCATTCC  3179
             || || |  ||||| ||||| ||||| ||||| || ||||||||| || |||  ||||
Sbjct  3120  GCAGTGCCACGCTGGGACTGGGCACTGCTGGTGTGTAGATGAGAAAGGAGGGTTCATCCC  3179

Query  3180  AGGATCTCTTACCGCTAGATCCCTTCAGATTCCACAATGCCCTACTACTTGCGAGAAGTC  3239
             || || || ||  |  || |   | || |||||||||||||| || |  ||||||  ||
Sbjct  3180  TGGCTCACTGACTGCCCGCTCTCTGCAGATTCCACAGTGCCCGACAACCTGCGAGAAATC  3239

Query  3240  TAGGACCTCTGGACTTCTTTCTTCTTGGAAGCAGGCTAGGTCACAAGAAAACCCATCCCC  3299
             |  ||   ||| ||| ||||| |||||||| || ||||| |  ||||||||||||| ||
Sbjct  3240  TCGAACCAGTGGGCTGCTTTCCAGTTGGAAACAGGCTAGATCCCAAGAAAACCCATCTCC  3299

Query  3300  AAAGGATCTTTTCGTTCCAGCATGCCTTGAGACTGGTGAGTATGCTAGACTTCAGGCTTC  3359
             ||| | || ||| || |||||||| || |||||  | || ||||| | ||| || || ||
Sbjct  3300  AAAAGACCTGTTCGTCCCAGCCTGCCTAGAAACAGGAGAGTATGCCAGGCTGCAGGCATC  3359

Query  3360  TGGTGCTGGAACATGGTGTGTTGACCCAGCTTCTGGTGAAGAACTTAGGCCAGGATCTTC  3419
             |  || ||| || ||||||||| | ||||  | ||||  || ||     |||| ||  |
Sbjct  3360  GGGGGCTGGCACCTGGTGTGTGGACCCTGCATCAGGAGAAGAGTTGCGGCCTGGCTCGAG  3419

Query  3420  TTCTTCTGCTCAGTGCCCATCTTTGTGCAACGTGCTTAAGTCTGGTGTTCTTTCCAGAAG  3479
                |||  |||||||||       |  |||||| ||||| |||  || || || ||  ||
Sbjct  3420  CAGCAGTGCCCAGTGCCCAAGCCTCTGCAATGTGCTCAAGAGTGGAGTCCTCTCTAGGAG  3479

Query  3480  AGTGTCTCCAGGATATGTTCCAGCTTGCAGAGCTGAGGATGGTGGATTCTCTCCAGTTCA  3539
             |||     |||| ||||| ||||| ||||  ||  ||||||| ||  ||  || || ||
Sbjct  3480  AGTCAGCCCAGGCTATGTCCCAGCCTGCAGGGCAGAGGATGGGGGCTTTTCCCCAGTGCA  3539

Query  3540  GTGTGATCAAGCTCAAGGATCTTGTTGGTGCGTGATGGATTCTGGTGAAGAGGTTCCAGG  3599
             |||||  || ||  || || ||     ||||||| || || ||  ||||||| || |||
Sbjct  3540  ATGTGACCAGGCCCAGGGCAGCTGCTGGTGTGTCATGGACAGCGGAGAAGAGGTGCCTGG  3599

Query  3600  AACTAGAGTTACTGGCGGACAACCAGCTTGTGAATCTCCAAGATGCCCACTTCCATTCAA  3659
             ||  | ||| || || || ||  ||||| || || |   | ||||| || ||||||||||
Sbjct  3600  GACGCGCGTGACCGGGGGCCAGCCCGCCTGTGAGAGCCCGCGGTGTCCGCTGCCATTCAA  3659
```

Fig. 10D

```
Query  3660  CGCTTCAGAGGTTGTGGGAGGAACTATTCTCTGCGAGACTATTTCTGGACCAACCGGTTC  3719
             ||| || |||||| || || |||||| || || || ||||| || || || || || ||
Sbjct  3660  CGCGTCGGAGGTGGTTGGTGGAACAATCCTGTGTGAGACAATCTCGGGCCCCACAGGCTC  3719

Query  3720  TGCTATGCAACAATGCCAGCTTTTGTGCAGACAAGGATCTTGGTCTGTTTTCCCACCAGG  3779
             ||| |||||| || |||||  | |||||| |||||| || |||   || || ||||||||
Sbjct  3720  TGCCATGCAGCAGTGCCAATTGCTGTGCCGCCAAGGCTCCTGGAGCGTGTTTCCACCAGG  3779

Query  3780  ACCACTTATTTGCTCCCTTGAGTCTGGAAGATGGGAGTCTCAACTTCCACAACCTAGAGC  3839
             ||| | || ||   ||| |||   ||| | |||||||| || || || || || | ||
Sbjct  3780  GCCATTGATATGTAGCCTGGAGAGCGGACGCTGGGAGTCACAGCTGCCTCAGCCCCGGGC  3839

Query  3840  TTGCCAAAGACCACAACTCTGGCAAACTATTCAGACCCAGGGACATTTCCAACTTCAACT  3899
             |||||| | || || || ||||| || || |||||||| || || ||| || || || ||
Sbjct  3840  CTGCCAACGGCCCCAGCTGTGGCAGACCATCCAGACCCAAGGGCACTTTCAGCTCCAGCT  3899

Query  3900  CCCACCTGGAAAGATGTGCTCTGCTGATTACGCTGATCTTCTCCAGACTTTCCAGGTGTT  3959
             ||| || || |||||||||| |||||||||||  ||||| ||||| || |||||||| ||
Sbjct  3900  CCCGCCGGGCAAGATGTGCAGTGCTGACTACGCGGGTTTGCTGCAGACTTTCCAGGTTTT  3959

Query  3960  CATCCTCGATGAGCTTACTGCTAGAGGATTCTGCCAGATCCAGGTTAAGACTTTCGGAAC  4019
             |||  | ||||||||| || ||  | || ||||||||||||||||| ||||||| || ||
Sbjct  3960  CATATTGGATGAGCTGACAGCCCGCGGCTTCTGCCAGATCCAGGTGAAGACTTTTGGCAC  4019

Query  4020  CCTCGTTTCTATTCCAGTGTGCAACAACTCTTCTGTTCAAGTGGGATGCCTTACTAGAGA  4079
             ||| ||||| |||||| || |||||||||| || ||||| || |||| ||| || || ||
Sbjct  4020  CCTGGTTTCCATTCCTGTCTGCAACAACTCCTCTGTGCAGGTGGGTTGTCTGACCAGGGA  4079

Query  4080  GAGGCTCGGAGTTAACGTTACTTGGAAGTCCAGGCTCGAGGATATTCCTGTTGCTTCCCT  4139
             | |   |||||| ||| || || |||  ||   || || || || |||||| || || ||
Sbjct  4080  GCGTTTAGGAGTGAATGTTACATGGAAATCACGGCTTGAGGACATCCCAGTGGCTTCTCT  4139

Query  4140  CCCAGATCTTCACGATATTGAGAGGGCTCTTGTGGGAAAGGATCTTCTTGGTAGGTTCAC  4199
             || || | ||  || || || ||||| |||||| ||||||||||  ||||  | ||||||
Sbjct  4140  TCCTGACTTACATGACATTGAGAGAGCCTTGGTGGGCAAGGATCTCCTTGGGCGCTTCAC  4199

Query  4200  CGATCTTATTCAGTCTGGTTCCTTCCAGCTTCACCTTGATTCTAAGACCTTCCCAGCTGA  4259
             ||||| || |||   ||| || ||||||||||| ||||| |||||| |||||||||| ||
Sbjct  4200  AGATCTGATCCAGAGTGGCTCATTCCAGCTTCATCTGGACTCCAAGACGTTCCCAGCGGA  4259

Query  4260  GACTATTAGATTCCTCCAGGGTGATCACTTTGGAACTTCTCCAAGAACCTGGTTCGGATG  4319
             || ||  | ||||||||| || || |||||| || || || ||||| || || || ||
Sbjct  4260  AACCATCCGCTTCCTCCAAGGGGACCACTTTGGCACCTCTCCCAGGACATGGTTTGGGTG  4319

Query  4320  CTCTGAGGGATTCTACCAAGTGCTTACCTCTGAGGCTTCTCAAGATGGACTTGGATGCGT  4379
             ||| || |||||||||||||| ||| ||     ||||||   || ||||| ||||||||
Sbjct  4320  CTCGGAAGGATTCTACCAAGTCTTGACAAGTGAGGCCAGTCAGGACGGACTGGGATGCGT  4379

Query  4380  TAAGTGCCCAGAGGGATCATATTCTCAGGACGAGGAATGCATTCCATGCCCAGTTGGTTT  4439
             ||||| || ||  || |  ||||| || || |||||||||||||| || || |||| ||
Sbjct  4380  TAAGTGTCCTGAAGGAAGCTATTCCCAAGATGAGGAATGCATTCCTTGTCCTGTTGGATT  4439

Query  4440  CTACCAAGAGCAGGC-TGGATCTCTTGCTTGTGTTCCTTGCCCTGTTGGAAGGACTACTA  4498
             ||||||||| ||||| ||| |||  ||| || |  || ||||| ||||| || || || |
Sbjct  4440  CTACCAAGAACAGGCAGGGAGCT-TGGCCTGTGTCCCATGTCCTGTGGGCAGAACGACCA  4498

Query  4499  TTTCCGCTGGTGCTTTCTCTCAGACTCATTGCGTTACTGATTGCCAGAGAAACGAGGCTG  4558
             ||| |  |||||||||  ||||| ||| |||  ||||||||| || |||| ||||| | |
Sbjct  4499  TTTCTGCYGGAGCTTTCAGCCAGACTCACTGTGTCACTGACTGTCAGAGGAACGAAGCAG  4558

Query  4559  GATTGCAATGCGATCAGAACGGACAGTATAGGGCTTCTCAGAAGGATAGAGGTTCCGGAA  4618
```

Fig. 10E

```
               |  ||||||||  ||  ||||||  ||  ||||||  |  ||      ||||||||||  ||  ||       ||  |
Sbjct   4559   GCCTGCAATGTGACCAGAATGGCCAGTATCGAGCCAGCCAGAAGGACAGGGGCAGTGGGA   4618

Query   4619   AGGCTTTCTGCGTTGATGGTGAAGGTAGAAGATTGCCTTGGTGGGAGACTGAAGCTCCAC   4678
               ||||  |||||  ||  ||  ||  ||  ||   |  ||   ||||  ||||||||||  ||  ||  ||  ||  |
Sbjct   4619   AGGCCTTCTGTGTGGACGGCGAGGGGCGGAGGCTGCCATGGTGGGAAACAGAGGCCCCTC   4678

Query   4679   TTGAGGATTCTCAGTGCCTCATGATGCAAAAGTTCGAGAAGGTGCCAGAGTCTAAGGTTA   4738
               ||||||||  ||  ||||||   |  |||||||||  |||||  ||||||||||  |||||  ||  ||||||  |
Sbjct   4679   TTGAGGACTCACAGTGTTTGATGATGCAGAAGTTTGAGAAGGTTCCAGAATCAAAGGTGA   4738

Query   4739   TCTTCGACGCTAACGCTCCAGTTGCTGTTAGATCCAAGGTGCCAGATTCTGAGTTCCCAG   4798
               ||||||||||  ||  ||||||  ||  ||||||  ||||||||||  ||  ||  ||||||||||||  |
Sbjct   4739   TCTTCGACGCCAATGCTCCTGTGGCTGTCAGATCCAAAGTTCCTGATTCTGAGTTCCCCG   4798

Query   4799   TGATGCAATGCCTTACTGATTGCACTGAGGATGAGGCTTGCTCATTCTTCACTGTGTCTA   4858
               |||||||||  |||  |  ||  ||||||||||  |||||  |||||  |||        ||||||||  |  |
Sbjct   4799   TGATGCAGTGCTTGACAGATTGCACAGAGGACGAGGCCTGCAGCTTCTTCACCGTGTCCA   4858

Query   4859   CTACCGAGCCAGAGATTTCCTGCGATTTCTACGCTTGGACCTCTGATAACGTTGCTTGCA   4918
               |  ||  ||||||||||||||||||||  ||||||||  ||||||||||     |||  ||  ||||||  ||||
Sbjct   4859   CGACGGAGCCAGAGATTTCCTGTGATTTCTATGCTTGGACAAGTGACAATGTTGCCTGCA   4918

Query   4919   TGACCTCTGATCAAAAGAGGGATGCTCTCGGAAACTCTAAGGCTACCTCCTTCGGATCTC   4978
               ||||  |||||  ||  ||   |  ||||||  ||  ||  ||||||  |||||  |||   |||  |||  |||   ||
Sbjct   4919   TGACTTCTGACCAGAAACGAGATGCACTGGGGAACTCAAAGGCCACCAGCTTTGGAAGTC   4978

Query   4979   TTAGGTGCCAAGTGAAAGTTAGATCCCACGGACAAGATTCTCCAGCTGTGTACCTTAAGA   5038
               ||  |  ||||||  ||||||||||  ||      |||  ||  ||||||||||||||||||||||  |  |||  |
Sbjct   4979   TTCGCTGCCAGGTGAAAGTGAGGAGCCATGGTCAAGATTCTCCAGCTGTGTATTTGAAAA   5038

Query   5039   AGGGACAAGGATCTACTACTACCCTCCAGAAGAGATTCGAGCCAACTGGATTCCAGAACA   5098
               ||||  ||||||||||  ||  ||  ||  ||||||   |  ||  ||  ||  |||||  |||||  ||||
Sbjct   5039   AGGGCCAAGGATCCACCACAACACTTCAGAAACGCTTTGAACCCACTGGTTTCCAAAACA   5098

Query   5099   TGCTTTCCGGACTCTACAACCCAATTGTGTTCTCTGCTTCCGGTGCTAACCTTACCGATG   5158
               ||||||||  |||   |||  ||||||||||||  |||||||||  ||  ||  ||  ||  ||  ||||||||
Sbjct   5099   TGCTTTCTGGATTGTACAACCCCATTGTGTTCTCAGCCTCAGGAGCCAATCTAACCGATG   5158

Query   5159   CTCACCTTTTCTGCCTTTTGGCTTGCGATAGAGATCTTTGCTGCGACGGATTCGTTCTTA   5218
               ||||||||  |||||  |||  |||  |  ||  |||||  |  |||||  ||  ||||||  ||  |||||  ||  |
Sbjct   5159   CTCACCTCTTCTGTCTTCTTGCATGCGACCGTGATCTGTGTTGCGATGGCTTCGTCCTCA   5218

Query   5219   CTCAAGTTCAGGGTGGAGCTATTATTTGCGGACTTCTCTCTTCTCCTTCCGTGT--TGCT   5276
               |  ||  ||||||  ||  ||  ||  ||  ||  ||   |  ||      ||  ||  ||||  ||||
Sbjct   5219   CACAGGTTCAAGGAGGTGCCATCATCTGTGGGTTGCTGAGCTCACC--CAGTGTCCTGCT   5276

Query   5277   CTGCAACGTTAAGGATTGGATGGACCCATCTGAGGCTTGGGCTAACGCTACTTGCCCAGG   5336
               ||  ||  ||  ||  ||   ||||||||  ||  |||||  ||  |||||||||  |||||  ||  ||  ||
Sbjct   5277   TTGTAATGTCAAAGACTGGATGGATCCCTCTGAAGCCTGGGCTAATGCTACATGTCCTGG   5336

Query   5337   TGTTACCTACGATCAAGAGTCTCACCAAGTGATTCTTAGGCTCGGCGATCAAGAGTTCAT   5396
               |||   |  ||  ||  ||  ||   |||||  |||||  |  |  |||  ||  ||  ||  ||||||||
Sbjct   5337   TGTGACATATGACCAGGAGAGCCACCAGGTGATATTGCGTCTTGGAGACCAGGAGTTCAT   5396

Query   5397   TAAGTCCCTTACCCCACTTGAGGGAACTCAAGACACCTTCACCAACTTCCAGCAGGTTTA   5456
               |  ||      ||  ||  ||  |  ||  ||||||||||||  |||||  ||  ||  ||||||||||||
Sbjct   5397   CAAGAGTCTGACACCCTTAGAAGGAACTCAAGACACCTTTACCAATTTTCAGCAGGTTTA   5456

Query   5457   CCTTTGGAAGGATTCCGATATGGGTTCTAGGCCAGAGTCTATGGGATGCAGGAAGGATAC   5516
               ||  ||||||  |||||  ||  ||||||   ||||  ||||||||||||||||  ||  ||     |  ||
```

Fig. 10F

```
Sbjct  5457  TCTCTGGAAAGATTCTGACATGGGGTCTCGGCCTGAGTCTATGGGATGTAGAAAARACAC  5516

Query  5517  TGTTCCAAGACCAGCTTCTCCAACTGAGGCTGGACTTACTACCGAGCTTTTCTCCCCAGT  5576
             ||  |||||  |||||||  || || ||  | ||  ||  || || ||||||||||  ||
Sbjct  5517  AGTGCCAAGGCCAGCATCTCCAACAGAAGCAGGTTTGACAACAGAACTTTTCTCCCCTGT  5576

Query  5577  TGATCTCAACCAGGTGATCGTTAACGGAAACCAGTCTCTTTCTTCCCAAAAGCACTGGCT  5636
             || ||||||||||| || || || ||||| ||  || || || ||    ||| ||||||||||
Sbjct  5577  GGACCTCAACCAGGTCATTGTCAATGGAAATCAATCACTATCCAGCCAGAAGCACTGGCT  5636

Query  5637  TTTCAAGCACCTTTTCTCTGCTCAACAGGCTAACCTTTGGTGCCTTTCCAGATGCGTTCA  5696
             ||||||||||| || || || || ||||| |||||  ||||||||||  | ||| ||  ||
Sbjct  5637  TTTCAAGCACCTGTTTTCAGCCCAGCAGGCAAACCTATGGTGCCTTTCTCGTTGTGTGCA  5696

Query  5697  AGAGCACTCTTTCTGCCAACTTGCTGAGATTACCGAGTCTGCTTCCCTTTACTTCACCTG  5756
             ||||||||||||||  ||  || || |||| || |||    |||  |||||||||||||
Sbjct  5697  GGAGCACTCTTTCTGTCAGCTCGCAGAGATAACAGAGAGTGCATCCTTGTACTTCACCTG  5756

Query  5757  CACCCTTTATCCAGAGGCTCAAGTGTGCGACGATATTATGGAATCCAACGCTCAAGGATG  5816
             ||||||  || |||||| || ||||||| || || || || ||||| |||||| || ||
Sbjct  5757  CACCCTCTACCCAGAGGCACAGGTGTGTGATGACATCATGGAGTCCAATGCCCAGGGCTG  5816

Query  5817  CAGGCTTATTCTTCCTCAGATGCCAAAGGCTCTCTTCAGGAAGAAGGTTATCCTCGAGGA  5876
             |||  || || || || |||||||||||||  || |||  ||||  || |||| |  ||
Sbjct  5817  CAGACTGATCCTGCCTCAGATGCCAAAGGCCCTGTTCCGGAAGAAAGTTATACTGGAAGA  5876

Query  5877  CAAGGTTAAGAACTTCTACACCAGGCTTCCATTCCAAAAGCTCATGGGCATTTCCATTAG  5936
             || ||  || ||||||| ||||  || ||  ||||||||| |||||| || ||||||||
Sbjct  5877  TAAAGTGAAGAACTTTTACACTCGCCTGCCGTTCCAAAAACTGATGGGGATATCCATTAG  5936

Query  5937  GAACAAGGTGCCAATGTCCGAGAAGTCTATCTCCAACGGATTCTTCGAGTGCGAGAGAAG  5996
             || || |||||  ||||| ||  ||  || || ||  |||  || || ||  |||| |
Sbjct  5937  AAATAAAGTGCCCATGTCTGAAAAATCTATTTCTAATGGGTTCTTTGAATGTGAACGACG  5996

Query  5997  ATGTGATGCTGATCCATGCTGCACTGGATTCGGATTCCTTAACGTGTCTCAGCTTAAGGG  6056
             ||  |||| |||| ||||||||||||  |||||  | |||| |||||  |||  ||||
Sbjct  5997  GTGCGATGCGGACCCATGCTGCACTGGCTTTGGATTTCTAAATGTTTCCCAGTTAAAAGG  6056

Query  6057  TGGAGAGGTTACCTGCCTTACCCTTAACTCCCTTGGAATCCAGATGTGCTCAGAGGAAAA  6116
             |||||||| || || ||  || ||  |||   | ||||| |||||||||   ||||| ||
Sbjct  6057  AGGAGAGGTGACATGTCTCACTCTGAACAGCTTGGGAATTCAGATGTGCAGTGAGGAGAA  6116

Query  6117  TGGTGGAGCTTGGAGGATTCTTGATTGCGGCTCCCCAGATATTGAGGTTCACACCTACCC  6176
             ||| || |||  |||| |||  || | || ||||  ||| ||||  ||||| |||| ||
Sbjct  6117  TGGAGGAGCCTGGCGCATTTTGGACTGTGGCTCTCCTGACATTGAAGTCCACACCTATCC  6176

Query  6177  ATTCGGATGGTATCAGAAGCCAATCGCTCAAAACAACGCTCCATCTTTCTGCCCTCTTGT  6236
             |||||||||| | ||||||||  |  ||||||  || ||||||    ||||||   | ||
Sbjct  6177  CTTCGGATGGTACCAGAAGCCCATTGCTCAAAATAATGCTCCCAGTTTTGCCCTTTGGT  6236

Query  6237  GGTGCTTCCATCTCTTACTGAGAAGGTGTCCCTTGATTCTTGGCAGTCTCTTGCTCTTTC  6296
             | || || || || || ||  || ||||| || |||| ||  ||||||| || || |||
Sbjct  6237  TGTTCTGCCTTCCCTCACAGAGAAAGTGTCTCTGGACTCGTGGCAGTCCCTGGCCCTCTC  6296

Query  6297  TTCTGTTGTGGTGGACCCATCTATTAGGCATTTCGATGTGGCTCATGTTTCTACTGCTGC  6356
             ||  || || || ||  ||||| |||||||||| ||||| ||||||||  |  || ||||
Sbjct  6297  TTCAGTGGTTGTTGATCCATCCATTAGGCACTTTGATGTTGCCCATGTCAGCACTGCTGC  6356

Query  6357  CACCTCTAACTTCTCTGCTGTGAGGGATCTTTGCTTGTCTGAGTGCTCTCAACATGAGGC  6416
             ||||   || ||||||||||||  ||  || ||||| || ||| ||| |||||||||||
Sbjct  6357  CACCAGCAATTTCTCTGCTGTCCGAGACCTCTGTTTGTCGGAATGTTCCCAACATGAGGC  6416
```

Fig. 10G

```
Query  6417  TTGCCTTATTACTACTCTCCAAACCCAACCAGGTGCTGTGAGATGCATGTTCTACGCTGA  6476
             ||  || || ||  |||||  ||||||||||| || |||||||||||  ||||||||  |||||
Sbjct  6417  CTGTCTCATCACCACTCTGCAAACCCAACCTGGGGCTGTGAGATGTATGTTCTATGCTGA  6476

Query  6477  TACTCAGTCTTGCACCCATTCTCTTCAAGGACAGAACTGTAGGCTTCTTCTTAGGGAAGA  6536
             ||||||      |||||  |||  |||  || || |||||||||  |  |||||  |||  |  |||||
Sbjct  6477  TACTCAAAGCTGCACACATAGTCTGCAGGGTCAGAACTGCCGACTTCTGCTTCGTGAAGA  6536

Query  6537  GGCTACCCATATCTATAGGAAGCCAGGAATTTCTCTTCTTTCCTACGAGGCTTCTGTTCC  6596
             |||  ||||| |||||||   ||||||||||||| |||||| |||||  ||||  ||||| ||
Sbjct  6537  GGCCACCCACATCTACCGGAAGCCAGGAATCTCTCTGCTCAGCTATGAGGCATCTGTACC  6596

Query  6597  ATCTGTGCCAATTTCTACCCACGGAAGGCTTTTGGGAAGATCTCAGGCTATTCAAGTGGG  6656
             | |||||||| ||||| ||||| ||    ||||    ||||  ||  || ||||| ||  || |||||
Sbjct  6597  TTCTGTGCCCATTTCCACCCATGGCCGGCTGCTGGGCAGGTCCCAGGCCATCCAGGTGGG  6656

Query  6657  AACCTCATGGAAGCAAGTGGATCAGTTCCTTGGAGTTCCATATGCTGCTCCACCACTTGC  6716
             | |||||||||||||||||||  ||||||||||||||||||||||||||||||  ||  || || ||
Sbjct  6657  TACCTCATGGAAGCAAGTGGACCAGTTCCTTGGAGTTCCATATGCTGCCCCGCCCCTGGC  6716

Query  6717  TGAGAGAAGGTTCCAAGCTCCAGAGCCACTTAACTGGACTGGTTCTTGGGATGCTTCTAA  6776
             |||||  |  ||||||||  |||||||||| | |||||||||||  || ||  |||||||||    ||
Sbjct  6717  AGAGAGGCGCTTCCAGGCACCAGAGCCCTTGAACTGGACAGGCTCCTGGGATGCCAGCAA  6776

Query  6777  GCCAAGAGCTTCTTGCTGGCAACCAGGAACTAGGACTTCTACTTCTCCTGGTGTGTCTGA  6836
             ||||||  ||      |||||||| |||||  || ||  || || || |||||||||  ||     |||
Sbjct  6777  GCCAAGGGCCAGCTGCTGGCAGCCAGGCACCAGAACATCCACGTCTCCTGGAGTCAGTGA  6836

Query  6837  GGATTGCCTTTACCTCAACGTGTTCATCCCACAAAACGTTGCTCCAAACGCTTCTGTGCT  6896
             | ||||   |  ||  |||||  |||||||||||||||  || || || || ||  || ||||||||
Sbjct  6837  AGATTGTTTGTATCTCAATGTGTTCATCCCTCAGAATGTGGCCCCTAACGCGTCTGTGCT  6896

Query  6897  TGTGTTCTTCCACAACACTATGGATAGGGAAGAGTCTGAAGGATGGCCAGCTATTGATGG  6956
             |||||||||||||||||||  |||||  |||||  ||  |||||||||||||||  ||  || ||
Sbjct  6897  GGTGTTCTTCCACAACACCATGGACAGGGAGGAGAGTGAAGGATGGCCGGCTATCGACGG  6956

Query  6957  TTCTTTCCTCGCTGCTGTGGGAAACCTTATTGTGGTGACCGCTTCTTACAGAGTTGGTGT  7016
             || ||| | |||||||||||  ||  ||||||| || ||     |||  ||||  |||||
Sbjct  6957  CTCCTTCTTGGCTGCTGTTGGCAACCTCATCGTGGTCACTGCCAGCTACCGAGTGGGTGT  7016

Query  7017  GTTCGGATTCCTCTCTTCTGGATCTGGTGAAGTGTCTGGAAACTGGGGACTTCTTGATCA  7076
             |||||  |||||     ||||||  || || ||  || |||  |||  ||||||||  || || || ||
Sbjct  7017  CTTCGGCTTCCTGAGTTCTGGGTCCGGAGAGGTGAGTGGCAACTGGGGGCTGCTGGACCA  7076

Query  7077  AGTTGCTGCTCTTACTTGGGTTCAGACCCACATTAGAGGATTCGGAGGTGATCCAAGAAG  7136
             |  || || |||| ||  |||||| |||||||||  ||||||| ||  ||  || ||   |  |
Sbjct  7077  GGTGGCGGCTCTGACCTGGGTGCAGACCCACATCCGAGGATTTGGCGGGACCCTCGGCG  7136

Query  7137  AGTGTCCTTGGCTGCTGATAGAGGTGGAGCTGATGTGGCTTCTATTCACCTTCTTACCGC  7196
             ||||||  ||||  ||  |  | || ||||||||||||||||||  || |||||||| || ||
Sbjct  7137  CGTGTCCCTGGCAGCAGACCGTGGCGGGCTGATGTGGCCAGCATCCACCTTCTCACGGC  7196

Query  7197  AAGGGCTACTAACTCTCAGCTTTTTAGAAGGGCTGTTCTTATGGGAGGATCTGCTCTTTC  7256
             |||||  || || |||||  ||||| |  || ||||| |||||||||||||  ||  ||| ||
Sbjct  7197  CAGGGCCACCAACTCCCAACTTTTCCGGAGAGCTGTGCTGATGGGAGGCTCCGCACTCTC  7256

Query  7257  TCCAGCTGCTGTGATTTCTCATGAGAGGGCTCAACAACAGGCTATTGCTCTCGCTAAGGA  7316
             || || || || ||  |||||||||||||| || ||||||||  |||||| |||||||||||
Sbjct  7257  CCCGGCCGCCGTCATCAGCCATGAGAGGGCTCAGCAGCAGGCAATTGCTTTGGCAAAGGA  7316
```

Fig. 10H

```
Query  7317  AGTTTCCTGCCCAATGTCATCTTCTCAAGAGGTGGTGTCTTGCCTTAGACAAAAGCCAGC  7376
             ||    ||||| |||||||||    ||||| ||||||||| |||||  | || |||||  ||
Sbjct  7317  GGTCAGTTGCCCCATGTCATCCAGCCAAGAAGTGGTGTCCTGCCTCCGCCAGAAGCCTGC  7376

Query  7377  TAACGTGCTTAACGATGCTCAGACCAAGTTGTTGGCTGTTTCTGGACCATTCCATTACTG  7436
             || || || || ||||| |||||||||| | |||| ||  ||| || |||||  |||||
Sbjct  7377  CAATGTCCTCAATGATGCCCAGACCAAGCTCYTGGCCGTGAGTGGCCCCTTTCCACTACTG  7436

Query  7437  GGGACCAGTTATCGATGGACACTTCTTGAGAGAGCCACCTGCTAGAGCTTTGAAGAGATC  7496
             ||| || || ||||||||||||||| ||  | ||||| || ||||| |||  ||||| ||
Sbjct  7437  GGGTCCTGTGATCGATGGCCACTTCCTCCGTGAGCCTCCAGCCAGAGCACTGAAGAGGTC  7496

Query  7497  CCTTTGGGTGGAAGTGGATCTTCTTATTGGCTCCTCCCAGGATGATGGACTTATCAACAG  7556
              |    |||| |||||| ||| |||||| ||||||| ||  |||||| ||||||||||||
Sbjct  7497  TTTAYGGGTAGAGGTCGATCTGCTCATTGGGAGTTCTCAGGACGACGGGCTCATCAACAG  7556

Query  7557  GGCTAAGGCTGTTAAGCAGTTCGAGGAATCTAGGGGAAGGACTTCTTCTAAGACCGCTTT  7616
              || ||||||||| || |||||   |||  || ||||    ||| |    ||    ||||
Sbjct  7557  AGCAAAGGCTGTGAAGCAATTTGAGGAAAGTCAAGGCCGGACCAGTAGCAAAACAGCCTT  7616

Query  7617  CTACCAGGCTCTTCAGAACTCTCTTGGTGGAGAGGATTCTGATGCTAGAGTTGAGGCTGC  7676
             ||||||||| || |||||| || |||||||| ||| ||| |||||||  | ||||||||||
Sbjct  7617  TTACCAGGCACTGCAGAATTCTCTGGGTGGCGAGGACTCAGATGCCCGCGTCGAGGCTGC  7676

Query  7677  TGCTACTTGGTATTACTCCCTTGAGCACTCCACTGATGATTACGCTTCCTTCTCTAGGGC  7736
             ||||||| |||||||||| ||||||||||||| |||||| |  || ||||||||  ||||
Sbjct  7677  TGCTACATGGTATTACTCTCTGGAGCACTCCACGGATGACTATGCCTCCTTCTCCCGGGC  7736

Query  7737  TCTTGAGAACGCTACTAGGGACTACTTCATCATCTGCCCAATCATTGATATGGCTTCCGC  7796
             ||| ||||| |||| ||| ||||||||| ||||||||||| |  || ||  |  |||  ||
Sbjct  7737  TCTGGAGAATGCCACCCGGGACTACTTTATCATCTGCCCTATAATCGACATGGCCAGTGC  7796

Query  7797  TTGGGCTAAAAGAGCTAGGGGCAACGTTTTCATGTATCACGCCCCAGAGAACTATGGACA  7856
             ||||| |||| || ||   |  | ||||| |||||| ||||| ||  ||| ||||| ||
Sbjct  7797  CTGGGCAAAGAGGGCCCGAGGAAACGTCTTCATGTACCATGCTCCTGAAAACTACGGCCA  7856

Query  7857  TGGTTCTCTTGAGTTGCTCGCTGATGTTCAATTCGCTCTCGGACTTCCATTCTATCCAGC  7916
             |||   ||  || || |||| |||||| ||||| |||   | ||  ||||| ||||| |||||
Sbjct  7857  TGGCAGCCTGGAGCTGCTGGCGGATGTTCAGTTTGCCTTGGGGCTTCCCTTCTACCCAGC  7916

Query  7917  TTACGAGGGACAATTCTCCCCTTGAGGAAAAGTCTCTCTCCCTCAAGATCATGCAATACTT  7976
             |||| || || || ||| ||    || || || ||| | | || ||||||||||| ||||
Sbjct  7917  CTACGAGGGCAGTTTTCTCTGGAGGAGAAGAGCCTGTCGCTGAAAATCATGCAGTACTT  7976

Query  7977  CTCTCACTTCATCAGATCCGGCAACCCAAACTATCCATACGAGTTCTCTAGGAAGGTTCC  8036
             ||  |||||||||||||||  || |||||||| ||  ||||||||||| ||  |||| ||
Sbjct  7977  TTCCCACTTCATCAGATCAGGAAATCCCAACTACCCTTATGAGTTCTCACGGAAAGTACC  8036

Query  8037  AACTTTCGCTACTCCTTGGCCAGATTTCGTTCCAAGAGCTGGCGGAGAGAACTACAAAGA  8096
             ||  || || ||  ||||||| || |||||  || ||||||| ||||||||||||| ||
Sbjct  8037  CACATTTGCAACCCCCTGGCCTGACTTTGTACCCCGTGCTGGTGGAGAGAACTACAAGGA  8096

Query  8097  GTTCTCCGAGCTTCTTCCAAACAGGCAGGGACTTAAGAAGGCTGATTGCTCCTTCTGGTC  8156
             ||||     ||||| || || ||  |  || | |||| |||| || || ||||||||||||
Sbjct  8097  GTTCAGTGAGCTGCTCCCCAATCGACAGGGCCTGAAGAAAGCCGACTGCTCCTTCTGGTC  8156

Query  8157  CAAGTACATTTCTTCCCTCAAGACCTCTGCTGATGGTGCTAAGGGTGGACAATCTGCTGA  8216
             |||||||| |  || || ||||| ||||| ||||| || |||| || || || || ||||
Sbjct  8157  CAAGTACATCTCGTCTCTGAAGACATCTGCAGATGGAGCCAAGGGCGGGCAGTCAGCAGA  8216
```

Fig. 10I

```
Query  8217  GTCTGAGGAAGAGGAACTTACTGCTGGATCTGGACTTAGAGAGGATCTTCTCTCCCTTCA  8276
             |   ||| || ||||| |  || |||||||||| || ||||| ||||| ||    ||| ||
Sbjct  8217  GAGTGAAGAGGAGGAGTTGACGGCTGGATCTGGGCTAAGAGAAGATCTCCTAAGCCTCCA  8276

Query  8277  AGAGCCAGGATCTAAGACCTACTCCAAGGGAGGA*CATCACCATCACCATCACT*AA     8307
             || ||||| |||||||||||||   ||||
Sbjct  8277  GGAACCAGGCTCTAAGACCTACAGCAAGTGA                              8307
```

IMMUNOASSAY FOR DETECTING THYROGLOBULIN UTILIZING SOYBEAN PRODUCED RECOMBINANT THYROGLOBULIN

This application is a continuation-in-part and claims priority under 35 USC §371 to PCT/US2010/042248, filed Jul. 16, 2010, which claim priority under 35 USC §119(e) to U.S. Provisional Application No. 61/226,086 filed Jul. 16, 2009, and also claims priority under 35 USC §119(e) to U.S. Provisional Application 61/379,834, filed Sep. 3, 2010 the entire contents of all of which are incorporated by reference in their entireties.

BACKGROUND OF THE INVENTION

Thyroid cancers are common endocrine malignancies. One function of the thyroid gland is to store thyroglobulin as a source of thyroid hormones, and patients with thyroid cancers routinely have increased circulating levels of the thyroglobulin. Detecting increased levels of circulating thyroglobulin produced by these cancerous cells is, therefore, an extremely valuable tool for the physician in the diagnosis of thyroid cancers. Furthermore, once patients receive treatment to ablate cancerous thyroid tissue, it is important that they are monitored for any metastasized thyroid cancer remnants. Such metastases can also secrete thyroglobulin, and for these cancer survivors, quantification of thyroglobulin in sera is the gold standard for monitoring the presence of such malignant tissue. Stated simply, the quantification of thyroglobulin in the sera of patients who have, or have had, thyroid cancers is an essential tool for diagnosis and monitoring, respectively.

Thyroglobulin levels in the sera of thyroid cancer patients are routinely quantified using various agency-approved (e.g. FDA) immunoassays. Physicians frequently order these diagnostic immunoassays to determine thyroglobulin levels in their patients. Therefore it is not surprising that such a commonly ordered diagnostic test has produced a variety of immunoassays developed by many different companies for use in the clinical laboratory.

Despite the current availability of numerous thyroglobulin immuno assays each suffers from inherent limitations. In fact, it is not possible to accurately compare the results obtained from one thyroglobulin immunoassay with those obtained by another. There are two major problems which need to be solved. First, the lack of a universally consistent thyroglobulin standard contributes significantly to variability between FDA-approved immunoassays made by different suppliers. Presently, the only source of human thyroglobulin for use as a standard in immunoassays comes from cadavers or surgically removed human tissue. The heterogeneity of human-derived thyroglobulin isolates is a limitation which has not been solved. Second, anti-thyroglobulin autoantibodies present in some thyroid cancer patients' sera can interfere with immunoassays that attempt to detect and quantify thyroglobulin. Currently, there are no clear solutions to either of these dilemmas.

Human thyroglobulin is often iodinated with up to four iodine atoms (on various tyrosine residues). Defects in thyroglobulin are known to be the cause of congenital hypothyroidism due to dyshormonogenesis type 3. A disorder due to thyroid dyshormonogenesis often causes large goiters of elastic and soft consistency in most patients. Although the degree of thyroid dysfunction varies considerably among patients with defective thyroglobulin synthesis, patients usually have a relatively high serum free tri-iodothyronine (T3) concentration with disproportionately low free tetraiodothyronine (T4) levels. The maintenance of relatively high free T3 levels prevents profound tissue hypothyroidism except in the brain and pituitary, which are dependent on T4 supply, resulting in neurologic and intellectual defects in some cases.

Thus, the ability to synthesize homogenous thyroglobulin in an expression system, its use in assays, and the ability to chemically control the amount of iodination on the homogenous thyroglobulin molecules (for example by using the Iodination Beads from the Pierce Chem. Co.; see 4 and 5) could provide means of accurately comparing the results of various assays, allow the removal of autoantibodies that bind thyroglobulin allowing for more accurate diagnoses of diseases, and also potentially lead to the treatment of patients that suffer from these thyroglobulin implicated diseases with synthesized thyroglobulin conjugates.

Moreover, in an embodiment, recombinant thyroglobulin can be used as a prophylaxis therapy to prevent and/or ameliorate the host response against thyroglobulin observed in autoimmune thyroiditis in humans and animals (e.g. dogs and other animals that exhibit a host response against thyroglobulin). In a variation, the present invention can also be used in therapeutic interventions to reduce and/or eliminate the autoimmune response against thyroglobulin seen in patients and animals with autoimmune thyroiditis.

As a group, thyroid diseases are second only to diabetes as the most common endocrine disorder in the United States. Almost 100,000 new cases per year of clinically diagnosed thyroid disease occur, making the number of individuals with some clinical form of thyroid disease an estimated 4-5 million people in the United States. Hypothyroidism accounts for the majority of the cases of clinical thyroid disease in the United States and other developed countries, with autoimmune Hashimoto's thyroiditis accounting for about 80% of hypothyroiditis. Beginning in the fourth to fifth decade of life, the usual onset of autoimmune hypothyroidism is insidious, with the vast majority of cases occurring in women. Hypothyroidism results in an inadequate supply of the thyroid hormones, T3 and T4, to the body, and this deficiency can be treated using the hormone replacement drug, levothyroxine. Since hypothyroidism is a chronic disease, and since symptoms can advance with the age of the patient, replacement hormone therapy with levothyroxine can be life-long. The total U.S. market for the two leading levothyroxine products, Synthroid and Levoxyl, was 1.1 billion in 2003.

The most important limitation of hormone replacement is the fact that such therapy treats symptoms and not the cause of the disease itself. Autoimmune hypothyroidism results from the activation of helper T lymphocytes which recognize thyroid antigens (e.g. thyroglobulin) and contribute to the destruction of the thyroid gland. The presence of antibodies against thyroglobulin made by B lymphocytes may also contribute to mechanisms of thyroid destruction. Therefore, the most effective therapy for such destructive autoimmunity would be to permanently eliminate, or greatly reduce the activity of, these thyroid-reactive T and B lymphocytes in patients.

To accomplish this goal, in an embodiment, the present invention produces soybean-derived thyroglobulin that, when taken orally or systemically, has the potential to prevent and/or ameliorate the development of, or limit ongoing, autoimmune responses against thyroglobulin.

To date, there has been only limited human study to investigate the efficacy of oral immune suppressive/tolerance as a therapy for autoimmune hypothyroidism. In the one study, no substantial therapeutic value from such therapy was observed. However, the study was seriously flawed in its design.

Other groups have demonstrated that it is possible to induce suppression/tolerance with oral preparations of thyroglobulin in animals models. Therefore, while the animal studies have been encouraging, there is no clear therapeutic regimen in humans or domesticated animals for the suppression/tolerance against thyroid antigens in autoimmune thyroiditis.

Previously, in an editorial, two leaders in the field. Drs. Rapoport and McLachlan, identified major hurdles that had to be overcome before oral suppression/tolerance therapy for treatment of hypothyroidism could become a reality. These hurdles included: 1) the extreme cost associated with producing kilogram quantities of human thyroglobulin; 2) the need to identify patients with preclinical disease so that therapy could start early; and 3) the length of therapy required to maintain suppression/tolerance.

The uniqueness of soybean-derived thyroglobulin formulations can overcome these hurdles. The first hurdle can be overcome because expression of proteins in transgenic soybeans is extremely cost-effective, being less than a penny per dose to produce. The second hurdle can be overcome because the sensitivity and reproducibility of diagnostic tests (for example, as disclosed herein) for identifying patients who have preclinical hypothyroidism has progressed to the point where physicians are questioning whether or not to provide hormone replacement therapy to this ever expanding population of patients. Stated simply, it is now possible to identify preclinical patients for prophylactic therapy. The third hurdle can be overcome because while therapeutic regimens might require several weeks to demonstrate efficacy, and may have to be repeated, even such an extended treatment would be advantageous over taking daily doses of levothyroxine for a lifetime. Taken together, these technical advances should lead one to reevaluate the feasibility and practicality of oral and/or systemic suppression/tolerance therapy for autoimmune hypothyroidism.

BRIEF SUMMARY OF THE INVENTION

The present invention includes novel soybean derived human thyroglobulin, methods of producing human thyroglobulin in plants such as soybean, and novel diagnostic applications for the detection and stratification of endocrine malignancies including thyroid cancer and thyroiditis. The invention also includes the use of soybean-derived human thyroglobulin in affinity matrices to remove autoreactive anti-thyroglobulin antibodies from patient's sera prior to analyses. Moreover, in an embodiment, the present invention uses formulations of soybean-derived thyroglobulin, and/or purified soybean-derived thyroglobulin, to prevent and/or ameliorate the development of, or limit ongoing, autoimmune responses against thyroglobulin in patients and animals.

BRIEF DESCRIPTION OF THE DRAWINGS

FIG. 10 shows a comparison of nucleotide sequences between the soy-optimized hTg sequence and the wildtype hTg sequence. The soy-optimized sequence, which is SEQ ID NO: 1 is the top sequence and the wildtype hTg sequence, which is SEQ ID NO: 2 is the bottom sequence. FIG. 10A is a continuation of FIG. 10. FIG. 10B is a continuation of FIG. 10. FIG. 10C is a continuation of FIG. 10. FIG. 10D is a continuation of FIG. 10. FIG. 10E is a continuation of FIG. 10. FIG. 10F is a continuation of FIG. 10. FIG. 10G is a continuation of FIG. 10. FIG. 10H is a continuation of FIG. 10. FIG. 10I is a continuation of FIG. 10.

FIG. 13 is representative of the relative T cell responses for both wildtype and the thyroglobulin treated groups.

DETAILED DESCRIPTION OF THE INVENTION

Figure 1:
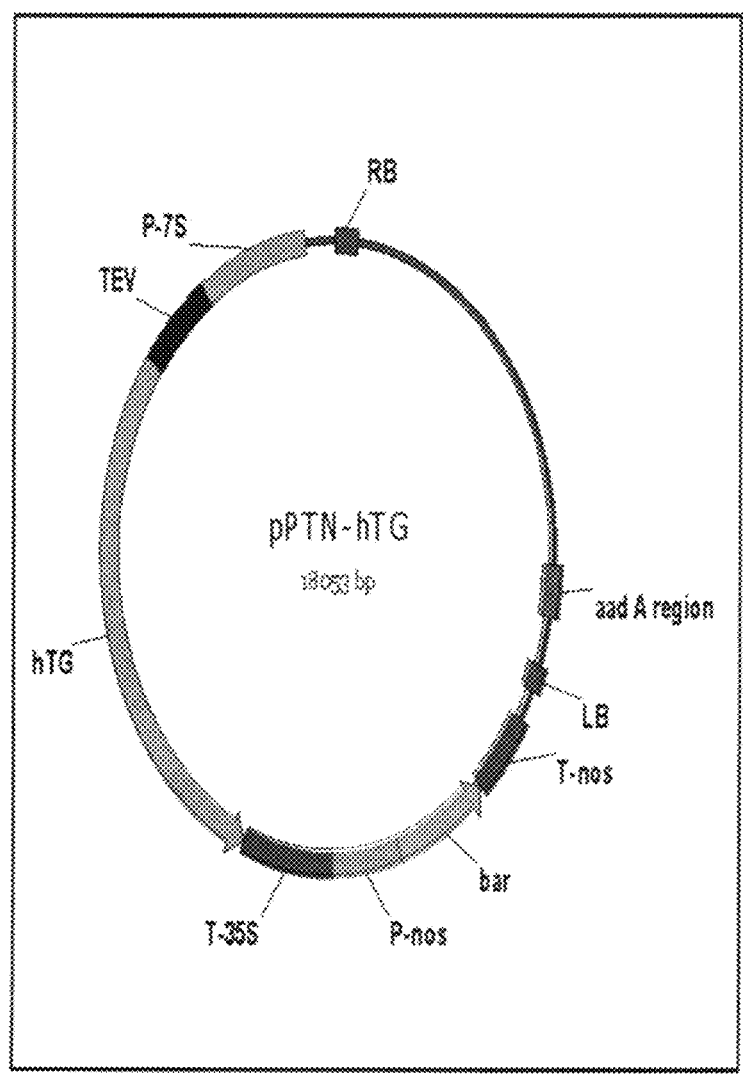
FIG. 1 shows a plant transformation vector of the present invention.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The present invention solves two of the most significant problems plaguing FDA-approved thyroglobulin immunoassays by expressing human thyroglobulin in transgenic soybean seeds. It is useful to note the unique advantages of this platform technology for recombinant protein expression.

Presently, thyroglobulin for use in immunodiagnostic assays is solely isolated from human thyroid tissue homogenates. Purification of this protein from homogenates is time consuming, and can lead to variability in composition and purity between lots [6]. The large number of contaminating thyroid proteins present in thyroid homogenates complicates the purification of thyroglobulin from this tissue.

The use of bacterial expression systems such as *E. coli* to produce human thyroglobulin cannot be utilized due to the large mass of thyroglobulin and requirement for proper post-translational modification and folding. Moreover, bacterial expression systems also generally lack the ability to glycosylate proteins which would generally preclude the use of bacterial vectors as a means of making an adequate thyroglobulin. Yeast is also not likely to be a suitable vector for the expression of thyroglobulin. Although, yeast often post-translationally modifies proteins and has the ability to glycosylate proteins, it often suffers the drawback of uneven glycosylation and poor yield.

The present invention does not suffer from these drawbacks. In contrast to the large number of proteins that are present in homogenates such as derived from the human thyroid, the number of proteins present in soybean seeds is quite limited [22]. Due to the physico-chemical characteristics of soybean proteins, purification schemes are more simple and straightforward than those currently used for human thyroid tissue. Furthermore, soybean-derived thyroglobulin was engineered to express a 6×-histidine tag (discussed in more detail below) so that affinity chromatography might be used in possible purification schemes. These inherent advantages of soybean-derived thyroglobulin will simplify its purification.

The FDA requires each lot of an analyte isolated from human tissue to be screened for the absence of transmissible agents (e.g. HIV. Hepatitis B, etc.). Since thyroglobulin is isolated from human thyroid glands, each lot must be screened for such infectious agents. This adds to the cost of production, and increases possible product liability.

Soybean-derived thyroglobulin poses no risk of spreading human transmissible diseases. The FDA will not require screening for human infectious agents which would never be present. Ultimately, this will reduce the cost of production and limit product liability.

Figure 6:
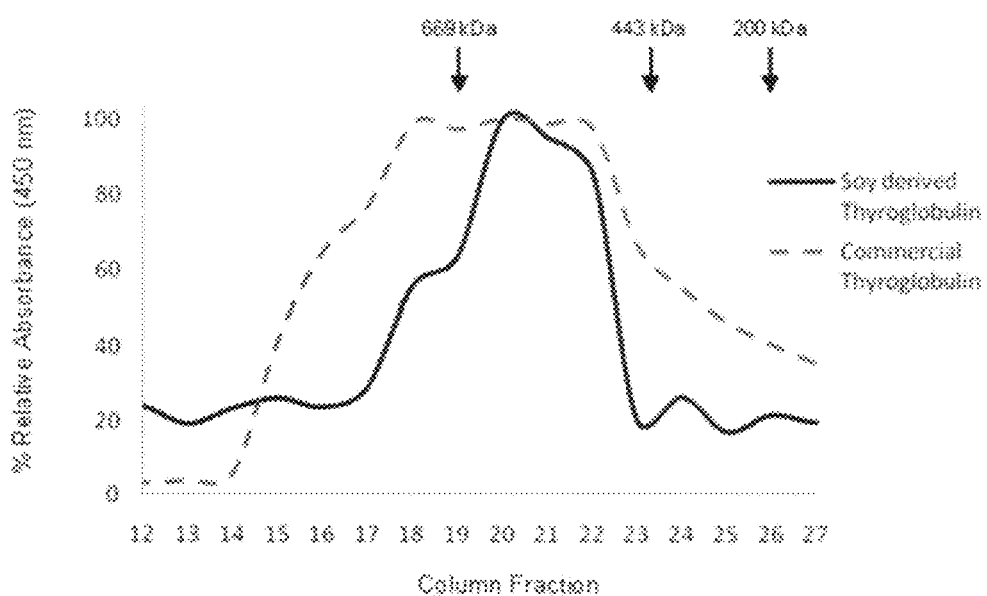
FIG. 6A represents Sephacryl S-300 HR gel filtration chromatography of soybean-derived thyroglobulin (solid line) and thyroid-purified thyroglobulin (hatched line). Fractions were collected during each gel filtration, and subjected to ELISA to detect the presence of human thyroglobulin. Results are presented as percent relative ELISA absorbance (readings at 450 nm) for fractions representing the appropriate void volumes. The peak elution volumes of a set of molecular weight protein standards used for column calibration are indicated.
FIG. 6B shows a western analysis of eluted fractions. Equal amounts of protein from the indicated fractions were separated in 5% native gels and subjected to western analysis. The location of the dimeric (D) form of hTG is indicated by the arrow.
Figure 6:
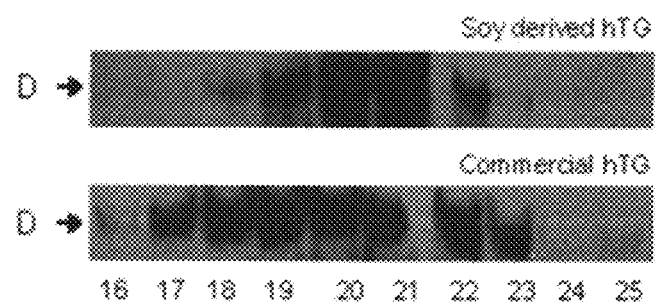

One problem with thyroglobulin isolated from human thyroids is its heterogeneous nature. Since thyroid glands contain "immature" and "mature" forms of thyroglobulin that vary significantly in glycosylation and iodination, different lots of thyroglobulin can be quite dissimilar in purity and composition. This fact is borne out in some of our results where thyroglobulin isolated from human thyroid glands runs as a relatively broad peak on molecular sizing chromatography columns (see FIG. 6).

Soybean-derived thyroglobulin of the present invention is much more homogenous than thyroid-isolated thyroglobulin for the following reasons. First, soybeans do not contain enzymes for iodination, therefore all soybean-derived thyroglobulin will have no iodine present. This represents a significant advantage since all thyroglobulin molecules will be homogenous relative to iodine content. This will allow non-iodinated lots of purified thyroglobulin to be produced. In addition, simple and straightforward iodination reactions (e.g. Iodination Beads, Pierce Chem. Co.) can be carried out on lots of thyroglobulin to produce uniformly iodinated protein of the different thyroglobulin molecules if needed. For example, the treatment of non-iodinated thyroglobulin with the correct molar ratio of iodine and the correct oxidizing conditions will lead to a uniform amount of the T3 (or the T1, T2, or T4) isomer. This flexibility will allow "custom" iodination of soybean-derived thyroglobulin as needed for various applications.

Second, proteins within soybean seeds are uniformly glycosylated. Since the soybean seed has a protein storage function, the proteins present in seeds are "mature" with uniform glycosylation [22]. This property will also contribute to the homogenous nature of soybean-derived thyroglobulin. While soy protein glycosylation will differ from human, the antibodies used in FDA approved ELISAs recognize the protein backbone, not carbohydrate residues. The uniform glycosylation of soybean-derived thyroglobulin will contribute to overall protein homogeneity, but not affect the ability of antibodies to bind this protein.

Soybean-derived thyroglobulin will provide an improved, "reference" standard for quantification of this protein using FDA approved ELISAs when compared to thyroid-purified thyroglobulin.

Presently, the transgenic soybean lines of the present invention express up to ~1% of their total soluble protein as thyroglobulin. With the screening of additional transgenic soybean lines, it may be possible to identify higher expressers. Regardless, a soybean seed weighs approximately 150 milligrams and contains approximately 40% protein (i.e. 60 milligrams of total protein per seed). At 1% expression, this represents 0.6 milligrams of thyroglobulin per seed. A single acre of soybeans could therefore produce approximately 10 kilograms of thyroglobulin at less than 0.01 cents per milligram using conventional methods. Even when considering growth in Biosafety Level 2 greenhouses, the cost increase for production will be approximately 20 fold (i.e. less than 2 cents per milligram) [23].

Production of proteins in transgenic soybean seeds can be considered a "green" technology as the growth of these plants consumes $CO_2$ and releases $O_2$. Conversely, other expression systems (e.g. E. coli) consume $O_2$ and produce toxic byproducts requiring disposal.

Soybean seeds are comprised of ~40% protein and therefore represent an ideal avenue for transgenic protein production. Moreover, at expression levels of ~1%, it will be possible to contain the growth of transgenic soybeans in Biosafety Level 2 greenhouses without the need to produce in open fields [23]. At production levels of 10 kilograms per acre, and with the potential for 3 growing seasons per year, there would be no need for expansive open field plantings. Secure greenhouse growth would provide containment, and be consistent with good manufacturing practices for production of an FDA approved analyte.

Much of the thyroglobulin isolated from human thyroid cadaver or surgical tissue and used in diagnostic assays comes from foreign suppliers (e.g. B.R.A.H.M.S., Berlin, Germany; Cis Bio International, Gif-sur-Yvette, France; Iason, Graz-Seiererg, Austria; Orgentec, Mainz, Germany). Therefore the ability to produce thyroglobulin in transgenic soybean seeds in the United States would reduce dependence on foreign suppliers.

Non-Limiting Examples and Implementation of the Present Invention

Expression of the Full Length Human Thyroglobulin Gene in Transgenic Soybean Seeds Human thyroglobulin is encoded by an 8.3 kb mRNA species encoding 2767 amino acids with a molecular weight of the mature monomer being over 300,000 daltons [4, 5]. Thus, thyroglobulin is a very large protein which presents some significant challenges when trying to express this protein using traditional expression systems (e.g. E. coli) and it has been difficult (if not impossible) to accomplish. Yeast has also been used as a recombinant expression system. However, variations in glycosylation in yeast have been an obstacle that has often led to decreased yields and to the inventor's knowledge, yeast has not been capable of expressing thyroglobulin. One function of the thyroid gland is to store thyroglobulin [4,5]. In this sense, the thyroid gland is a storage organ. Soybean seeds also function to store proteins needed for germination.

Design of Thyroglobulin Nucleotide Sequence

A soybean compatible version of full-length human thyroglobulin was designed using criteria described in the art [24, 25]. This "planticized" version of the human thyroglobulin gene was modified to optimize its expression in transgenic soybeans; however, it should be noted that the protein sequence encoded by this synthetic gene is identical to that of the human protein sequence. It was necessary to modify the nucleotide sequence, while keeping the encoded amino acids the same, to permit the soybean seeds to express optimal levels of this protein.

Because human Thyroglobulin (hTg) is made in the endoplasmic reticulum (ER), and is heavily glycosylated, and is secreted, it was postulated that the synthetic version should also be translated by the rough ER, but not retained there. An assumption is that the endogenous leader should target hTg to the proper location for translation, so the synthetic gene was designed with an intact leader sequence. It was also expected that the leader would be cleaved by the soy plant machinery. It was postulated that no KDEL (lys-asp-glu-leu) sequence SEQ ID NO: 37 (the most common endoplasmic retention sequence) should be required, as one is not present in the wild type human version. It was also postulated that the cloned synthetic gene could be placed downstream of the 7S promoter and fused to a translational enhancer sequence (e.g. TEV, Tobacco Etch Virus). To aid in purification, it was postulated adding a His tagged linker (and thus, the His tag was added) at the C-terminus. Other amino acid sequences to aid in purification (and placed at either the N-terminus or C-terminus) were contemplated, such as GST tags, FLAG tags, HA tags, and MYC tags. It is also postulated that biotin-strepavidin chemical tags can be used to aid in the purification process. The amino acid sequence of the expressed gene was cross checked against the updated sequence in the prior art [4]. In all cases where van de Graaf noted polymorphic variability, the second amino acid was chosen, except for 1819D and 2511R. The inventors postulated and used 5' NcoI and 3' XbaI for cloning. The inventors did not use the TGA for the stop codon as the inventors knew that the overlapping methylation would prevent XbaI digestion. Moreover, the wobble position of each codon was often changed to make the sequence more amenable to expression in soybean. Generally, the nucleotide sequence that is optimized for soy tends to contain a lower GC content than the corresponding wildtype human thyroglobulin.

Synthesizing Nucleotide Sequence

The nucleotide sequence was synthesized using standard nucleotide synthetic techniques by GeneArt (Burlingame, Calif.) employing the strategy outlined above. A comparison between the open reading frame of wildtype thyroglobulin and the nucleotide sequence used for the soybean transformed thyroglobulin is shown in FIG. 10. In FIG. 10, the top sequence (query) represents the soy-optimized hTG and the wildtype human hTG is the bottom sequence (Sbjct). The top sequence representing the soy-optimized hTG is also SEQ ID NO: 1. The bottom sequence representing wildtype hTG is SEQ ID NO: 2. There was sequence homology in the nucleotide sequences in 6325 of the 8311 nucleotides for a sequence homology percentage of 76%.

Wildtype human thyroglobulin has a plurality of exon regions (at least 48) that are post-translationally excised out. The soy-optimized SEQ ID NO: 1 was compared to the open reading frame of the wildtype thyroglobulin because it (i.e. SEQ ID NO: 2) (a) does not contain the exon sequences, (b) was recently updated to correct nucleotide errors and omissions, and (c) represented a consensus from a large number of individual sequences. Moreover, one should note the His tag (a plurality of CAT codons) at the 3' end of the nucleotide sequence in SEQ ID NO: 1 (i.e., the top sequence in FIG. 10). The His tag allows purification of the soy-optimized thyroglobulin by using a $Ni^+$ column or any other column that is able to preferentially bind a series of histidine residues.

Transformation

The synthetic hTG gene was designed and engineered as above to contain a native signal sequence, a GC content representative of plant systems, and codons that were optimized for expression in the *Glycine max* system. The synthetic hTG was subcloned downstream of the soybean β-conglycinin promoter resulting in the binary vector pPTN-hTG as shown in FIG. 1. In addition to the hTG (synthetic human thyroglobulin gene), the expression cassette was designed to contain P-7S (the soybean β-conglycinin promoter), TEV (tobacco etch virus translational enhancer element), and T-35S (cauliflower mosaic virus terminator element). The plant selection cassette contained P-nos (nopaline synthase promoter), Bar (phosphinothricin acetyltransferase gene for plant selection), and T-nos (nopaline synthase terminator element). Both cassettes were placed between the RB (right border sequence) and LB (left border sequence), in a binary vector that contained the aad A region (streptomycin resistance gene for bacterial selection).

Soybean transformation using the *Agrobacterium*-mediated half seed method was performed as described in Paz et al (30). Briefly, half-seed explants (*Glycine max*) were dissected and inoculated with *Agrobacterium* suspension culture (strain EHA101 carrying various binary vectors). The inoculated explants were placed adaxial side down on cocultivation medium at 24° C. and under 18:6 photo period for 3-5 days. After cocultivation, explants were cultured for shoot induction and elongation under glufosinate selection (8 mg/L) for 8-12 weeks. Herbicide resistant shoots were harvested, elongated and rooted as described (30). Acclimated plantlets were transferred to soil and grown to maturity in the greenhouse. Transformation resulted in a total of five independent glufosinate-resistant events.

Figure 11:
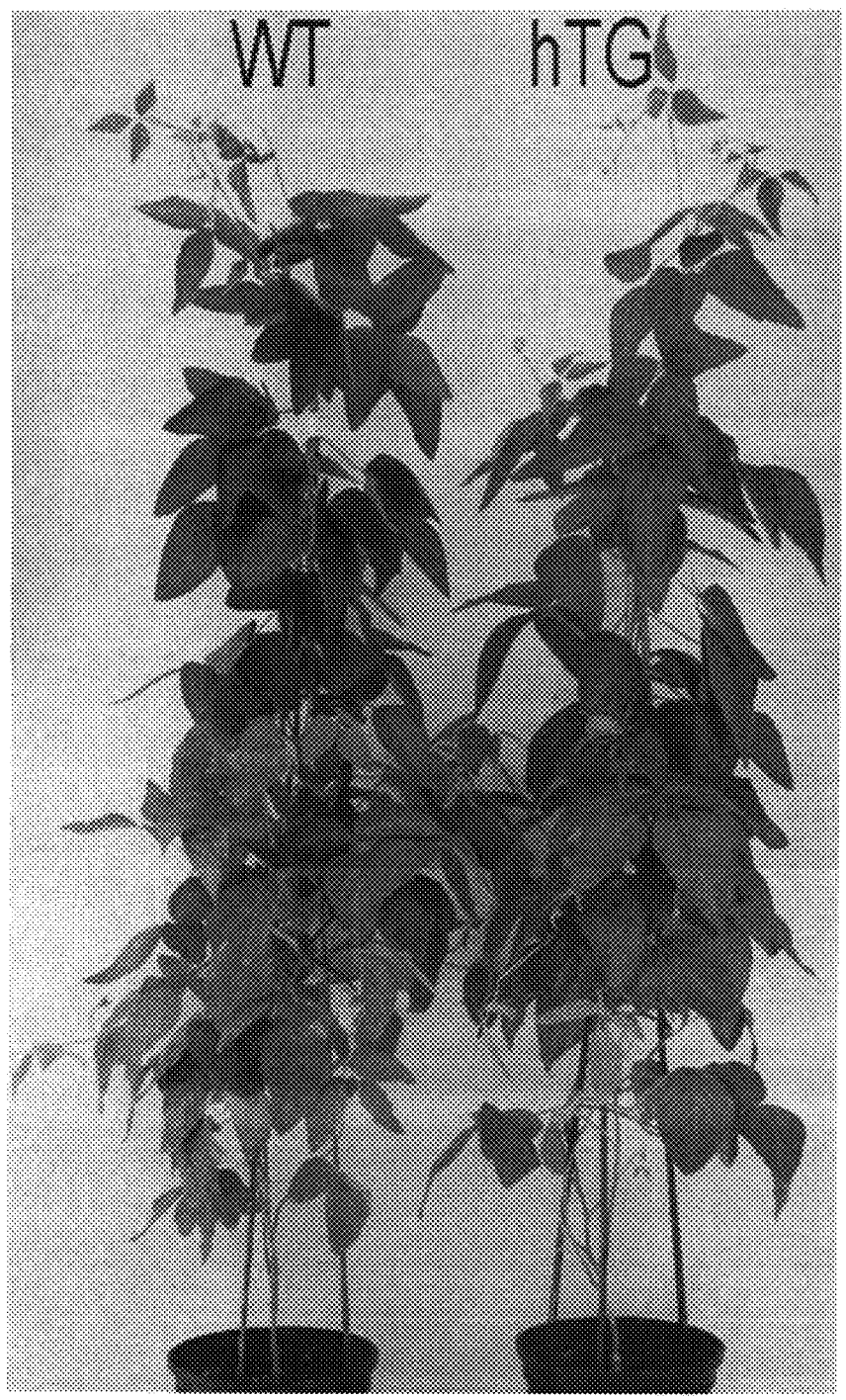
FIG. 11 shows a wildtype plant adjacent to the transformed plant containing the expressed thyroglobulin gene.

*Agrobacterium*-mediated transformation resulted in five independent T0 lines designated 77-3, 77-4, 77-5, 77-7 and 77-12. Phenotypically, T0 parent plants as well as T1 and T2 progeny plants all appeared similar to wild type nontransgenic control plants with respect to leaf color, growth habit and relative seed yield (see FIG. 11). 60-day old transgenic (line 77-5) and WT (control) plants are shown in FIG. 11. To monitor for expression of the glufosinate herbicide selectable marker, T1 and T2 plants were sprayed with Ignite 280 SL herbicide (Bayer CropScience, RTP, NC) at a concentration of 80 mg/l for a total of three times (days 1, 3, and 5). Plants with visible chlorosis similar to that observed in nontransgenic plants were scored as negative for resistance to the herbicide and discarded, while positive plants were taken to maturity. Plants known to be resistant to phosphinothricin were included as a control for spray concentration and application.

Figure 2:
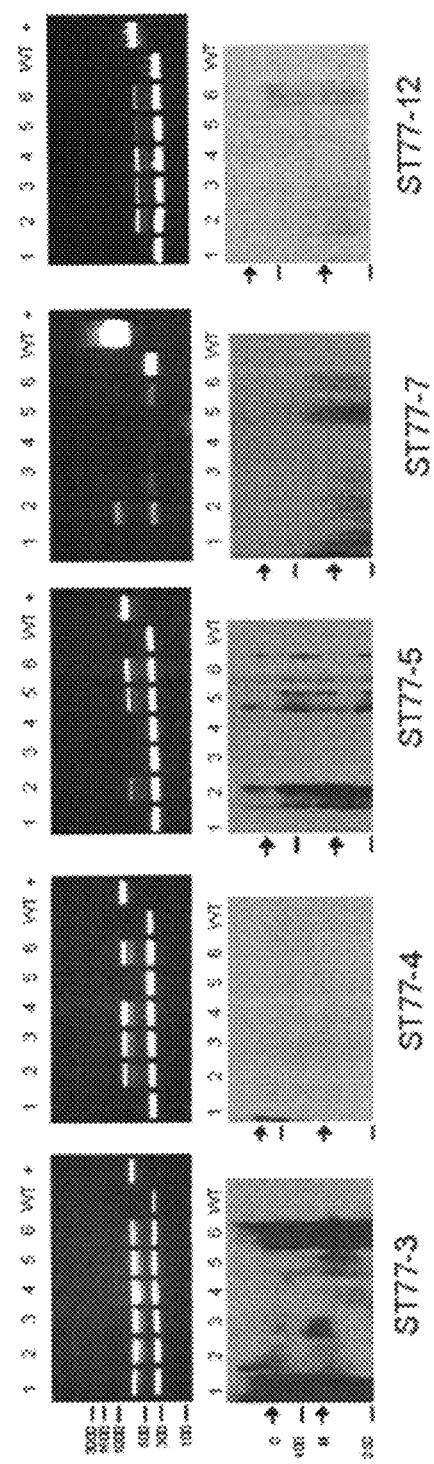
FIG. 2 illustrates PCR amplification of thyroglobulin DNA from other transgenic soybean seeds.

Individual T1 seeds were harvested from several surviving plant lines, and were screened for the presence of human thyroglobulin. First, genomic DNA was isolated from individual T1 seed shavings and from control seeds. In particular, genomic DNA was prepared from cotyledon tissue using the Maxwell 16 Instrument and Maxwell Tissue DNA Purification Kit (Promega, Madison, Wis.). Soybean genomic DNA (100 ng), TG primers (forward: 5'-GCT-CAACCACTTAGACCATGCGA-3'; reverse: 5'-TCA-GCGCAGTGGCAATATCCTG-3'), vsp primers (forward: 5'-GCTTCCACACATGGGAGCAG-3'; reverse: 5'-CCTCTGTGGTCTCCCAAGCAG-3', SEQ ID NOs: 33-36, respectively), and dNTPs were mixed with GoTaq Flexi DNA with GoTaq Flexi DNA polymerase and buffer (Promega Corp., Madison, Wis.) according to the manufacturer's directions. Following an initial denaturation cycle (5 minutes at 94° C.) the reactions were subjected to 38 cycles comprised of denaturation (30 seconds at 94° C.), annealing (45 seconds at 58° C.) and extension (60 seconds at 72° C.). PCR products were visualized in 1.0% agarose gels stained with ethidium bromide. The DNA from the individual soybean seeds of the indicated transgenic lines were isolated and analyzed by PCR to detect the presence of the integrated T-DNA (e.g. hTG). The plasmid DNA (pPTN-hTG) used for soybean transformation served as a positive control (+). FIG. 2 shows the results of various analyses. In FIG. 2, molecular characterization of six individual T1 progeny derived from each parent line are shown. In the top panels the following are shown: Agarose gel (1%) showing results from duplex PCR used to detect vegetative storage protein (vsp, internal control) and hTG sequences in genomic DNA isolated from T1 seed chips. Amplified PCR products diagnostic of vsp and hTG migrate at ~325 bp and ~659 bp, respectively. Genomic DNA from control reactions are designated "WT" (wild type, nontransgenic) and "+" (plasmid pPTN-hTG). The designations for molecular weight markers are shown in base pairs. In the bottom panels, the following are shown: a western analysis of T1 crude seed proteins separated in 5% native polyacrylamide gels. The migration of 250 kDa and 400 kDa proteins used as visual standards is shown. The arrows represent the locations of monomeric (M) and dimeric (D) forms of hTG as visualized in western blots by inclusion of an hTG standard (75 ng of commercially-purified hTG) run on each gel.

Soybean-Derived Thyroglobulin Protein is Recognized by Commercially Available ELISAs To begin to evaluate thyroglobulin protein expression by transgenic soybean seeds, two different commercially available ELISAs and one designed by the inventors were used. All of these ELISA use pairs of antibodies in a capture/detection format.

Figure 4:
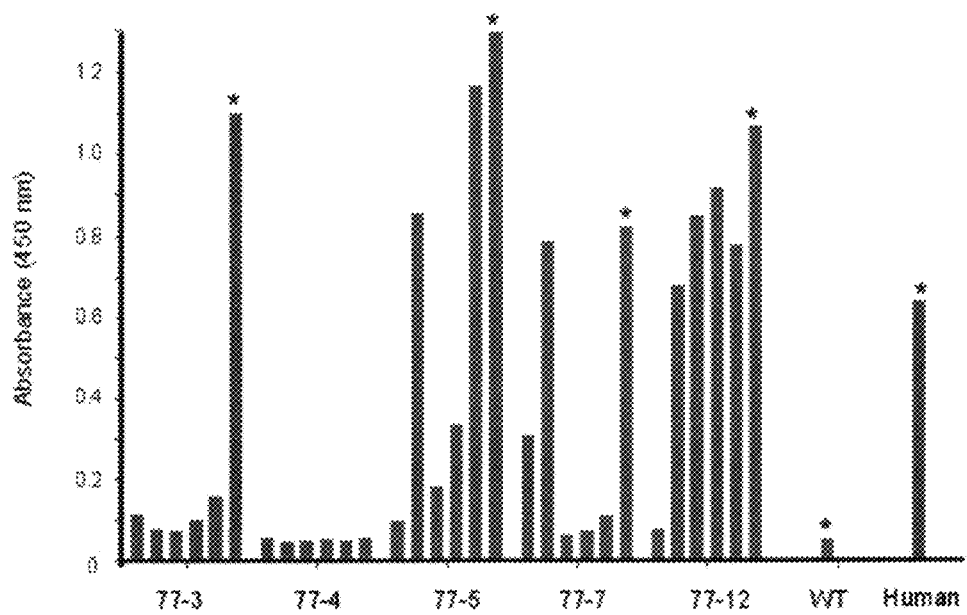
FIG. 4 presents an ORGENTEC thyroglobulin ELISA of total soluble protein isolated from the indicated transgenic soybean lines. Each number represents an isolate from an individual soybean seed from that particular line. Results are presented as mean absorbance values. Wild type (WT) soluble soybean protein was used as a negative control (−). The positive control (Human) represents human-purified thyroglobulin (Calbiochem) which was added to wild type soluble soybean protein.

In the first ELISA, the total soluble protein was isolated from 6 different individual T1 seed shavings from 5 different transgenic soybean lines. In particular, seed chips (~10 mg of cotyledon tissue) were resuspended in 150 µl of phosphate buffered saline (PBS) and sonicated for 30 seconds using a Vibra-Cell ultrasonic processor (Newton, Conn.). Samples were clarified from insoluble debris by centrifugation at $16.1 \times 10^3$ g at 4° C. Total soluble protein was quantified with the Bradford Reagent (Bio-Rad, Hercules, Calif.) using bovine serum albumin (BSA) as a standard. These soluble protein isolates were then assayed several ways using two commercially available ELISA. One ELISA from Orgentec (Orgentec. Mainz. Germany) was used to detect the presence of human thyroglobulin. FIG. 4 shows the results of one such assay from the Orgentec assay. It was clear from this ELISA that seeds from 4 of the 5 lines tested contained immunoreactive-thyroglobulin (line 77-4 did not contain the immunoreactive-thyroglobulin). The fact that this ELISA detected human thyroglobulin in sera strongly suggested that these particular transgenic soybean seeds expressed this protein.

The commercially available ELISA from Orgentec uses polyclonal anti-human thyroglobulin antibodies to capture and detect human thyroglobulin. Such polyclonal antibodies likely bind both linear and conformational epitopes along the length of the thyroglobulin molecule.

A more stringent test to evaluate the nature of soy-derived thyroglobulin would be the use of a second ELISA procedure which utilizes monoclonal antibodies for capture and detection, respectively. The commercially available ELISA produced by Kronus, Inc. (Boise, Id.) is such an assay, and employs monoclonal antibodies which can simultaneously recognize two different conformational determinants on human thyroglobulin. This assay was used to detect the presence of thyroglobulin in selected soy protein samples that were identified as expressing this protein in FIG. 4 above.

Figure 5:
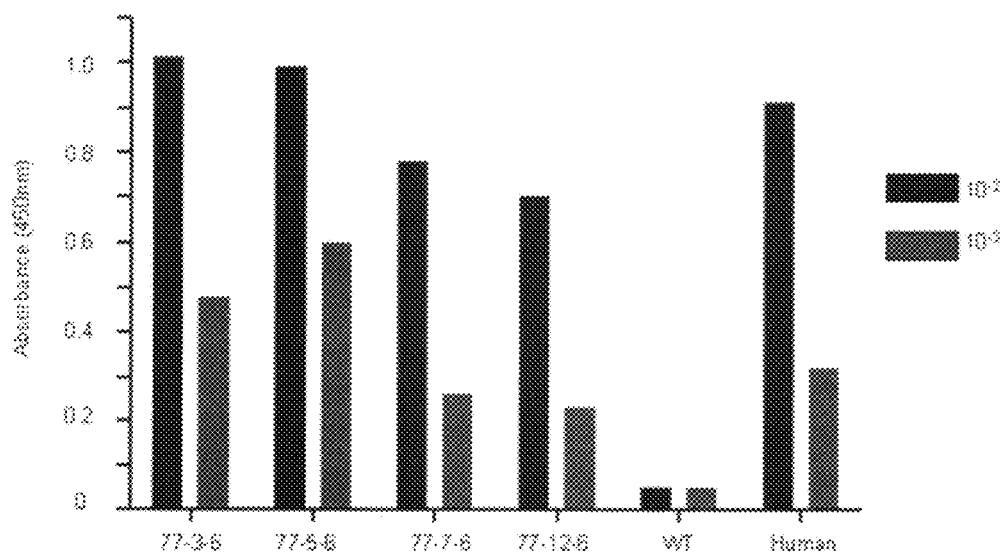
FIG. 5 shows KRONUS thyroglobulin ELISA of total soluble protein isolated from the indicated transgenic soybean lines. Each number represents an isolate from an individual soybean seed from that particular line. Results are presented as mean absorbance values showing two different dilutions of soluble protein (i.e., 1:100 and 1:1000) from each seed. Wild type (WT) soluble soybean protein was used as a negative control (−). The positive control (+) represents human-purified thyroglobulin (Human) which was added to wild type soluble soybean protein.

The Organtec ELISA uses polyclonal antibodies for detection of thyroglobulin. A second commercially-available kit for detecting thyroglobulin is the Kronus ELISA. While the Orgentec kit uses two polyclonal antibodies for detection, the Kronus kit utilizes separate monoclonal antibodies for detection. FIG. 5 shows the results of one such assay. It was clear from this ELISA that the seeds tested contained immunoreactive-thyroglobulin. The fact that this ELISA uses two monoclonal antibodies to capture and detect thyroglobulin provides further support for the authenticity of soybean-derived thyroglobulin.

In particular, FIG. 5 shows the Kronus ELISA used for detection of hTG in select T1 seed extracts. Crude seed extract from one representative T1 progeny (indicated by an asterisk in FIG. 4) was examined, along with soluble protein from a nontransgenic seed (WT) and commercially-purified hTG. Five different dilutions of each selected sample were tested in the ELISA and absorbance values for two of these dilutions (1:100 and 1:1000) are shown along with controls for comparison.

A third sandwich-based ELISA was developed and this ELISA utilized a monoclonal antibody for capture and a polyclonal antibody for detection. Briefly, 500 ng of capture antibody (GTX21984, GeneTex, Irvine, Calif.) was coated onto ELISA plates by incubation at 4° C. for 16 hours. Unbound antibody was washed with PBS and nonspecific binding sites were blocked by incubation with 1% BSA in PBS for 1 hour at 23° C. Soy protein samples and the hTG standard were then loaded onto plates and allowed to complex with the bound antibody for 2 hours at 23° C. Unbound products were washed and a rabbit polyclonal detection antibody (GTX73492, GeneTex, Irvine, Calif.) was allowed to bind to the antigen for 2 hours at 23° C. The secondary antibody was subsequently detected using a goat anti-rabbit IgG-HRP antibody (sc2004. Santa Cruz Biotechnology, Santa Cruz, Calif.) by incubation for 1 hour at 23° C. The antibody-antigen complexes were incubated with TMB Substrate (BioFX, Owings Mills, Md.), and colorimetric reactions were stopped by the addition of 0.6 M sulfuric acid. Absorbance values were read at 450 nm and confirmed the results of the two commercial assays. The fact that separate monoclonal antibodies reacted with the soy-derived transgenic protein, along with the fact that two separate commercial kits detected seed-specific immunoreactive proteins, provided further support for the authenticity of recombinant hTG protein.

Sephacryl S-300 HR Gel Filtration Chromatography of Soybean-Derived Thyroglobulin To begin a physico-chemical characterization of soybean-derived thyroglobulin, gel filtration chromatography (size exclusion chromatography) was used on total soluble protein isolated from ELISA-positive seeds. A Sephacryl S-300 HR gel filtration column (bed height 72 cm) was calibrated with molecular weight standards by monitoring absorbance at 280 nm (BioLogic LP, BIO-RAD, Inc.).

Next, total soluble protein isolated from ELISA-positive seeds was then applied to this gel filtration column. Protein elution was monitored and individual fractions of separated protein were collected.

Similarly, human thyroid-purified thyroglobulin (Calbiochem. Inc.) was diluted in 0.5 ml of wild type soy protein, and applied to the same column. Eluted fractions were also collected.

Eluted fractions were then subjected to ELISA (Orgentec) to detect the presence of immunoreactive thyroglobulin in each fraction. Immunoreactive profiles for human thyroid-purified thyroglobulin and soybean-derived thyroglobulin were similar by comparison. Thyroglobulin is approximately 330 kDa as a monomer, but exists in solutions as a 660 kDa dimer. Therefore it was of interest to determine whether soybean-derived thyroglobulin could also form dimers. Both thyroglobulin protein preparations had a peak elution volume similar to that observed for bovine thyroglobulin (at 669 kDa). In fact, it appears that soybean-derived thyroglobulin was somewhat more homogenous in its elution profile than that observed for human thyroid-purified thyroglobulin (as the peak is sharper—see FIG. 6A). More importantly, it was clear from these studies that soybean-derived thyroglobulin could form ~660 kDa dimers, strongly suggesting that this protein folds in a manner similar to thyroid-isolated human thyroglobulin, allowing dimer formation.

Gel filtration chromatography and Western blot analysis of soybean-derived thyroglobulin and thyroid purified thyroglobulin.

Quantification of recombinant protein in seed extracts:

In another embodiment, a sephacryl S-300 HR gel filtration column (bed height 72 cm) was calibrated by determining the peak elution volumes (absorbance at 254 nm, Bio-Logic LP, BIO-RAD. Inc.) of a set of molecular weight protein standards (Sigma. Inc.). Crude, total soluble protein was then isolated from hTG-positive seeds, and applied to a gel filtration column, and eluted fractions were collected. Similarly, human thyroid-purified thyroglobulin was applied to the same column, and eluted fractions were also collected.

Eluted fractions were then subjected to ELISA (Orgentec) to detect the presence of immunoreactive thyroglobulin in each fraction.

Based on gel filtration chromatography it was clear that soybean-derived thyroglobulin could form 660 kDa dimers (see FIG. 6B). This result suggested that monomers would have a size of approximately 330 kDa. To prove this possibility, protein extracts from transgenic and wild type seeds were run in 5% native polyacrylamide gels for approximately 2 hours at 110V. Unless noted, neither the gel, sample buffer nor running buffer contained β-mercaptoethanol or SDS, and samples were not boiled prior to loading onto the gel. Purified hTG (EMD Chemicals, Gibbstown, N.J.) was included as a standard. Following electrophoresis, gels were equilibrated in 1×N-cyclohexyl-3-aminopropane-sulfonic acid buffer at (pH 11) with 10% methanol for 10 minutes and transferred to Immobilon-P membrane (Millipore, Billerica, Mass.). Membranes were blocked overnight with 5% nonfat milk in PBS solution at 4° C., incubated with rabbit anti-hTG polyclonal antibody (Gene Tex Inc., Irvine, Calif.) for 3 hours at 23° C., and washed three times (10 minutes each) with PBS containing 0.05% Tween. Membranes were then incubated with goat anti-rabbit HRP (horse radish peroxidase)-conjugated IgG (Santa Cruz Biotechnology, Santa Cruz, Calif.) for 30 minutes at 23° C. and washed. Detection was carried out using the SuperSignal West Pico substrate (Thermo Scientific, Rockford, Ill.).

Alternatively, gel filtration chromatography was used as shown in FIG. 6A to partially purify proteins from crude soluble seed extracts. A Sephacryl S-300 HR gel filtration column was calibrated by determining the peak elation volumes of a commercial set of molecular mass standards ranging in size from 669 kDa to 29 kDa. The largest of these molecular mass standards was bovine thyroglobulin (MW~669 kDa) and eluted in fraction 20. β-amylase is the standard at 443 kDa and alcohol dehydrogenase is the standard at 200 kDa. Following calibration, transgenic seed extract from line 77-5 was applied to the Sephacryl column, and the eluted protein in each fraction was subjected to an ELISA for detection of hTG. The immunoreactive profile for soy-derived hTG is shown as a solid line in FIG. 6A. Although fractions 17-23 contained detectable levels of hTG, the peak immunoreactivity was localized to fractions 20 and 21. Fractions 1-11 and 28-36 showed minimal absorbance and therefore are not included on the plot in FIG. 6A. The elution profile for soy-derived hTG was consistent with the elution of the bovine thyroglobulin standard in fraction 20, suggesting that seed-specific hTG is likely folded and charged in a manner similar to that of the bovine thyroglobulin marker. For comparison, commercially purified hTG was also chromatographed on a Sephacryl column and fractions were similarly assayed for immunoreactivity. These results are plotted as a dashed line in FIG. 6A. The elution profile of commercially-purified hTG suggests that this protein is more heterogeneous than soy-derived hTG since high levels of immunoreactivity were detected in a broad peak throughout fractions 18-22. These results also suggest that purified hTG is slightly heavier than soy-derived hTG, consistent with the likely iodination of the human sample but not the soy-derived sample.

Western analysis was performed to visualize immunoreactive protein in the eluted fractions. Equivalent volumes of partially-purified seed protein and commercially-purified hTG were separated in native polyacrylamide gels and subjected to western analysis. FIG. 6B shows that eluted fractions containing peak ELISA immunoreactivity also contained the greatest level of 660 kDa dimer in western experiments. Equal amounts of protein from the indicated fractions were separated in 5% native gels and subjected to western analysis. As expected, the migration of soy hTG in extracts following partial purification was analogous to that of the commercially purified hTG, further demonstrating the molecular similarities of both proteins when characterized under a variety of sizing and separating conditions. The location of the dimeric (D) form of hTG is indicated.

Confocal Microscopy

Figure 3:
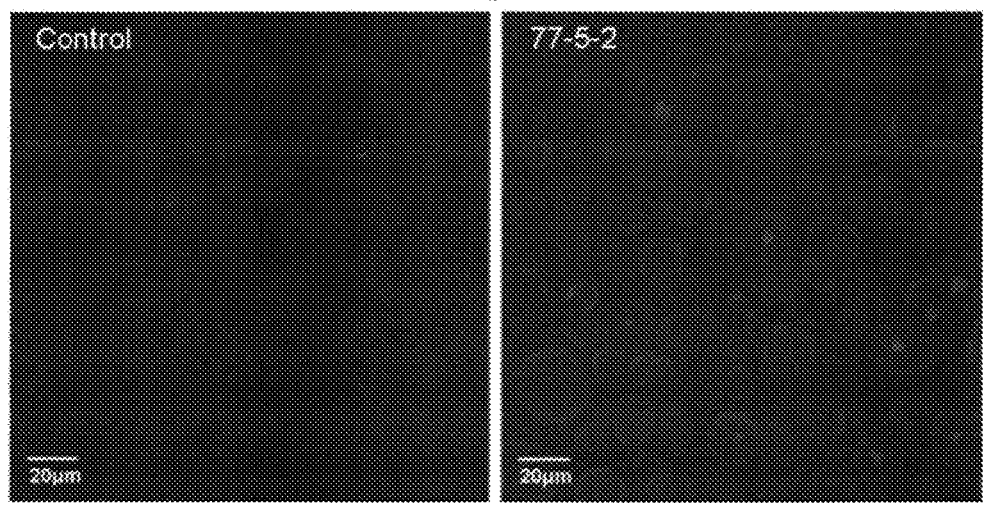
FIG. 3 represents two confocal images; one a control and the other demonstrating hTG accumulation in transgenic T1 cotyledon tissue.

FIG. 3 shows the results of confocal microscopy which was performed as follows. Whole seed tissue was imbibed for 16 hours in 1×PBS and the seed coat was removed. Tissue was fixed as described previously by our laboratory (25, 31). Briefly, sections were permeabilized with 1×PBS containing 0.2% Tween for 10 minutes, and nonspecific binding was blocked by incubation with 1×PBS supplemented with 3% BSA for 4 hours at 23° C. Tissue was incubated with rabbit anti-hTG serum (1:20 dilution) for 16 hours at 4° C. followed by incubation with an AlexaFluor 594 goat anti-rabbit IgG-HRP conjugated secondary antibody (1:200 dilution) for 1 hour at 23° C. Finally, tissue was incubated with 4,6-diamidino-2-phenylindole (DAPI; 1:500 dilution) for 5 minutes. Cover slips were added to the sections using Gel/Mount aqueous mounting media. Images were collected with a LSM 710 Spectral Confocor 3 Confocal Microscope (Carl Zeiss, Inc.) using a 40× objective and a 405 nm laser to visualize DAPI stained nuclei, along with a 561 nm laser to collect emitted fluorescence from the Alexafluor 594 antibody. Stacks of images (30 optical sections, 17 nm apart) were collected in the Z plane of the specimens and projected to form a single image. To improve clarity and reproduction quality, image colors were proportionally enhanced using the ZEN 2009 Light Edition software.

In FIG. 3, the lighter color (shows as blue if image is in color) at the nuclei of the cells represents DAPI staining while the lighter color (shows as red if image is in color) on the outer surface of the cells represents fluorescence from the AlexaFluor antibody recognizing transgenic hTG.

Figure 7:
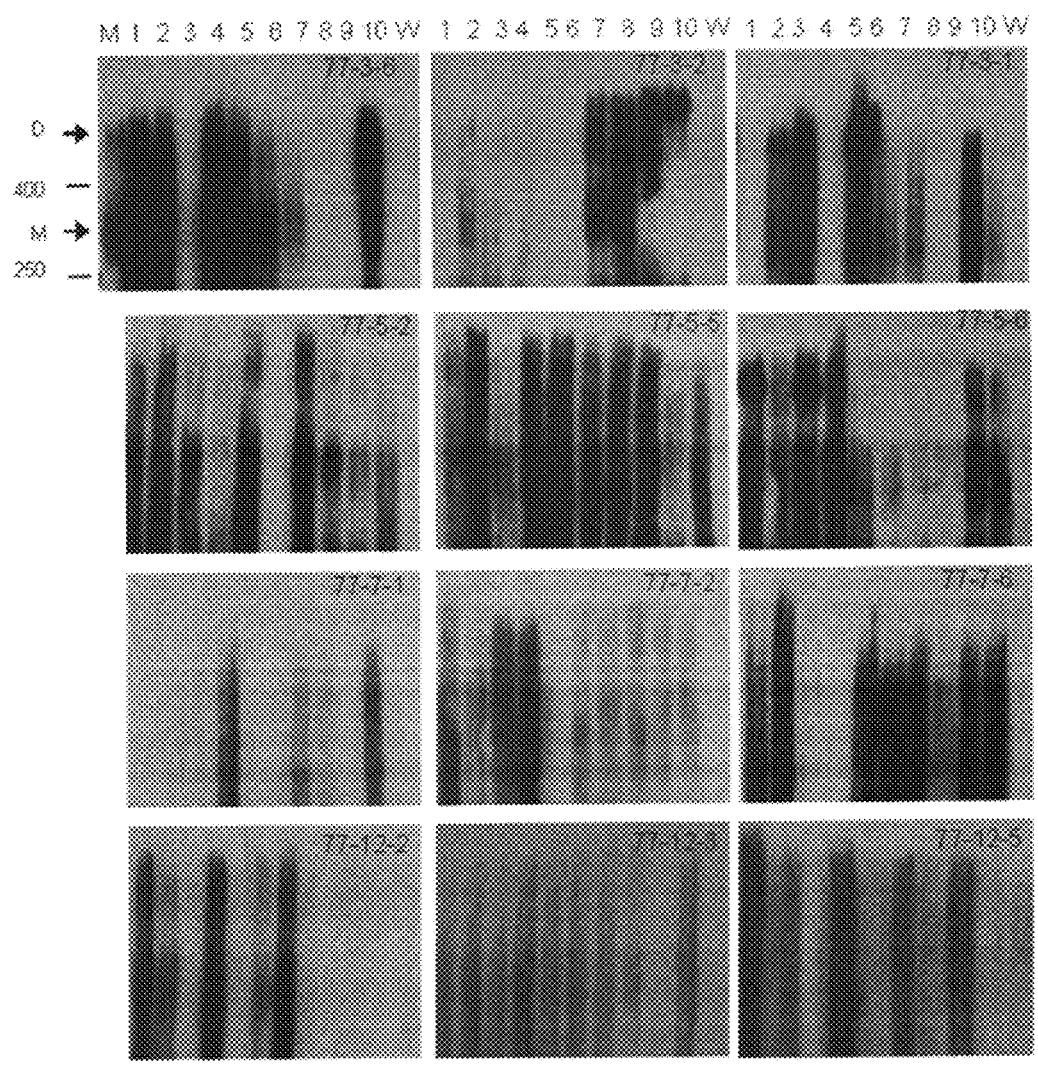
FIG. 7 shows a Western analysis of T2 seed protein. The crude seed extracts (5 μg) from 10 random T2 progeny were separated in 5% native polyacrylamide gels and screened by western blot analysis for the presence hTG.
Figure 8:
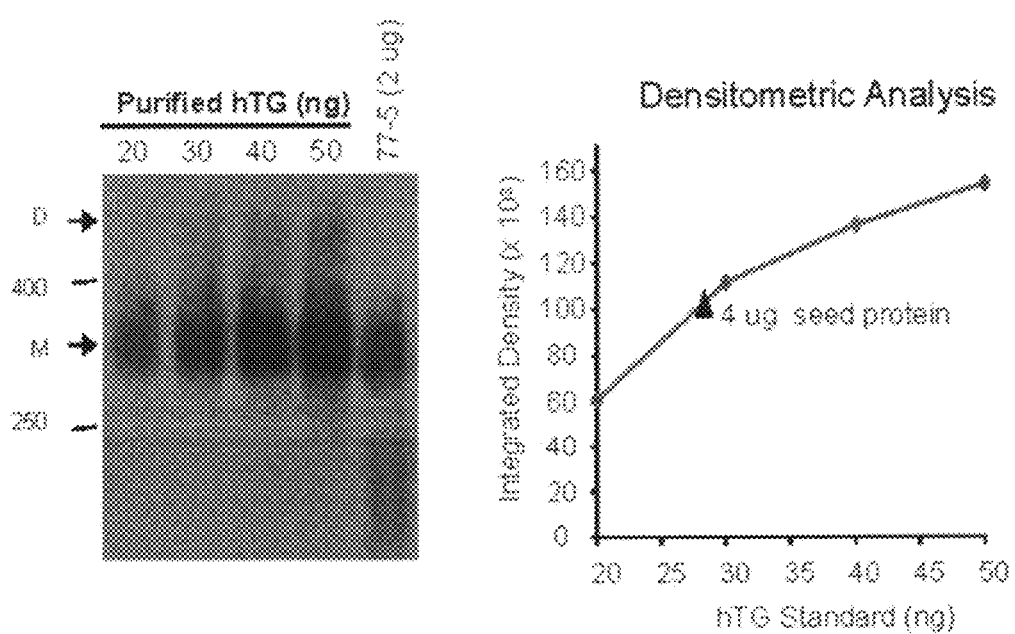
FIG. 8 represents western quantification of recombinant hTG using the gel on the left. The indicated amounts of commercially purified hTG protein and seed extract protein (line 77-5) were incubated in SDS-sample buffer (in the absence of β-mercaptoethanol and boiling) to relax dimeric protein and resulting in the predominantly monomeric protein for visualization and quantification following western analysis. A densitometry curve was generated by scanning the gel image and is shown on the right.

For western visualization and quantification, as shown in FIGS. 7 and 8, known amounts of commercially-purified hTG protein and crude seed-extracted protein (line 77-5) were incubated with SDS-sample buffer lacking β-mercaptoethanol, and electrophoresed in 5% native polyacrylamide gels. Western blots were performed and X-ray films of the resulting blots were scanned for densitometric analysis. Integrated density was measured using ImageJ software (Rasband, 1997-2005). The image was inverted and background pixel values were subtracted. A standard curve was plotted using these integrated density values and the known amounts of purified hTG protein, from which an absolute value of hTG in the seed sample was determined. For ELISA quantification, known amounts of hTG (0.01 ng-10 ng) and crude seed extracted protein (10-fold dilutions over four orders of magnitude) were coated onto ELISA plates and processed as described above. Absorbance values from the known concentrations of hTG were used to generate a curve, and the concentrations of hTG in seed extracts was determined by extrapolation of hTG concentration for those samples with absorbance values falling within the linear range of the curve. Absolute values were converted to a percentage of total protein.

In particular, in FIG. 7, a western analysis of T2 seed protein is shown. The crude seed extracts (5 µg) from 10 random T2 progeny were separated in 5% native polyacrylamide gels and screened by western blot analysis for the presence hTG. Thyroid-purified hTG (75 ng) served as a standard to visualize monomeric and dimeric forms of the protein. Nontransgenic seed protein (5 μg) served as a negative control. The locations of 400 kDa and 250 kDa molecular mass standards, as well as the monomeric (M) and dimeric (D) forms of hTG are indicated.

In FIG. 8, the western quantification of recombinant hTG is shown. The indicated amounts of commercially purified hTG protein and seed extract protein (line 77-5) were incubated in SDS-sample buffer (in the absence of β-mercaptoethanol and boiling) to relax dimeric protein and result in predominantly monomeric protein for visualization and quantification following western analysis. A densitometry curve was generated by scanning the gel image and plotting integrated density of each known standard using ImageJ software. Extrapolation from this curve revealed 27.97 ng of hTG protein in 5 ug of seed extract, representing 0.6% of total soluble seed protein for this particular sample.

Approximately 20% of thyroid cancer patients develop anti-thyroglobulin antibodies [21]. These autoantibodies can bind thyroglobulin and interfere with current FDA-approved thyroglobulin immunoassays. In additional studies, the inventors made use of some patients' sera to demonstrate the ability of these autoantibodies to bind soybean-derived thyroglobulin.

For these studies, thyroid-isolated thyroglobulin (Calbiochem, Inc.) or soybean-derived thyroglobulin were separately fractionated on a Sephacryl S-300 HR gel filtration column in a manner similar to that shown in FIG. 6A. Following gel filtration, fractions representing 59 to 60 milliliters of column void volume for thyroid-isolated and soybean-derived thyroglobulin were concentrated (using a Centricon-100). Quantification of the concentrated protein was accomplished using Bradford assays. Equivalent amounts (100 ng/well) of each thyroglobulin preparation were coated onto ELISA microtiter plates (Nunc high-binding) overnight as is routine in our laboratory. After blocking and washing, a 1:50 dilution of selected patients' sera and control sera were incubated on each coated plate. Two hours later, a peroxidase-conjugated anti-human IgG antibody was added. Bound anti-thyroglobulin autoantibodies were detected by the addition of substrate, and determining absorbance at 450 nm.

Figure 9:
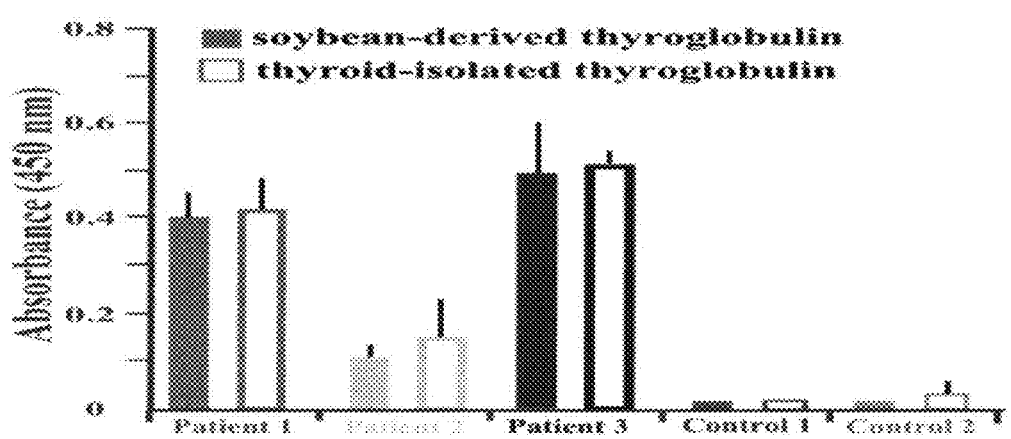
FIG. 9 illustrates recognition of soybean-derived and thyroid-isolated thyroglobulin by autoantibodies in sera from patients' and controls using an ELISA. Plates were coated with equal amounts of soybean-derived or thyroid-isolated thyroglobulin. The ability of autoantibodies from patients' sera to recognize each protein was determined using an ELISA. Results are presented as means of triplicate determinations (4 SD).

FIG. 9 shows that regardless of the source of thyroglobulin used to coat plates, there was no significant difference in the ability of autoantibodies in patients' sera to recognize soybean-derived (solid, bars) or thyroid-isolated (open bars) thyroglobulin. These results further demonstrate the antigenic identity of these two thyroglobulin isolates and suggest that the soybean derived thyroglobulin is similar to if not identical to at least one conformer of human wild type thyroglobulin.

Figure 12:
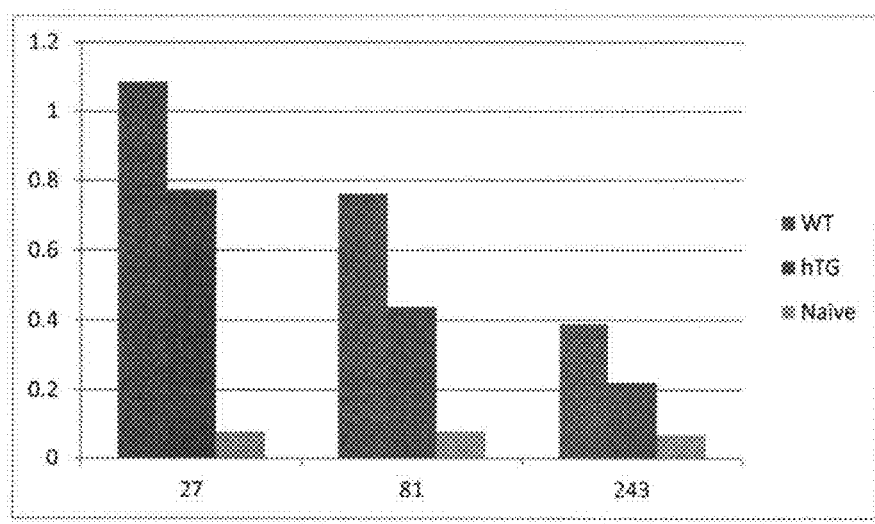
FIG. 12 is a graph that shows antibody titers against thyroglobulin in mice treated orally with soy-derived Tg. Dilutions of mouse sera from wild type (WT) and thyroglobulin (hTG) groups were analyzed. Eight serial dilutions of each sample were tested in the ELISA and absorbance values (on the y axis) versus the absorbance values at 450 nm (on the x axis) for three of these dilutions are shown (diluted by factors of 27, 81, and 243, respectively). The unimmunized control is shown as the last column (i.e., the right most column) in each of the three serial dilutions groups. WT and hTG groups were both N=5. The graph is representative of the relative B cell responses for wild type and thyroglobulin treated groups.
Figure 13:
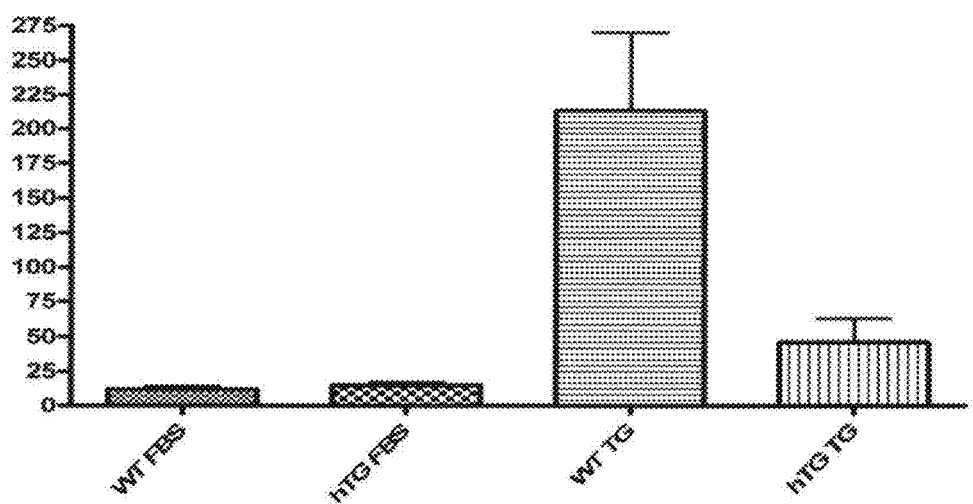
FIG. 13 shows the results of an interferon-γ (IFN-γ) ELISA study used to determine T-cell restimulation in the presence of commercial thyroglobulin. Splenocytes from wild type (WT) and thyroglobulin (hTG) groups were restimulated using commercial thyroglobulin (TG) and Fetal Bovine Serum (FBS) as a control. Supernatants were collected and analyzed via ELISA for the presence of IFN-γ. Results are shown in pg/ml. Both groups are N=5. One way analysis of variance (ANOVA) indicates a statistically significant difference between IFN-γ production in wild type splenocytes as compared to thyroglobulin group splenocytes (p=0.01).

FIGS. 12 and 13 show six to eight week old female Balb/c mice were gavaged every other day for 26 days as follows: using a 22 gauge feeding needle, 200 ul of soymilk protein extract from either wild type (non-transformed) seeds of transgenic seeds expressing hTG was administered to each animal via oral gavage. On day 14, both groups were immunized intraperitoneally with 100 ug of commercial human thyroglobulin (Calbiochem, UK) in aluminum hydroxide gel as an adjuvant (Sigma-Aldrich, St Louis, Mo.).

Following euthanasia on day 42, sera was collected for ELISA analyses. ELISA plates were coated with 100 ng of commercial hTG (Calbiochem) overnight at 4° C. Plates were then washed with PBS and blocked with 1% BSA-PBS for 1 hour. After a second wash, 100 ul of sera samples of varying dilutions were loaded on to the plate and incubated at room temperature for 2 hours. Following a third PBS wash, 100 ul of anti-mouse IgG-HRP antibody (Southern Biotech) at 1:500 dilution was added to each well and allowed to incubate for 1 hour. The antibody-antigen complexes were coated with TMB Substrate (BioFX, Owings Mills, Md.), and colorimetric reactions were stopped by the addition of 0.6 M sulfuric acid. Absorbance values were read at 450 nm.

FIG. 12 demonstrates that, at three different dilutions, there is a difference in antibody titers between the mice receiving wild type soymilk (WT) and the mice receiving soy-derived Tg (hTG). This suggests the mice that received the hTG soymilk formulation induced, at least partially, either a high or low-dose tolerance response to the antigen in the milk.

FIG. 12: Antibody titers against thyroglobulin in mice treated orally with soy-derived Tg.

Dilutions of mouse sera from wild type (WT) and thyroglobulin (hTG) groups were analyzed. Eight serial dilutions of each sample were tested in the ELISA and absorbance values for three of these dilutions are shown. WT and hTG groups were both N=5.

In addition, splenocytes were isolated for T-cell restimulation assays. Spleens were ground through 30 mesh screens to isolate leukocytes. Resulting cells were cultured in RPMI-1640 with 20% FBS (BD Biosciences, Chicago, Ill.). Cells were plated at $10^6$ cells per well in 96-well flat bottom tissue culture plates, coated with 10 ug commercial hTG or FBS and incubated for 72 hours. The supernatants from these cell cultures were analyzed for IFN-γ and Il-4 production via ELISA. FIG. 2 indicates the difference (p=0.02) in IFN-γ production between T-cells from the wild type group and those from the hTG group. The decreased production of IFN-γ indicates a shift to an anergic response by the T-cells to the stimulus. This is further supported by the high doses of tolerogen (280 ug) administered in each gavage.

FIG. 13 shows the results of IFN-γ ELISA used to determine T-cell restimulation in the presence of commercial thyroglobulin. Splenocytes from wild type (WT) and thyroglobulin (hTG) groups were restimulated using commercial thyroglobulin (TG) and Fetal Bovine Serum (FBS) as a control. Supernatants were collected and analyzed via ELISA for the presence of IFN-γ. Results are shown in pg/ml. Both groups are N=5. One way analysis of variance (ANOVA) indicates a statistically significant difference between IFN-γ production in wild type splenocytes as compared to thyroglobulin group splenocytes (p=01.01).

Thus, the present invention relates to novel soy-optimized thyroglobulin sequences, transformed plants, methods of making and using the soy-optimized thyroglobulin sequences such as assays using the soy-optimized thyroglobulin sequence(s).

In an embodiment, the present invention also relates to the use of novel formulations of soybean-derived thyroglobulin, and/or purified soybean-derived thyroglobulin, to prevent the development of, or limit ongoing, autoimmune responses against thyroglobulin in patients and animals.

The use of soybean-derived thyroglobulin for immunomodulation of autoimmune responses is unique due to: 1) the ability to express high levels of thyroglobulin in soybeans, providing the only current solution to the prohibitive cost of immunomodulatory therapy with thyroid-derived thyroglobulin; 2) the ability to treat prophylactically or therapeutically without practical limitations; 3) the ability to formulate, without purification or concentration, soybean-derived thyroglobulin into desirable therapeutics; 4) the ease of purification of soybean-derived thyroglobulin for formulation into desirable therapeutics; and 5) the particular chemical properties of soybean-derived thyroglobulin.

Presently, the only therapy for hypothyroidism is to treat the deficiency with hormone replace for the entire life of the patient. The advantages of oral or systemic suppression/tolerance induction over hormone replacement include: 1) focusing treatment on the cause of the disease, and not merely on treating symptoms. In theory, it should be possible to achieve a cure or to limit disease progression in many patients following a finite treatment with soybean-derived thyroglobulin therapeutic formulations. Therefore we are seeking a more permanent solution to this clinical problem than merely treating symptoms. 2) a therapy which does not require daily or continual treatment. It should not be necessary to treat individuals for their entire lifetime since, in theory, the induction of suppression tolerance would be a longer-term solution to this autoimmune disease. Stated simply, patients could manage disease by a single or periodic treatment, versus a daily hormone replacement pill for the rest of your life. 3) safety of treating all patients regardless of existing medical conditions. The consumption of soy milk or soy protein powder poses little risk, even in infants. Therefore patients with other health problems (e.g. renal insufficiency, cardiovascular disease, etc.) should have few, if any, contraindications for this therapy. 4) few side effects. Again, the safety of oral soy formulations will produce few, if any, side effects in almost all patients. 5) a broad therapeutic range for suppression/tolerance induction. We anticipate that there will be a wide range of therapeutic doses of oral thyroglobulin capable of inducing suppression/tolerance. Stated simply, soybean-derived thyroglobulin can be used in excess of the minimal amount required to induce suppression/tolerance and still be therapeutic without causing any clinical problems. 6) treatment of patients who have subclinical disease. Patients who are predisposed to develop autoimmune hypothyroidism or patients who have borderline disease would be candidates for suppression/tolerance therapy. In fact, suppression/tolerance therapy may be more efficacious if patients are treated at a preclinical stage or early during the clinical disease, prior to extensive damage of the thyroid gland. 7) the cost of therapy. Suppression/tolerance therapy will require less than one penny per dose. This would be a substantial cost savings versus levothyroxine.

Hormone replacement therapy with levothyroxine can be problematic since it is taken daily and since it has a relatively narrow therapeutic range which must be determined for each patient. Due to this narrow therapeutic range, it has been reported that approximately one fifth of patients taking levothyroxine are receiving an inadequate dose. Dosing can be affected by a variety of factors including non-compliance with daily dosing, drug interactions (e.g. iron, phenyloin, etc.), and malabsorption (e.g. gastrointestinal disease). Inadequate dosing results in a deficiency of thyroid hormones, and therefore does not fully relieve the symptoms associated with hypothyroidism (e.g. fatigue, depression, impaired memory, etc. Studies have also suggested that approximately one fifth of patients taking levothyroxine are receiving excessive amounts. This is also problematic since excessive thyroid hormone levels can result in thyrotoxicosis, bone loss, tachyarrhythmias, and other complications. Furthermore, autoimmune hypothyroidism is often a progressive disease, requiring treatment with levothyroxine to be monitored and adjusted with age and/or advancing disease. This fact adds to the cost (e.g. doctor's visits, etc.) required to maintain proper levels of thyroid hormones in these patients. Finally, when hypothyroidism is complicated by the presence of other conditions, the use of levothyroxine may be contraindicated. Patients who have other conditions (i.e. adrenal or renal insufficiency, cardiovascular disease, etc.) may not be able to use this drug or may have to be more closely monitored. Therapy with soybean-derived thyroglobulin treats the cause, not the symptoms of the disease, therefore the problems with the present hormone replacement therapy could be eliminated or greatly reduced.

Autoimmune hypothyroidism is usually a chronic condition that develops over a period of several years. Early stages of the disease are characterized by a modest elevation in thyroid stimulating hormone levels, with normal T4, and the presence of anti-thyroid antigen antibodies. These diagnostic findings define subclinical disease, also called "early thyroid failure". Up to 5% of these patients per year will progress to overt hypothyroidism as defined by decreased T4 levels. There is no effective therapy for patients who have subclinical disease which might prevent or delay progression to hypothyroidism. Such preclinical patients would be highly likely to benefit from suppression/tolerance therapy using oral or systemic formulations of soybean-derived thyroglobulin. Such prophylactic therapy would be aimed at limiting or eliminating disease progression so that future hormone replacement therapy would not be required.

The various SEQ ID NO:s from SEQ ID NO: 3 to SEQ ID NO:32 are different regions of the soy optimized thyroglobulin protein. For example SEQ ID NO: 3 is nucleotides 1-279 of SEQ ID NO: 1, SEQ ID NO: 4 is nucleotides 280-558 of SEQ ID NO: 1, etc.

Thus, in an embodiment, the present invention relates to a transgenic plant transformed with an exogenous nucleotide sequence that expresses a protein or a domain thereof wherein said protein or domain thereof is thyroglobulin or a domain thereof. The exogenous nucleotide sequence(s) comprises one or more sequences selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and SEQ ID NO: 32.

In a variation of the embodiment, the transgenic plant is a soybean plant.

SEQ ID NO: 1 represents the full length nucleotide sequence that expresses full length soy optimized thyroglobulin. The other SEQ ID numbers (except for SEQ ID NO: 2) are different regions of the full length nucleotide sequence that expresses full length soy optimized thyroglobulin (i.e., SEQ ID NO: 1). Thus, in an embodiment, the present invention relates to a transgenic plant transformed with an exogenous nucleotide sequence that expresses a protein where the protein is thyroglobulin and the exogenous nucleotide sequence is SEQ ID NO: 1.

In another embodiment, the present invention relates to a transgenic soybean wherein the exogenous nucleotide sequence comprises one or more sequences selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16.

Alternatively, the exogenous nucleotide sequence comprises one or more sequences selected from the group consisting of SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and SEQ ID NO: 32.

It should be recognized that in the above two paragraphs, any combination of the above-enumerated sequences are envisioned as possible sequences that can be inserted into soybean either individually or in combination with any other sequence.

In an embodiment, the transgenic soybean further comprises a nucleotide sequence that codes for a sequence that allows protein purification and/or a nucleotide sequence that confers selection (such as antibiotic resistance and/or herbicidic resistance and/or provides some distinguishing characteristic to the soybean plant that allows transgenic soybeans to be differentiated from wild type soybean plants) to the transgenic soybean. The selection gene can be either operably linked to the gene or it can be introduced in an "unlinked" fashion. This means that the transgenic soybean can be segregated away to leave only the gene of interest (e.g. hTG) in the transgenic plant. Possible protein purification sequences include one or more of a His tagged linker, GST tags. FLAG tags, HA tags, and MYC tags. It is also contemplated that chemical binding reagents can be used in purification procedures. For example, biotin may be attached to the thyroglobulin protein or domain thereof allowing purification using strepavidin.

In a variation of the embodiment, the transgenic soybean may possess a plant selectable marker such as a sequence that confers antibiotic and/or herbicidic resistance. In one embodiment, this resistance may be glufosinate resistance. Alternatively, other sequences that confer antibiotic and/or herbicidic resistance may be used. For example, the transgenic plant (soybean) of the present invention may have a gene itself, or there may be a gene in a bacterial vector that is used in the plant that provides a selectable marker such as conferring resistance to antibiotics and/or herbicides. Non-limiting examples include a gene that confers ampicillin resistance, cloaxicillin resistance, kanamycin resistance, or bialophos resistance.

In another embodiment, a screenable marker may be used instead of, or in conjunction with a selectable marker.

In an embodiment, the transgenic soybean will overexpress the soy optimized thyroglobulin such that the thyroglobulin or domain thereof is expressed in an amount that is 0.3% or greater of total protein concentration. Alternatively, the level of protein may be 0.5% or greater of total protein concentration. Alternatively, the level of protein may be 1% or greater of total protein concentration. In a variation of the embodiment, the level of protein may be 2% or greater of total protein concentration. Alternatively, the level of protein may be 3% or greater of total protein concentration.

Soybean can be readily transformed by an array of different transformation methods which have been developed and optimized over the past decade in various laboratories. In addition to the above described transformations, other transformations known in the art may be used.

Accordingly, in an embodiment, the present invention might use transformation techniques that are the cotyledonary node transformation using the bacteria *Agrobacterium tumefaciens* or the particle bombardment of somatic embryogenic cultures. Regeneration using somatic embryogenesis is also within the scope of the present invention using a variety of explant tissue including embryonic axes, intact zygotic embryos, and excised cotyledons.

Other methods have also been developed to transform soybean and are contemplated and therefore within the scope of the present invention. One example is the introduction of exogenous DNA into a plant embryo through the pollen tube pathway after pollination. Another method is the use of *Agrobacterium rhizogenes*, which causes hairy root disease and is used in a manner similar to *A. tumefaciens* to infect wound sites on roots and transfer T-DNA from the bacterial cell to the plant cell. Other methods of soybean transformation include electroportation, microinjection, silicon carbide fibers, liposome-mediated transformation and in planta *Agrobacterium*-mediated transformation using vacuum infiltration of whole plants.

In another embodiment, the present invention relates to an isolated nucleic acid comprising SEQ ID NO: 1 and variants thereof that are at least 80% identical to SEQ ID NO: 1. The nucleic acid of SEQ ID NO: 1 and variants thereof may be purified. Alternatively, the isolated nucleic acid may comprise SEQ ID NO: 1 and variants thereof that are at least 90% identical to SEQ ID NO: 1. Alternatively, the isolated nucleic acid may comprise SEQ ID NO: 1 and variants thereof that are at least 92% identical to SEQ ID NO: 1. Alternatively, the isolated nucleic acid may comprise SEQ ID NO: 1 and variants thereof that are at least 95% identical to SEQ ID NO: 1. Alternatively, the isolated nucleic acid may comprise SEQ ID NO: 1 and variants thereof that are at least 99% identical to SEQ ID NO: 1.

In another embodiment, the present invention relates to an isolated nucleic acid having a nucleotide sequence selected from the group consisting of a) the nucleotide sequence set forth in SEQ ID NO: 1 and b) a fragment of the nucleotide sequence of SEQ ID NO: 1 that is at least 100 nucleotides in length. Alternatively, the fragment of the nucleotide sequence of SEQ ID NO: 1 may be at least 50 nucleotides in length. Alternatively, the fragment of the nucleotide sequence of SEQ ID NO: 1 may be at least 250 nucleotides in length. Alternatively, the fragment of the nucleotide sequence of SEQ ID NO: 1 may be at least 500 nucleotides in length.

In an alternate embodiment, the present invention relates to a nucleic acid comprising one or more sequences selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14. SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and SEQ ID NO: 32.

In an embodiment, the present invention relates to a method of producing and isolating human thyroglobulin or a domain thereof comprising: a) synthesizing an exogenous nucleotide sequence comprising one or more sequences selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and SEQ ID NO: 32; b) transforming a soybean with one or more of said sequences selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10. SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and SEQ ID NO: 32; c) growing the soybean in a medium wherein human thyroglobulin or a domain thereof is expressed from one or more of said sequences selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13. SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and SEQ ID NO: 32; d) isolating human thyroglobulin or a domain thereof.

In a variation of the embodiment of the method, the transformed soybean further comprises one or more of a seed-specific promoter(s), a nucleotide sequence expressing a transcriptional or translational enhancer (e.g. tobacco etch virus), a polyadenylation signal, a His tag nucleotide sequence, a nucleotide sequence that confers antibiotic resistance, and/or a leader sequence (or endogenous leader or any alternative leader sequence that targets expression to the secretory pathway (for example in the ER).

In a variation of the embodiment, the transformed soybean comprises a leader sequence and this transformed soybean may be used in the above method(s).

In a further variation, an expression cassette is used and is cloned into a binary vector. The expression cassette cloned into the binary vector may be used in the transgenic soybean or in any method using and/or making the transgenic soybean.

In an embodiment, the present invention is also directed to compositions and methods of treating, ameliorating, reducing, and/or eliminating an autoimmune response associated with individuals that suffer from autoimmune thyroiditis. In a variation, the symptoms of the disease may be treated, ameliorated, reduced, and/or eliminated.

In a variation of the embodiment, the method of treating, ameliorating, reducing, and/or eliminating the autoimmune response against thyroglobulin seen in individuals with autoimmune thyroiditis comprising administering to said individuals recombinant thyroglobulin or a domain thereof. In a variation, the recombinant thyroglobulin or domain thereof is expressed in soybean.

In a variation, the recombinant thyroglobulin or domain thereof comprises one or more sequences selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15. SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and SEQ ID NO: 32.

In a variation, the soybean can be a plurality of forms such as a soymilk protein extract, soybean, or soybean powder.

In an embodiment, the individuals can ingest the soybean. Alternatively, the soybean can be taken subcutaneously, parenterally, or rectally.

In an embodiment, the present invention relates to a composition for reducing and/or eliminating the autoimmune response against thyroglobulin seen in individuals with autoimmune thyroiditis, wherein said composition comprises recombinant thyroglobulin or a domain thereof that is expressed in soybean and contains one or more of the sequences selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 1, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and SEQ ID NO: 32.

In a variation, the composition further comprises one or more of an adjuvant, a diluent, an excipient, or a carrier.

In a further variation, the thyroglobulin or domain thereof is expressed in an amount that is 0.1% or greater, or 0.2% or greater, or 0.3% or greater, or 0.4% or greater, or 0.5% or greater, 0.6% or greater of total protein concentration. In a variation, the thyroglobulin or domain thereof is expressed in an amount that is 0.5% or greater of total protein concentration.

The following examples show some of the embodiments of In Vitro Diagnostic (IVD) Assays that utilize Soy-Tg such as an Analyte-Specific Reagent (ASR).

For patients with thyroid disease (i.e. thyroiditis and thyroid cancers), several FDA-approved in vitro diagnostic (IVD) assays are routinely used to diagnose and monitor their diseases. Specifically, thyroiditis patients can be screened for the presence of serum autoantibodies against thyroglobulin (TG). The presence of such autoantibodies confirms disease, suggests treatment regimens, and aids in monitoring development of disease.

In addition, thyroid cancer patients, who have had organ ablation, are routinely monitored for the presence of serum TG to assess whether malignant thyroid tissue still remains. For both thyroiditis and thyroid cancer patients, these various IVD immunoassays are the gold standards for diagnosis and monitoring.

In an embodiment. Soy-Tg can be used in IVD assays that 1) detect antibodies against Human-Tg; and 2) require a reference standard for quantification of Human Tg levels in fluids (for example, including but not limited to its use in sera, saliva, urine, blood, etc.).

In another embodiment. Soy-Tg can be used as a reference standard for the industry.

The lack of a universally consistent Human-Tg standard contributes significantly to variability between FDA-approved assays made by different suppliers (see 14, 15, 16, 17 and 18). Differences in the quantification of thyroglobulin between assays are so great that the results from one assay cannot be extrapolated to results obtained using other assays. Physicians must therefore know which assay system their particular clinical laboratory is using, and be careful not to compare results from one assay to another. Due to the homogeneity of Soy-Tg the Soy-Tg or domains thereof can be used as the reference standard for the industry to normalize all assays using hTg.

In another embodiment, Soy-Tg can be used in connection with a medical device to remove anti-thyroglobulin (TG) antibodies from biological samples (e.g. patients' sera) to eliminate interference in hTg immunoassays.

The most significant limitation with present day hTg immunoassays is the quantification of thyroglobulin levels in patients' sera that contain autoantibodies against thyroglobulin (see 16 and 18). Detection of thyroglobulin in cancer patients' sera that have had thyroid ablation is the gold standard for detecting metastasized tumor tissue. Unfortunately, approximately 30% of thyroid cancer patients develop anti-thyroglobulin antibodies. These autoantibodies can bind thyroglobulin in sera and interfere with the ability to detect this molecule in all current FDA-approved thyroglobulin immunoassays (giving erroneous results). Presently, there is no clear solution for this significant problem. Therefore these patients are left with no clear method for monitoring the presence of any metastatic thyroid cancer remnants.

By immobilizing an excessive amount of Soy-TG on immunoaffinity discs, it is possible to remove anti-TG antibodies from patients' sera making the sera essentially free of anti-TG antibodies. The anti-TG antibody depleted sera can then be used to accurately measure thyroglobulin in patients' sera. The ability of the affinity cartridge to remove autoantibodies from patient's sera, while releasing antibody-bound thyroglobulin for measurement by immunoassays, is therefore a unique solution that allows for a more accurate diagnosis of thyroglobulin levels, allowing for a more accurate diagnosis of cancer.

Thus, in an embodiment, the present invention relates to a method of accurately detecting thyroglobulin concentration or a concentration of a domain of thyroglobulin in an individual comprising: a) obtaining sera from the individual; b) contacting the sera with an immunoaffinity disc that comprises thyroglobulin or a domain thereof isolated from a transformed soybean; c) allowing the immunoaffinity disc that comprises thyroglobulin or the domain thereof to bind antibodies in the sera; d) separating the sera from the immunoaffinity disc; and e) detecting the amount of thyroglobulin in the sera.

The method can be used to detect cancer, wherein an elevated thyroglobulin concentration indicates the presence of cancer.

In a variation of the embodiment, the method uses thyroglobulin protein or a domain thereof isolated from a transformed soybean, which is encoded for by an exogenous nucleotide sequence and said exogenous nucleotide sequence comprises one or more nucleotide sequences selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and SEQ ID NO: 32.

In a variation of the embodiment, the immunoaffinity disc that comprises thyroglobulin or a domain thereof is attached to the immunoaffinity disc by a covalent bond. Alternatively, the bond may be ionic, or there may be other forces that keep the thyroglobulin or domain thereof attached to the disc, such as van der Waals forces and/or hydrophobic interactions.

In an embodiment, the soy optimized thyroglobulin is expressed free of iodine. In a variation of the embodiment, iodine can be chemically added so that the amount of iodination is carefully controlled. Thus, in a variation of the embodiment, the present invention relates to thyroglobulin expressed by the nucleotide sequences of the present invention with differing amounts of iodine present therein (e.g., T0, T1, T2, T3, T4, etc.).

In an embodiment, the non-iodinated or iodinated thyroglobulin can be administered to an individual to treat the individual for one of the thyroglobulin implicated diseases. Thus, methods using non-iodinated and iodinated thyroglobulin for this treatment are contemplated.

With this description of the embodiments and illustrated by the figures of the present invention, it should be apparent that modifications can be made to the above described embodiments without departing from the spirit and scope of the invention. The above written description provides a description of the various embodiments including products and methods of making and of use of exemplary embodiments of the invention. However, the above discussed variations and embodiments are to be construed so that the invention contains other reasonable variations of the invention that are not explicitly described. Moreover, it is contemplated and therefore within the scope of the invention that any above-described embodiment and/or feature can be combined with any other above-described embodiment and/or feature. In any event, the invention is to be defined by the appended claims.

The following references are herein incorporated by reference in their entirety.

[1] Enewold L. Zhu K, Ron E. Marrogi A J, Stojadinovic A, Peoples G E, et al. Rising thyroid cancer incidence in the United States by demographic and tumor characteristics, 1980-2005. Cancer Epidemiol Biomarkers Prev. 2009 March; 18(3):784-91.

[2] Davies L, Welch H G. Increasing incidence of thyroid cancer in the United States, 1973-2002. Jama. 2006 May 10; 295(18):2164-7.

[3] Benbassat C A, Mechlis-Frish S, Guttmann H, Glaser B. Krausz Y. Current concepts in the follow-up of patients with differentiated thyroid cancer. Isr Med Assoc J. 2007 July; 9(7):540-5.

[4] van de Graaf S A, Ris-Stalpers C. Pauws E, Mendive F M, Targovnik H M, de Vijlder J J. Up to date with human thyroglobulin. The Journal of endocrinology. 2001 August; 170(2):307-21.

[5] Venkatesh S G, Deshpande V. A comparative review of the structure and biosynthesis of thyroglobulin. Comparative biochemistry and physiology. 1999 January; 122(1): 13-20.

[6] Feldt-Rasmussen U. Profilis C, Colinet E, Black E, Bornet H, Bourdoux P, et al. Human thyroglobulin reference material (CRM 457). 2nd Part: Physicochemical characterization and certification. Annales de biologic clinique. 1996; 54(10-11):343-8.

[7] Jun J Y, Manni A. Medical management of persistent or recurrent differentiated thyroid carcinoma. Otolaryngologic clinics of North America. 2008 December; 41(6): 1241-60, xi-xii.

[8] Mazzaferri E L, Robbins R J, Spencer C A, Braverman L E, Pacini F, Wartofsky L, et al. A consensus report of the role of serum thyroglobulin as a monitoring method for low-risk patients with papillary thyroid carcinoma. The Journal of clinical endocrinology and metabolism. 2003 April; 88(4): 1433-41.

[9] Whitley R J, Ain K B. Thyroglobulin: a specific serum marker for the management of thyroid carcinoma. Clinics in laboratory medicine. 2004 March; 24(1):29-47.

[10] Emerson C H, Torres M S. Recombinant human thyroid-stimulating hormone: pharmacology, clinical applications and potential uses. BioDrugs. 2003; 17(1):19-38.

[11] Persoon A C, Jager P L, Sluiter W J, Plukker J T, Wolffenbuttel B H, Links T P. A sensitive Tg assay or rhTSH stimulated Tg: what's the best in the long-term follow-up of patients with differentiated thyroid carcinoma?PLoS ONE. 2007; 2(8):e816.

[12] Wong R, Topliss D J, Bach L A, Hamblin P S, Kalff V, Long F. et al. Recombinant human thyroid-stimulating hormone (Thyrogen) in thyroid cancer follow up: experience at a single institution. Internal medicine journal. 2009 March; 39(3): 156-63.

[13] The Cancer Diagnostics Market: Emerging Opportunities and Business Expansion Strategies: Venture Planning Group Report; October 2008.

[14] Clark P M. Laboratory services for thyroglobulin and implications for monitoring of differentiated thyroid cancer. Journal of clinical pathology. 2009 May; 62(5):402-6.

[15] Dufour D R. Thyroglobulin and thyroglobulin antibodies. Thyroid Cancer: A Comprehensive Guide to Clinical Management. 2nd ed. Totowa, N.J.: Humana Press, Inc. 2008:297-304.

[16] Krahn J, Dembinski 1. Thyroglobulin and anti-thyroglobulin assays in thyroid cancer monitoring. Clinical biochemistry. 2009 March; 42(4-5):416-9.

[17] Spencer C A, Bergoglio L M, Kazarosyan M, Fatemi S, LoPresti J S. Clinical impact of thyroglobulin (Tg) and Tg autoantibody method differences on the management of patients with differentiated thyroid carcinomas. The Journal of clinical endocrinology and metabolism. 2005 October; 90(10):5566-75.

[18] Spencer C A, Lopresti J S. Measuring thyroglobulin and thyroglobulin autoantibody in patients with differentiated thyroid cancer. Nature clinical practice. 2008 April; 4(4): 223-33.

[19] Barin J G, Talor M V, Sharma R B, Rose N R, Burek C L. Iodination of murine thyroglobulin enhances autoimmune reactivity in the NOD.H2 mouse. Clinical and experimental immunology. 2005 November; 142(2):251-9.

[20] Latrofa F, Phillips M, Rapoport B, McLachlan S M. Human monoclonal thyroglobulin autoantibodies: epitopes and immunoglobulin genes. The Journal of clinical endocrinology and metabolism. 2004 October; 89(10): 5116-23.

[21] Hollowell J G, Staehling N W, Flanders W D, Hannon W H, Gunter E W, Spencer C A, et al. Serum TSH, T(4), and thyroid antibodies in the United States population (1988 to 1994): National Health and Nutrition Examination Survey (NHANES III). The Journal of clinical endocrinology and metabolism. 2002 February; 87(2):489-99.

[22] Liu K. Soybeans: Chemistry, Technology, and Utilization. Gaithersburg, Md.: Aspen Publishers, Inc. 1999.

[23] Traynor P L, Adair, D., Irwin, R. A practical guide to containment: Greenhouse research with transgenic plants and microbes. Blacksburg, Va.: Information Systems for Biotechnology 2001.

[24] Garg R. Tolbert M, Oakes J L, Clemente T E, Bost K L, Piller K J. Chloroplast targeting of FanC, the major antigenic subunit of *Escherichia coli* K99 fimbriae, in transgenic soybean. Plant cell reports. 2007 July; 26(7): 1011-23.

[25] Piller K J, Clemente T E, Jun S M, Petty C C, Sato S, Pascual D W, et al. Expression and immunogenicity of an *Escherichia coli* K99 fimbriae subunit antigen in soybean. Planta. 2005 September; 222(1):6-18.

[26] Gagnon P. Monoliths seen to revitalize bioseparations. Genetic Engineering & Biotechnology News. 2006; 26(17).

[27] Gagnon P. The emerging generation of chromatography tools for virus purification. BioProcess International. 2008; October 2008 supplement: 24-30.

[28] Hage D S. Affinity chromatography: a review of clinical applications. Clinical chemistry. 1999 May; 45(5):593-615.

[29] Mallik R, Hage D S. Affinity monolith chromatography. Journal of separation science. 2006 August; 29(12): 1686-704.

[30] Paz M M, Martinez J C, Kalvig A B, Fonger T M, and Wang K. Improved cotyledonary node method using an alternative explant derived from mature seed for efficient *Agrobacterium*-mediated soybean transformation. Plant Cell Rep. 2006; 25: 206-213.

[31] Oakes J L, Bost K L, and Piller K J Stability of a soybean seed-derived vaccine antigen following long-term storage, processing and transport in the absence of a cold chain. J Sci Food Agric 2009; 89: 2191-2199.

[32] Lee, S., N. Scherberg, and L. J. DeGroot. 1998. Induction of oral tolerance in human autoimmune thyroid disease. Thyroid 8:229-234.

[33] Peterson, K. E., and H. Braley-Mullen. 1995. Suppression of murine experimental autoimmune thyroiditis by oral administration of porcine thyroglobulin. Cellular immunology 166:123-130.

[34] Parish, N. M., D. Rayner, A. Cooke, and I. M. Roitt. 1988. An investigation of the nature of induced suppression to experimental autoimmune thyroiditis. Immunology 63:199-203.

[35] Sanker, A. J., C. R. Clark, and R. S. Sundick. 1985. The induction of tolerance to thyroglobulin significantly reduces the severity of thyroiditis in obese strain chickens. J Immunol 135:281-285.

[36] Guimaraes, V. C., J. Quintans, M. E. Fisfalen, F. H. Straus, P. E. Fields, G. Medeiros-Neto, and L. J. DeGroot. 1996. Immunosuppression of thyroiditis. Endocrinology 137:2199-2207.

[37] Guimaraes, V. C. J. Quintans. M. E. Fisfalen. F. H. Straus. K. Wilhelm, A. Medeiros-Neto, and L. J. DeGroot. 1995. Suppression of development of experimental autoimmune thyroiditis by oral administration of thyroglobulin. Endocrinology 136:3353-3359.

[38] Gardine, C. A., F. Gentile, C. Pellegrini, F. Giallauria, G. Torelli, T. Kouki, and L. DeGroot. 2003. Multiple fragments of human TG are capable of inducing oral tolerance to whole human TG. J Endocrinol Invest 26:294-300.

[39] Rapoport. B., and S. M. McLachlan. 1996. Food for thought—is induction of oral tolerance feasible and practical in human thyroid autoimmunity?Endocrinology 137: 2197-2198.

[40] Klein, I., and S. Danzi. 2003. Evaluation of the therapeutic efficacy of different levothyroxine preparations in the treatment of human thyroid disease. Thyroid 13:1127-1132.

[41] Clarke, N., and U. M. Kabadi. 2004. Optimizing treatment of hypothyroidism. Treatments in endocrinology 3:217-221.

[42] Evans, T. C. 2003. Thyroid disease. Prim Care 30:625-640.

[43] Hueston, W. J. 2001. Treatment of hypothyroidism. Am Fam Physician 64:1717-1724.

[44] Roberts, C. G., and P. W. Ladenson. 2004. Hypothyroidism. Lancet 363:793-803.

[45] Dayan. C. M., and G. H. Daniels. 1996. Chronic autoimmune thyroiditis. N Engl J Med 335:99.
[46] Pearce, E. N., A. P. Farwell, and L. E. Braverman. 2003. Tlhyroiditis. N Engl J Med 348:2646.
[47] Rose, N. R., and I. R. Mackay. 1998. The Autoimmune Diseases. Academic Press. San Diego, Calif.
[48] Weetman, A. P. 2003. Autoimmune thyroid disease: propagation and progression. Eur J Endocrinol 148:1.
[49] Diez, J. J., I. Molina, and M. T. Ibars. 2003. Prevalence of thyroid dysfunction in adults over age 60 years from an urban community. Exp Clin Endocrinol Diabetes 111:480.
[50] Flynn, R. W., T. M. MacDonald, A. D. Morris, R. T. Jung, and G. P. Leese. 2004. The thyroid epidemiology, audit, and research study: thyroid dysfunction in the general population. J Clin Endocrinol Metab 89:3879.
[51] Slatosky, J., B. Shipton, and H. Wahba. 2000. Thyroiditis: differential diagnosis and management. Am Fam Physician 61:1047.
[52] Wertheimer, A. I., and T. M. Santella. 2005. The levothyroine spectrum: Bioequivalence and cost considerations. Formulary 40:258.
[53] Vladutiu, A. O., and N. R. Rose. 1975. Cellular basis of the genetic control of immune responsiveness to murine thyroglobulin in mice. Cell Immunol 17:106.
[54] Maron, R., R. Zerubavel, A. Friedman, and I. R. Cohen. 1983. T lymphocyte line specific for thyroglobulin produces or vaccinates against autoimmune thyroiditis in mice. J Immunol 131:2316.
[55] Vali, M., N. R. Rose, and P. Caturegli. 2000. Thyroglobulin as autoantigen: structure-function relationships. Rev Endocr Metab Disord 1:69.
[56] Quaratino, S., E. Badami, Y. Y. Pang, I. Bartok, J. Dyson, D. Kioussis, M. Londei, and L. Maiuri. 2004. Degenerate self-reactive human T-cell receptor causes spontaneous autoimmune disease in mice. Nat Med 10:920.

We claim:

1. A transgenic soybean plant transformed with a nucleotide sequence encoding full length human thyroglobulin.

2. The transgenic plant according to claim 1, wherein the soybean comprises exogenous nucleotide sequence SEQ ID NO: 1.

3. The transgenic soybean according to claim 1, further comprising a nucleotide sequence that codes for a sequence that allows protein purification and/or a nucleotide sequence that allows for plant selection such as a His tag and/or a sequence that codes for glufosinate resistance.

4. The transgenic soybean according to claim 1, wherein thyroglobulin is expressed in an amount that is 0.5% or greater of total protein concentration.

5. A method of producing and isolating human thyroglobulin, said method comprising:
   a) synthesizing an exogenous nucleotide sequence comprising SEQ ID NO: 1;
   b) transforming a soybean with said sequence;
   c) growing the soybean in a medium wherein human thyroglobulin is expressed; and,
   d) isolating human thyroglobulin thereof from said soybean.

6. The method of claim 5, wherein the transformed soybean further comprises one or more of a seed-specific promoter, a leader sequence, a transcriptional and/or translational enhancer, a polyadenylation signal, a nucleotide sequence encoding a His tag, and/or a nucleotide sequence that confers herbicide resistance.

7. The method of claim 6, wherein the nucleotide sequence is in an expression cassette, and wherein the expression cassette is cloned into a binary vector.

8. A method of quantitatively detecting thyroglobulin concentration in an individual comprising:
   a) obtaining sera from the individual;
   b) contacting the sera with an immunoaffinity disc that comprises thyroglobulin isolated from a transformed soybean grown in a medium wherein thyroglobulin is expressed wherein said thyroglobulin is obtained from expression of an exogenous thyroglobulin construct that comprises a soybean β-conglycinin promoter;
   c) allowing the immunoaffinity disc that comprises thyroglobulin to bind antibodies in the sera;
   d) separating the sera from the immunoaffinity disc; and
   e) detecting the amount of thyroglobulin in the sera.

9. The method of claim 8, wherein the method is used to detect cancer, wherein an elevated thyroglobulin concentration indicates the presence of cancer.

10. The method of claim 8, wherein the thyroglobulin construct further comprises an endogenous leader sequence.

11. The method of claim 10, wherein the thyroglobulin construct further comprises a sequence encoding a histidine tag.

12. The method of claim 8, wherein the thyroglobulin that is isolated from a transformed soybean is recognized by a Kronus ELISA.

13. The method of claim 8, wherein said thyroglobulin is more homogenous than thyroglobulin purified from human tissue.

14. The method of claim 8, wherein the isolated thyroglobulin is dimeric.

* * * * *

SEQUENCE LISTING

<160> NUMBER OF SEQ ID NOS: 37

<210> SEQ ID NO 1
<211> LENGTH: 8349
<212> TYPE: DNA
<213> ORGANISM: Artificial Sequence
<220> FEATURE:
<223> OTHER INFORMATION: unknown

<400> SEQUENCE: 1

```
ggtaccatgg ctcttgtgct cgagattttc acccttctcg cttctatttg ctgggtgtcc      60
gctaacattt tcgagtacca ggttgacgct caaccactta gaccatgcga gcttcaaaga     120
gagactgctt tcctcaagca ggctgattat gttccacaat gcgctgagga tggatctttc     180
caaactgttc agtgccaaaa cgatggaaga tcttgctggt gtgttggagc taacggatct     240
gaggttttgg gatctaggca accaggtaga ccagttgctt gcctttcttt ctgccagctt     300
cagaagcagc agattcttct ctccggttac atcaactcta ccgacacctc ttatcttcca     360
cagtgccagg attctggtga ttacgctcca gttcaatgcg acgttcaaca agttcaatgc     420
tggtgcgttg atgctgaggg aatggaagtt tacggaacca gacaacttgg aaggccaaag     480
agatgcccaa gatcctgcga gattaggaac agaaggcttc ttcacggagt tggagataag     540
tctccaccac aatgctctgc tgaaggcgag ttcatgcctg ttcagtgcaa gttcgtgaac     600
accaccgaca tgatgatttt cgatctcgtg cactcctata acagattccc agatgccttc     660
gtgactttct cttccttcca gagaagattc ccagaggttt caggatattg ccactgcgct     720
gattctcaag gtagagagct tgctgagact ggacttgagc ttctcctcga tgagatctac     780
gataccattt tcgctggact tgatcttcca tctaccttca ccgagactac cctttacagg     840
attctccaaa gaagattcct cgctgttcag tctgttattt ccggaagatt caggtgccca     900
actaagtgcg aggttgagag gttcactgct acttcattcg gacatccata cgttccatct     960
tgcagaagaa acggcgatta ccaggctgtt caatgccaaa ctgagggacc atgttggtgt    1020
gttgatgccc agggaaaaga aatgcatgga accaggcaac aaggtgaacc accatcttgc    1080
gctgaaggac aatcttgcgc ttctgagagg caacaagctc tttctaggct ctacttcgga    1140
acctctggat acttctccca gcacgatctt ttctcttcac cagagaagag atgggcttct    1200
ccaagagttg ctagattcgc tacttcttgc ccaccaacca tcaaagagct tttcgttgat    1260
tccggacttc ttaggccaat ggttgaggga caatctcagc agttctctgt gtctgagaac    1320
```

-continued

```
cttctcaaag aggctattag ggctattttc ccatctaggg gacttgctag gcttgctctt    1380
caattcacca ccaacccaaa gaggcttcag caaaaccttt tcggaggaaa gttcctcgtt    1440
aatgtgggac agttcaacct ttctggtgct cttggaacta ggggaacctt caacttctct    1500
cagttcttcc agcaacttgg acttgcttct ttccttaacg gtggcaggca agaggatctt    1560
gcaaagccac tttctgtggg acttgattct aactcttcca ctggaactcc agaggctgct    1620
aagaaagatg gcaccatgaa caagccaact gtgggatctt tcggcttcga gatcaacctt    1680
caagagaacc agaacgctct taagttcctt gcttcccttc ttgagcttcc agagttcctt    1740
cttttcctcc agcacgctat ttctgttcca gaggatgtgg ctagagatct tggtgatgtg    1800
atggaaaccg tgctttcttc tcaaacttgc gagcaaactc cagagagact tttcgttcct    1860
tcttgcacta ctgagggatc ttacgaggat gttcagtgct tctctggtga gtgttggtgc    1920
gttaactctt ggggaaaaga gcttccagga tcaagagtta gaggtggaca acctagatgc    1980
ccaactgatt gcgagaagca aagggctagg atgcaatctc ttatgggatc tcagccagct    2040
ggatctactc ttttcgtgcc agcttgcact tctgaaggac acttccttcc agtgcaatgc    2100
ttcaactctg agtgctattg cgtggatgct gaaggtcaag ctattccagg aaccagatcc    2160
gctattggca agccaaagaa gtgcccaact ccttgccaac ttcaatctga gcaggctttc    2220
cttaggactg ttcaggctct tcttttccaac tcttccatgc ttccaacccct ttccgatacc    2280
tacattccac agtgctctac tgatggacag tggagacaag ttcagtgtaa cggaccacca    2340
gagcaagttt tcgagcttta ccagagatgg gaggctcaaa acaagggaca agatctcact    2400
ccagctaagt tgctcgtgaa gatcatgtct tacagagagg ctgcttctgg aaacttcagc    2460
ctcttcatcc agtcacttta cgaggctgga cagcaagatg ttttcccagt gctttctcag    2520
tacccatctc ttcaggatgt tccacttgct gctcttgagg gaaaaagacc acagccaaga    2580
gagaacattc ttctcgagcc ttacctcttc tggcagattc ttaacggaca gctttcacag    2640
tatcctggtt cctactctga tttctctacc ccactcgctc atttcgatct tagaaactgc    2700
tggtgtgtgg atgaagctgg acaagagctt gagggaatga gatctgagcc atctaagttg    2760
ccaacttgcc caggatcttg cgaggaagct aagttgagag tgctccagtt cattagggaa    2820
accgaggaaa ttgtgtctgc ttctaactcc tctaggttcc cacttggaga gtcttttcctt    2880
gtggctaagg gaattaggct taggaacgag gatcttggac ttccaccact tttcccacca    2940
agagaggctt tcgctgaaca attcctcagg ggttccgatt atgctattag gcttgctgct    3000
cagtctacct tgtctttcta ccagagaaga aggttctctc cagacgattc tgctggtgct    3060
tctgctcttc ttagatccgg accttacatg ccacaatgcg acgcttttgg atcttgggag    3120
ccagttcaat gtcatgctgg aactggacac tgttggtgcg tggatgagaa gggcggtttc    3180
attccaggat ctcttaccgc tagatccctt cagattccac aatgccctac tacttgcgag    3240
aagtctagga cctctggact tctttcttct tggaagcagg ctaggtcaca agaaaaccca    3300
tccccaaagg atctttttcgt tccagcatgc cttgagactg gtgagtatgc tagacttcag    3360
gcttctggtg ctggaacatg gtgtgttgac ccagcttctg gtgaagaact taggccagga    3420
tcttcttctt ctgctcagtg cccatctttg tgcaacgtgc ttaagtctgg tgttcttttcc    3480
agaagagtgt ctccaggata tgttccagct tgcagagctg aggatggtgg attctctcca    3540
gttcagtgtg atcaagctca aggatcttgt tggtgcgtga tggattctgg tgaagaggtt    3600
ccaggaacta gagttactgg cggacaacca gcttgtgaat ctccaagatg cccacttcca    3660
ttcaacgctt cagaggttgt gggaggaact attctctgcg agactatttc tggaccaacc    3720
```

```
ggttctgcta tgcaacaatg ccagcttttg tgcagacaag gatcttggtc tgttttccca    3780
ccaggaccac ttatttgctc ccttgagtct ggaagatggg agtctcaact ccacaacct     3840 agagcttgcc aaagaccaca actctggcaa actattcaga cccagggaca tttccaactt    3900
caactcccac ctggaaagat gtgctctgct gattacgctg atcttctcca gactttccag    3960
gtgttcatcc tcgatgagct tactgctaga ggattctgcc agatccaggt taagactttc    4020
ggaaccctcg tttctattcc agtgtgcaac aactcttctg ttcaagtggg atgccttact    4080
agagagaggc tcggagttaa cgttacttgg aagtccaggc tcgaggatat tcctgttgct    4140
tccctcccag atcttcacga tattgagagg gctcttgtgg gaaaggatct tcttggtagg    4200
ttcaccgatc ttattcagtc tggttccttc cagcttcacc ttgattctaa gaccttccca    4260
gctgagacta ttagattcct ccagggtgat cactttggaa cttctccaag aacctggttc    4320
ggatgctctg agggattcta ccaagtgctt acctctgagg cttctcaaga tggacttgga    4380
tgcgttaagt gcccagaggg atcatattct caggacgaga atgcattcc atgcccagtt     4440 ggtttctacc aagagcaggc tggatctctt gcttgtgttc cttgccctgt tggaaggact    4500
actatttccg ctggtgcttt ctctcagact cattgcgtta ctgattgcca gagaaacgag    4560
gctggattgc aatgcgatca gaacggacag tatagggctt ctcagaagga tagaggttcc    4620
ggaaaggctt tctgcgttga tggtgaaggt agaagattgc cttggtggga gactgaagct    4680
ccacttgagg attctcagtg cctcatgatg caaaagttcg agaaggtgcc agagtctaag    4740
gttatcttcg acgctaacgc tccagttgct gttagatcca aggtgccaga ttctgagttc    4800
ccagtgatgc aatgccttac tgattgcact gaggatgagg cttgctcatt cttcactgtg    4860
tctactaccg agccagagat ttcctgcgat ttctacgctt ggacctctga taacgttgct    4920
tgcatgacct ctgatcaaaa gagggatgct ctcggaaact ctaaggctac ctccttcgga    4980
tctcttaggt gccaagtgaa agttagatcc cacggacaag attctccagc tgtgtacctt    5040
aagaagggac aaggatctac tactaccctc cagaagagat tcgagccaac tggattccag    5100
aacatgcttt ccggactcta caacccaatt gtgttctctg cttccggtgc taaccttacc    5160
gatgctcacc ttttctgcct tttggcttgc gatagagatc tttgctgcga cggattcgtt    5220
cttactcaag ttcagggtgg agctattatt tgcggacttc tctcttctcc ttccgtgttg    5280
ctctgcaacg ttaaggattg gatggaccca tctgaggctt gggctaacgc tacttgccca    5340
ggtgttacct acgatcaaga gtctcaccaa gtgattctta ggctcggcga tcaagagttc    5400
attaagtccc ttaccccact tgagggaact caagacacct tcaccaactt ccagcaggtt    5460
tacctttgga aggattccga tatgggttct aggccagagt ctatgggatg caggaaggat    5520
actgttccaa gaccagcttc tccaactgag gctggactta ctaccgagct ttctccccca    5580
gttgatctca ccaggtgat cgttaacgga aaccagtctc tttcttccca aaagcactgg    5640
cttttcaagc accttttctc tgctcaacag gctaaccttt ggtgcctttc cagatgcgtt    5700
caagagcact ctttctgcca acttgctgag attaccgagt ctgcttccct ttacttcacc    5760 tgcaccctt atccagaggc tcaagtgtgc gacgatatta tggaatccaa cgctcaagga    5820
tgcaggctta ttcttcctca gatgccaaag gctctcttca ggaagaaggt tatcctcgag    5880
gacaaggtta agaacttcta caccaggctt ccattccaaa agctcatggg catttccatt    5940
aggaacaagg tgccaatgtc cgagaagtct atctccaacg gattcttcga gtgcgagaga    6000
agatgtgatg ctgatccatg ctgcactgga ttcggattcc ttaacgtgtc tcagcttaag    6060
```

```
ggtggagagg ttacctgcct taccottaac tccottggaa tccagatgtg ctcagaggaa    6120
aatggtggag cttggaggat tcttgattgc ggctccccag atattgaggt tcacacctac    6180
ccattcggat ggtatcagaa gccaatcgct caaaacaacg ctccatcttt ctgccctctt    6240
gtggtgcttc catctcttac tgagaaggtg tcccttgatt cttggcagtc tcttgctctt    6300
tcttctgttg tggtggaccc atctattagg catttcgatg tggctcatgt ttctactgct    6360
gccacctcta acttctctgc tgtgagggat ctttgcttgt ctgagtgctc tcaacatgag    6420
gcttgcctta ttactactct ccaaacccaa ccaggtgctg tgagatgcat gttctacgct    6480
gatactcagt cttgcaccca ttctcttcaa ggacagaact gtaggcttct tcttagggaa    6540
gaggctaccc atatctatag gaagccagga atttctcttc tttcctacga ggcttctgtt    6600
ccatctgtgc caatttctac ccacggaagg cttttgggaa gatctcaggc tattcaagtg    6660
ggaacctcat ggaagcaagt ggatcagttc cttggagttc catatgctgc tccaccactt    6720
gctgagagaa ggttccaagc tccagagcca cttaactgga ctggttcttg ggatgcttct    6780
aagccaagag cttcttgctg gcaaccagga actaggactt ctacttctcc tggtgtgtct    6840
gaggattgcc tttacctcaa cgtgttcatc ccacaaaacg ttgctccaaa cgcttctgtg    6900
cttgtgttct tccacaacac tatggatagg gaagagtctg aaggatggcc agctattgat    6960
ggttcttttcc tcgctgctgt gggaaaacctt attgtggtga ccgcttctta cagagttggt    7020
gtgttcggat tcctctcttc tggatctggt gaagtgtctg gaaactgggg acttcttgat    7080
caagttgctg ctcttacttg ggttcagacc cacattagag gattcggagg tgatccaaga    7140
agagtgtcct tggctgctga tagaggtgga gctgatgtgg cttctattca ccttcttacc    7200
gcaagggcta ctaactctca gctttttaga agggctgttc ttatgggagg atctgctctt    7260
tctccagctg ctgtgatttc tcatgagagg gctcaacaac aggctattgc ctcgctaag    7320
gaagtttcct gcccaatgtc atcttctcaa gaggtggtgt cttgccttag acaaaagcca    7380
gctaacgtgc ttaacgatgc tcagaccaag ttgttggctg tttctggacc attccattac    7440
tggggaccag ttatcgatgg acacttcttg agagagccac ctgctagagc tttgaagaga    7500
tcccttgggg tggaagtgga tcttcttatt ggctcctccc aggatgatgg acttatcaac    7560
agggctaagg ctgttaagca gttcgaggaa tctaggggaa ggacttcttc taagaccgct    7620
ttctaccagg ctcttcagaa ctcttcttggt ggagaggatt ctgatgctag agttgaggct    7680
gctgctactt ggtattactc ccttgagcac tccactgatg attacgcttc cttctctagg    7740
gctcttgaga cgctactag ggactacttc atcatctgcc caatcattga tatggcttcc    7800
gcttgggcta aaagagctag gggcaacgtt ttcatgtatc acgccccaga gaactatgga    7860
catggttctc ttgagttgct cgctgatgtt caattcgctc tcggacttcc attctatcca    7920
gcttacgagg gacaattctc ccttgaggaa aagtctctct ccctcaagat catgcaatac    7980
ttctctcact tcatcagatc cggcaaccca aactatccat acgagttctc taggaaggtt    8040
ccaactttcg ctactccttg gccagatttc gttccaagag ctggcggaga gaactacaaa    8100
gagttctccg agcttcttcc aaacaggcag ggacttaaga aggctgattg ctccttctgg    8160
tccaagtaca tttcttccct caagacctct gctgatggtg ctaagggtgg acaatctgct    8220
gagtctgagg aagaggaact tactgctgga tctggactta gagaggatct tctctccctt    8280
caagagccag gatctaagac ctactccaag ggaggacatc accatcacca tcactaatct    8340
agagagctc                                                            8349
```

<210> SEQ ID NO 2
<211> LENGTH: 8427
<212> TYPE: DNA
<213> ORGANISM: Human

<400> SEQUENCE: 2

```
atggccctgg tcctggagat cttcaccctg ctggcctcca tctgctgggt gtcggccaat      60
atcttcgagt accaggtgga tgcccagccc cttcgtccct gtgagctgca gagggaaacg     120
gcctttctga agcaagcaga ctacgtgccc cagtgtgcag aggatggcag cttccagact     180
gtccagtgcc agaacgacgg ccgctcctgc tggtgtgtgg gtgccaacgg cagtgaagtg     240
ctgggcagca gcagccagg acggcctgtg gcttgtctgt cattttgtca gctacagaaa     300
cagcagatct tactgagtgg ctacattaac agcacagaca cctcctacct ccctcagtgt     360
caggattcag gggactacgc gcctgttcag tgtgatgtgc agcaggtcca gtgctggtgt     420
gtggacgcag aggggatgga ggtgtatggg acccgccagc tggggaggcc aaagcgatgt     480
ccaaggagct gtgaaataag aaatcgtcgt cttctccacg gggtgggaga taagtcacca     540
ccccagtgtt ctgcggaggg agagtttatg cctgtccagt gcaaatttgt caacaccaca     600
gacatgatga tttttgatct ggtccacagc tacaacaggt ttccagatgc atttgtgacc     660
ttcagttcct tccagaggag gttccctgag gtatctgggt attgccactg tgctgacagc     720
caagggcggg aactggctga cacaggtttg gagttgttac tggatgaaat ttatgacacc     780
attttttgctg gcctggacct tccttccacc ttcactgaaa ccaccctgta ccggatactg     840
cagagacggt tcctcgcagt tcaatcagtc atctctggca gattccgatg ccccacaaaa     900
tgtgaagtgg agcggtttac agcaaccagc tttggtcacc ctatgttcc aagctgccgc     960
cgaaatggcg actatcaggc ggtgcagtgc cagacggaag ggcctgctg gtgtgtggac    1020
gcccagggga aggaaatgca tggaacccgg cagcaagggg agccgccatc ttgtgctgaa    1080
ggccaatctt gtgcctccga aaggcagcag gccttgtcca gactctactt tgggacctca    1140
ggctacttca gccagcacga cctgttctct tccccagaga aaagatgggc ctctccaaga    1200
gtagccagat ttgccacatc ctgcccaccc acgatcaagg agctctttgt ggactctggg    1260
cttctccgcc caatggtgga gggacagagc caacagttt ctgtctcaga aaatcttctc    1320
aaagaagcca tccgagcaat ttttcccctcc cgagggctgg ctcgtcttgc ccttcagttt    1380
accaccaacc caaagagact ccagcaaaac cttttttggag ggaaatttttt ggtgaatgtt    1440
ggccagttta acttgtctgg agcccttggc acaagaggca catttaactt cagtcaattt    1500
ttccagcaac ttggtcttgc aagcttcttg aatggaggga caagaagaa tttggccaag    1560
ccactctctg tgggattaga ttcaaattct ccacaggaa ccctgaagc tgctaagaag    1620
gatggtacta tgaataagcc aactgtgggc agctttggct ttgaaattaa cctacaagag    1680
aaccaaaatg ccctcaaatt ccttgcttct ctcctggagc ttccagaatt ccttctcttc    1740
ttgcaacatg ctatctctgt gccagaagat gtggcaagag atttaggtga tgtgatggaa    1800
acggtactca gctcccagac ctgtgagcag acacctgaaa ggctatttgt cccatcatgc    1860
acgacagaag gaagctatga ggatgtccaa tgcttttccg gagagtgctg gtgtgtgaat    1920
tcctggggca aagagcttcc aggctcaaga gtcgaggtg acagccaag gtgccccaca    1980
gactgtgaaa agcaaagggc tcgcatgcaa agcctcatgg gcagccagcc tgctggctcc    2040
accttgtttg tccctgcttg tactagtgag ggacatttcc tgcctgtcca gtgcttcaac    2100
tcagagtgct actgtgttga tgctgagggt caggccattc ctggaactcg aagtgcaata    2160
```

```
gggaagccca agaaatgccc cacgccctgt caattacagk ctgagcaagc tttcctcagg    2220
acggtgcagg ccctgctctc taactccagc atgctaccca ccctttccga cacctacatc    2280
ccacagtgca gcaccgatgg cagtggaga caagtgcaat gcaatgggcc tccygagcag     2340
gtcttcgagt tgtaccaacg atgggaggct cagaacaagg gccaggatct gacgcctgcc    2400
aagctgctag tgaagatcat gagctacaga gaagcagctt ccggaaactt cagtctcttt    2460
attcaaagtc tgtatgaggc tggccagcaa gatgtcttcc cggtgctgtc acaataccct    2520
tctctgcaag atgtcccact agcagcactg gaagggaaac ggccccagcc cagggagaat    2580
atcctcctgg agccctacct cttctggcag atcttaaatg ccaactcag ccaatacccg      2640
gggtcctact cagacttcag cactcctttg gcacattttg atcttcggaa ctgctggtgt    2700
gtggatgagg ctggccaaga actggaagga atgcggtctg agccaagcaa gctcccaaca    2760
tgtcctggct cctgtgagga agcaaagctc cgtgtactgc agttcattag ggaaacggaa    2820
gagattgttt cagcttccaa cagttctcgg ttccctctgg gggagagttt cctggtggcc    2880
aagggaatcc ggctgaggaa tgaggacctc ggccttcctc cgctcttccc gccccgggag    2940
gctttcgcgg agcagtttct cgtgggagt gattacgcca ttcgcctggc ggctcagtct     3000
accttaagct tctatcagag acgccgcttt tccccggacg actcggctgg agcatccgcc    3060
cttctgcggt cgggccccta crtgccacag tgtgatgcgt ttggaagttg ggagcctgtg    3120
cagtgccacg ctgggactgg gcactgctgg tgtgtagatg agaaaggagg gttcatccct    3180
ggctcactga ctgcccgctc tctgcagatt ccacagtgcc cgacaacctg cgagaaatct    3240
cgaaccagtg ggctgctttc cagttggaaa caggctagat cccaagaaaa cccatctcca    3300
aaagacctgt tcgtcccagc ctgcctagaa acaggagagt atgccaggct gcaggcatcg    3360
ggggctggca cctggtgtgt ggaccctgca tcaggagaag agttgcggcc tggctcgagc    3420
agcagtgccc agtgcccaag cctctgcaat gtgctcaaga gtggagtcct ctctaggaga    3480
gtcagcccag gctatgtccc agcctgcagg gcagaggatg ggggcttttc cccagtgcaa    3540
tgtgaccagg cccagggcag ctgctggtgt gtcatggaca gcggagaaga ggtgcctggg    3600
acgcgcgtga ccgggggcca gcccgcctgt gagagcccgc ggtgtccgct gccattcaac    3660
gcgtcggagg tggttggtgg aacaatcctg tgtgagacaa tctcgggccc cacaggctct    3720
gccatgcagc agtgccaatt gctgtgccgc caaggctcct ggagcgtgtt tccaccaggg    3780
ccattgatat gtagcctgga gagcggacgc tgggagtcac agctgcctca gccccgggcc    3840
tgccaacggc cccagctgtg gcagaccatc cagacccaag gcactttca gctccagctc    3900
ccgccgggca agatgtgcag tgctgactac gcgggtttgc tgcagacttt ccaggttttc    3960
atattggatg agctgacagc ccgcggcttc tgccagatcc aggtgaagac ttttggcacc    4020
ctggtttcca ttcctgtctg caacaactcc tctgtgcagg tgggttgtct gaccagggag    4080
cgtttaggag tgaatgttac atggaaatca cggcttgagg acatcccagt ggcttctctt    4140
cctgacttac atgacattga gagagccttg gtgggcaagg atctccttgg gcgcttcaca    4200
gatctgatcc agagtggctc attccagctt catctggact ccaagacgtt cccagcggaa    4260
accatccgct tcctccaagg ggaccacttt ggcacctctc caggacatg gtttgggtgc    4320
tcggaaggat tctaccaagt cttgacaagt gaggccagtc aggacggact gggatgcgtt    4380
aagtgtcctg aaggaagcta ttcccaagat gaggaatgca ttccttgtcc tgttggattc    4440
taccaagaac aggcagggag cttggcctgt gtcccatgtc ctgtgggcag aacgaccatt    4500
tctgcyggag cttttcagcca gactcactgt gtcactgact gtcagaggaa cgaagcaggc    4560
```

```
ctgcaatgtg accagaatgg ccagtatcga gccagccaga aggacagggg cagtgggaag    4620
gccttctgtg tggacggcga ggggcggagg ctgccatggt gggaaacaga ggcccctctt    4680
gaggactcac agtgtttgat gatgcagaag tttgagaagg ttccagaatc aaaggtgatc    4740
ttcgacgcca atgctcctgt ggctgtcaga tccaaagttc ctgattctga gttccccgtg    4800
atgcagtgct tgacagattg cacagaggac gaggcctgca gcttcttcac cgtgtccacg    4860
acggagccag agatttcctg tgatttctat gcttggacaa gtgacaatgt tgcctgcatg    4920
acttctgacc agaaacgaga tgcactgggg aactcaaagg ccaccagctt ggaagtcttt    4980
cgctgccagg tgaaagtgag gagccatggt caagattctc cagctgtgta tttgaaaaag    5040
ggccaaggat ccaccacaac acttcagaaa cgctttgaac ccactggttt ccaaaacatg    5100
ctttctggat tgtacaaccc cattgtgttc tcagcctcag gagccaatct aaccgatgct    5160
cacctcttct gtcttcttgc atgcgaccgt gatctgtgtt gcgatggctt cgtcctcaca    5220
caggttcaag gaggtgccat catctgtggg ttgctgagct cacccagtgt cctgctttgt    5280
aatgtcaaag actggatgga tccctctgaa gcctgggcta atgctacatg tcctggtgtg    5340
acatatgacc aggagagcca ccaggtgata ttgcgtcttg gagaccagga gttcatcaag    5400
agtctgacac ccttagaagg aactcaagac acctttacca attttcagca ggtttatctc    5460
tggaaagatt ctgacatggg gtctcggcct gagtctatgg gatgtagaaa aracacagtg    5520
ccaaggccag catctccaac agaagcaggt ttgacaacag aacttttctc ccctgtggac    5580
ctcaaccagg tcattgtcaa tggaaatcaa tcactatcca gccagaagca ctggcttttc    5640
aagcacctgt tttcagccca gcaggcaaac ctatggtgcc tttctcgttg tgtgcaggag    5700 cactcttttct gtcagctcgc agagataaca gagagtgcat ccttgtactt cacctgcacc    5760
ctctacccag aggcacaggt gtgtgatgac atcatggagt ccaatgccca gggctgcaga    5820
ctgatcctgc ctcagatgcc aaaggccctg ttccggaaga agttatact ggaagataaa    5880 gtgaagaact tttacactcg cctgccgttc caaaaactga tggggatatc cattagaaat    5940
aaagtgccca tgtctgaaaa atctatttct aatgggttct ttgaatgtga acgacggtgc    6000
gatgcggacc catgctgcac tggctttgga tttctaaatg tttcccagtt aaaaggagga    6060
gaggtgacat gtctcactct gaacagcttg ggaattcaga tgtgcagtga ggagaatgga    6120
ggagcctggc gcattttgga ctgtggctct cctgacattg aagtccacac ctatccttc    6180 ggatggtacc agaagcccat tgctcaaaat aatgctccca gttttgcc tttggttgtt    6240 ctgccttccc tcacagagaa agtgtctctg gactcgtggc agtccctggc cctctcttca    6300
gtggttgttg atccatccat taggcacttt gatgttgccc atgtcagcac tgctgccacc    6360
agcaatttct ctgctgtccg agacctctgt ttgtcggaat gttccaaca tgaggcctgt    6420 ctcatcacca ctctgcaaac ccaacctggg gctgtgagat gtatgttcta tgctgatact    6480
caaagctgca cacatagtct gcagggtcag aactgccgac ttctgcttcg tgaagaggcc    6540
acccacatct accggaagcc aggaatctct ctgctcagct atgaggcatc tgtaccttct    6600
gtgcccattt ccacccatgg ccggctgctg gcaggtccc aggccatcca ggtgggtacc    6660
tcatggaagc aagtggacca gttccttgga gttccatatg ctgccccgcc cctggcagag    6720
aggcgcttcc aggcaccaga gcccttgaac tggacaggct cctgggatgc cagcaagcca    6780
agggccagct gctggcagcc aggcaccaga acatccacgt ctcctggagt cagtgaagat    6840
tgtttgtatc tcaatgtgtt catccctcag aatgtggccc ctaacgcgtc tgtgctggtg    6900
```

```
ttcttccaca acaccatgga cagggaggag agtgaaggat ggccggctat c

<223> OTHER INFORMATION: regions of the soy optimized thyroglobulin
      protein

<400> SEQUENCE: 4

| | | | |
|---|---|---|---|
| gcttgccttt ctttctgcca gcttcagaag cagcagattc ttctctccgg ttacatcaac | | | 60 |
| tctaccgaca cctcttatct tccacagtgc caggattctg gtgattacgc tccagttcaa | | | 120 |
| tgcgacgttc aacaagttca atgctggtgc gttgatgctg agggaatgga agtttacgga | | | 180 |
| accagacaac ttggaaggcc aaagagatgc ccaagatcct gcgagattag gaacagaagg | | | 240 |
| cttcttcacg gagttggaga taagtctcca ccacaa | | | 276 |

<210> SEQ ID NO 5
<211> LENGTH: 276
<212> TYPE: DNA
<213> ORGANISM: Artificial Sequence
<220> FEATURE:
<223> OTHER INFORMATION: regions of the soy optimized thyroglobulin
      protein

<400> SEQUENCE: 5

| | | | |
|---|---|---|---|
| tgctctgctg aaggcgagtt catgcctgtt cagtgcaagt tcgtgaacac caccgacatg | | | 60 |
| atgattttcg atctcgtgca ctcctataac agattcccag atgccttcgt gactttctct | | | 120 |
| tccttccaga gaagattccc agaggtttca ggatattgcc actgcgctga ttctcaaggt | | | 180 |
| agagagcttc tgagactgg acttgagctt ctcctcgatg agatctacga taccattttc | | | 240 |
| gctggacttg atcttccatc taccttcacc gagact | | | 276 |

<210> SEQ ID NO 6
<211> LENGTH: 276
<212> TYPE: DNA
<213> ORGANISM: Artificial Sequence
<220> FEATURE:
<223> OTHER INFORMATION: regions of the soy optimized thyroglobulin
      protein

<400> SEQUENCE: 6

| | | | |
|---|---|---|---|
| acccttaca ggattctcca aagaagattc ctcgctgttc agtctgttat ttccggaaga | | | 60 |
| ttcaggtgcc caactaagtg cgaggttgag aggttcactg ctacttcatt cggacatcca | | | 120 |
| tacgttccat cttgcagaag aaacggcgat taccaggctg ttcaatgcca aactgaggga | | | 180 |
| ccatgttggt gtgttgatgc ccagggaaaa gaaatgcatg gaaccaggca acaaggtgaa | | | 240 |
| ccaccatctt gcgctgaagg acaatcttgc gcttct | | | 276 |

<210> SEQ ID NO 7
<211> LENGTH: 276
<212> TYPE: DNA
<213> ORGANISM: Artificial Sequence
<220> FEATURE:
<223> OTHER INFORMATION: regions of the soy optimized thyroglobulin
      protein

<400> SEQUENCE: 7

| | | | |
|---|---|---|---|
| gagaggcaac aagctctttc taggctctac ttcggaacct ctggatactt ctcccagcac | | | 60 |
| gatcttttct cttcaccaga gaagagatgg cttctccaa gagttgctag attcgctact | | | 120 |
| tcttgcccac caaccatcaa agagcttttc gttgattccg gacttcttag gccaatggtt | | | 180 |
| gagggacaat ctcagcagtt ctctgtgtct gagaaccttc tcaaagaggc tattagggct | | | 240 |
| attttcccat ctaggggact tgctaggctt gctctt | | | 276 |

```
<210> SEQ ID NO 8
<211> LENGTH: 276
<212> TYPE: DNA
<213> ORGANISM: Artificial Sequence
<220> FEATURE:
<223> OTHER INFORMATION: regions of the soy optimized thyroglobulin
      protein

<400> SEQUENCE: 8
caattcacca ccaacccaaa gaggcttcag caaaaccttt tcggaggaaa gttcctcgtt      60
aatgtgggac agttcaacct ttctggtgct cttggaacta ggggaacctt caacttctct    120
cagttcttcc agcaacttgg acttgcttct ttccttaacg gtggcaggca agaggatctt    180
gcaaagccac tttctgtggg acttgattct aactcttcca ctggaactcc agaggctgct    240
aagaaagatg gcaccatgaa caagccaact gtggga                              276

<210> SEQ ID NO 9
<211> LENGTH: 276
<212> TYPE: DNA
<213> ORGANISM: Artificial Sequence
<220> FEATURE:
<223> OTHER INFORMATION: regions of the soy optimized thyroglobulin
      protein

<400> SEQUENCE: 9
tctttcggct tcgagatcaa ccttcaagag aaccagaacg ctcttaagtt ccttgcttcc      60
cttcttgagc ttccagagtt ccttcttttc ctccagcacg ctatttctgt tccagaggat    120
gtggctagag atcttggtga tgtgatggaa accgtgcttt cttctcaaac ttgcgagcaa    180
actccagaga gactttttcgt tccttcttgc actactgagg atcttacga ggatgttcag    240 tgcttctctg gtgagtgttg gtgcgttaac tcttgg                              276

<210> SEQ ID NO 10
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 10
ggaaaagagc ttccaggatc aagagttaga ggtggacaac ctagatgccc aactgattgc      60
gagaagcaaa gggctaggat gcaatctctt atgggatctc agccagctgg atctactctt    120
ttcgtgccag cttgcacttc tgaaggacac ttccttccag tgcaatgctt caactctgag    180
tgctattgcg tggatgctga aggtcaagct attccaggaa ccagatccgc tattggcaag    240
ccaaagaagt gcccaactcc ttgccaactt caatctgag                           279

<210> SEQ ID NO 11
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 11
caggctttcc ttaggactgt tcaggctctt cttttccaact cttccatgct tccaaccctt     60
tccgatacct acattccaca gtgctctact gatggacagt ggagacaagt tcagtgtaac    120
ggaccaccag agcaagtttt cgagctttac cagagatggg aggctcaaaa caagggacaa    180
```

```
gatctcactc cagctaagtt gctcgtgaag atcatgtctt acagagaggc tgcttctgga      240
aacttcagcc tcttcatcca gtcactttac gaggctgga                            279
```

<210> SEQ ID NO 12
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 12

```
cagcaagatg ttttcccagt gctttctcag tacccatctc ttcaggatgt tccacttgct      60
gctcttgagg gaaaaagacc acagccaaga gagaacattc ttctcgagcc ttacctcttc     120
tggcagattc ttaacggaca gctttcacag tatcctggtt cctactctga tttctctacc     180
ccactcgctc atttcgatct tagaaactgc tggtgtgtgg atgaagctgg acaagagctt     240
gagggaatga gatctgagcc atctaagttg ccaacttgc                            279
```

<210> SEQ ID NO 13
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 13

```
ccaggatctt gcgaggaagc taagttgaga gtgctccagt tcattaggga aaccgaggaa      60
attgtgtctg cttctaactc ctctaggttc ccacttggag agtctttcct tgtggctaag     120
ggaattaggc ttaggaacga ggatcttgga cttccaccac ttttcccacc aagagaggct     180
ttcgctgaac aattcctcag gggttccgat tatgctatta ggcttgctgc tcagtctacc     240 ttgtcttttct accagagaag aaggttctct ccagacgat                           279
```

<210> SEQ ID NO 14
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 14

```
tctgctggtg cttctgctct tcttagatcc ggaccttaca tgccacaatg cgacgctttt      60
ggatcttggg agccagttca atgtcatgct ggaactggac actgttggtg cgtggatgag     120
aagggcggtt tcattccagg atctcttacc gctagatccc ttcagattcc acaatgccct     180
actacttgcg agaagtctag gacctctgga cttctttctt cttggaagca ggctaggtca     240
caagaaaacc catccccaaa ggatcttttc gttccagca                            279
```

<210> SEQ ID NO 15
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 15

```
tgccttgaga ctggtgagta tgctagactt caggcttctg gtgctggaac atggtgtgtt      60
```

```
gacccagctt ctggtgaaga acttaggcca ggatcttctt cttctgctca gtgcccatct    120
ttgtgcaacg tgcttaagtc tggtgttctt tccagaagag tgtctccagg atatgttcca    180
gcttgcagag ctgaggatgg tggattctct ccagttcagt gtgatcaagc tcaaggatct    240
tgttggtgcg tgatggattc tggtgaagag gttccagga                           279

<210> SEQ ID NO 16
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 16
actagagtta ctggcggaca accagcttgt gaatctccaa gatgcccact tccattcaac     60
gcttcagagg ttgtgggagg aactattctc tgcgagacta tttctggacc aaccggttct    120
gctatgcaac aatgccagct tttgtgcaga caaggatctt ggtctgtttt ccaccagga     180 ccacttattt gctcccttga gtctggaaga tgggagtctc aacttccaca acctagagct    240
tgccaaagac cacaactctg gcaaactatt cagacccag                           279

<210> SEQ ID NO 17
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 17
ggacatttcc aacttcaact cccacctgga aagatgtgct ctgctgatta cgctgatctt     60
ctccagactt ccaggtgtt catcctcgat gagcttactg ctagaggatt ctgccagatc    120
caggttaaga ctttcggaac cctcgtttct attccagtgt gcaacaactc ttctgttcaa    180
gtgggatgcc ttactagaga gaggctcgga gttaacgtta cttggaagtc caggctcgag    240
gatattcctg ttgcttccct cccagatctt cacgatatt                           279

<210> SEQ ID NO 18
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 18
gagagggctc ttgtgggaaa ggatcttctt ggtaggttca ccgatcttat tcagtctggt     60
tccttccagc ttcaccttga ttctaagacc ttcccagctg agactattag attcctccag    120
ggtgatcact ttgaacttc tccaagaacc tggttcggat gctctgaggg attctaccaa     180
gtgcttacct ctgaggcttc tcaagatgga cttggatgcg ttaagtgccc agagggatca    240
tattctcagg acgaggaatg cattccatgc ccagttggt                           279

<210> SEQ ID NO 19
<211> LENGTH: 279
<212> TYPE: DNA
<213> ORGANISM: Artificial Sequence
<220> FEATURE:
<223> OTHER INFORMATION: regions of the soy optimized thyroglobulin
``` protein

<400> SEQUENCE: 19

| ttctaccaag agcaggctgg atctcttgct tgtgttcctt gccctgttgg aaggactact | 60 |
| atttccgctg gtgctttctc tcagactcat tgcgttactg attgccgagag aaacgaggct | 120 |

<400> SEQUENCE: 19
ttctaccaag agcaggctgg atctcttgct tgtgttcctt gccctgttgg aaggactact    60
atttccgctg gtgctttctc tcagactcat tgcgttactg attgccgagag aaacgaggct   120 ggattgcaat gcgatcagaa cggacagtat agggcttctc agaaggatag aggttccgga   180
aaggctttct gcgttgatgg tgaaggtaga agattgcctt ggtgggagac tgaagctcca   240
cttgaggatt ctcagtgcct catgatgcaa aagttcgag                           279

<210> SEQ ID NO 20
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 20
aaggtgccag agtctaaggt tatcttcgac gctaacgctc cagttgctgt tagatccaag    60
gtgccagatt ctgagttccc agtgatgcaa tgccttactg attgcactga ggatgaggct   120
tgctcattct tcactgtgtc tactaccgag ccagagattt cctgcgattt ctacgcttgg   180
acctctgata cgttgcttg catgacctct gatcaaaaga gggatgctct cggaaactct   240
aaggctacct ccttcggatc tcttaggtgc aagtgaaa                           279

<210> SEQ ID NO 21
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 21
gttagatccc acggacaaga ttctccagct gtgtacctta agaagggaca aggatctact 60
actaccctcc agaagagatt cgagccaact ggattccaga acatgctttc cggactctac 120
aacccaattg tgttctctgc ttccggtgct aaccttaccg atgctcacct tttctgcctt 180
ttggcttgcg atagagatct ttgctgcgac ggattcgttc ttactcaagt tcagggtgga 240
gctattattt gcggacttct ctcttctcct tccgtgttg 279

<210> SEQ ID NO 22
<211> LENGTH: 279
<212> TYPE: DNA
<213> ORGANISM: Artificial Sequence
<220> FEATURE:
<223> OTHER INFORMATION: regions of the soy optimized thyroglobulin
protein

<400> SEQUENCE: 22
ctctgcaacg ttaaggattg gatggaccca tctgaggctt gggctaacgc tacttgccca 60
ggtgttacct acgatcaaga gtctcaccaa gtgattctta ggctcggcga tcaagagttc 120
attaagtccc ttaccccact tgagggaact caagacacct tcaccaactt ccagcaggtt 180
tacctttgga aggattccga tatgggttct aggccagagt ctatgggatg caggaaggat 240
actgttccaa gaccagcttc tccaactgag gctggactt 279

<210> SEQ ID NO 23

```
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 23
actaccgagc ttttctcccc agttgatctc aaccaggtga tcgttaacgg aaaccagtct      60
ctttcttccc aaaagcactg gcttttcaag cacctttcct ctgctcaaca ggctaacctt     120
tggtgccttt ccagatgcgt tcaagagcac tctttctgcc aacttgctga gattaccgag     180
tctgcttccc tttacttcac ctgcacccct tatccagagg ctcaagtgtg cgacgatatt     240
atggaatcca acgctcaagg atgcaggctt attcttcct                             279

<210> SEQ ID NO 24
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 24
cagatgccaa aggctctctt caggaagaag gttatcctcg aggacaaggt taagaacttc      60
tacaccaggc ttccattcca aaagctcatg ggcatttcca ttaggaacaa ggtgccaatg     120
tccgagaagt ctatctccaa cggattcttc gagtgcgaga aagatgtga tgctgatcca     180 tgctgcactg gattcggatt ccttaacgtg tctcagctta aggtggaga ggttacctgc      240 cttacccta actcccttgg aatccagatg tgctcagag                             279

<210> SEQ ID NO 25
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 25
gaaaatggtg gagcttggag gattcttgat tgcggctccc cagatattga ggttcacacc      60
tacccattcg gatggtatca gaagccaatc gctcaaaaca acgctccatc tttctgccct     120
cttgtggtgc ttccatctct tactgagaag gtgtcccttg attcttggca gtctcttgct     180 cttttcttctg ttgtggtgga cccatctatt aggcatttcg atgtggctca tgtttctact     240
gctgccacct ctaacttctc tgctgtgagg gatctttgc                             279

<210> SEQ ID NO 26
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 26
ttgtctgagt gctctcaaca tgaggcttgc cttattacta ctctccaaac ccaaccaggt      60
gctgtgagat gcatgttcta cgctgatact cagtcttgca cccattctct tcaaggacag     120
aactgtaggc ttcttcttag ggaagaggct acccatatct ataggaagcc aggaatttct     180
cttctttcct acgaggcttc tgttccatct gtgccaattt ctacccacgg aagcttttg     240
```

```
ggaagatctc aggctattca agtgggaacc tcatggaag                              279
```

<210> SEQ ID NO 27
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 27

```
caagtggatc agttccttgg agttccatat gctgctccac cacttgctga gagaaggttc    60
caagctccag agccacttaa ctggactggt tcttgggatg cttctaagcc aagagcttct   120
tgctggcaac caggaactag gacttctact tctcctggtg tgtctgagga ttgcctttac   180
ctcaacgtgt tcatcccaca aaacgttgct ccaaacgctt ctgtgcttgt gttcttccac   240
aacactatgg atagggaaga gtctgaagga tggccagct                           279
```

<210> SEQ ID NO 28
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 28

```
attgatggtt ctttcctcgc tgctgtggga aaccttattg tggtgaccgc ttcttacaga    60
gttggtgtgt tcggattcct ctcttctgga tctggtgaag tgtctggaaa ctggggactt   120
cttgatcaag ttgctgctct tacttgggtt cagacccaca ttagaggatt cggaggtgat   180
ccaagaagag tgtccttggc tgctgataga ggtggagctg atgtggcttc tattcacctt   240
cttaccgcaa gggctactaa ctctcagctt tttagaagg                            279
```

<210> SEQ ID NO 29
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 29

```
gctgttctta tgggaggatc tgctctttct ccagctgctg tgatttctca tgagagggct    60
caacaacagg ctattgctct cgctaaggaa gtttcctgcc aatgtcatc ttctcaagag    120
gtggtgtctt gccttagaca aaagccagct aacgtgctta acgatgctca gaccaagttg   180
ttggctgttt ctgaccatt ccattactgg ggaccagtta tcgatggaca cttcttgaga   240
gagccacctg ctagagcttt gaagagatcc ctttgggtg                            279
```

<210> SEQ ID NO 30
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 30

```
gaagtggatc ttcttattgg ctcctcccag gatgatggac ttatcaacag ggctaaggct    60
```

```
gttaagcagt tcgaggaatc taggggaagg acttcttcta agaccgcttt ctaccaggct    120
cttcagaact ctcttggtgg agaggattct gatgctagag ttgaggctgc tgctacttgg    180
tattactccc ttgagcactc cactgatgat tacgcttcct tctctagggc tcttgagaac    240
gctactaggg actacttcat catctgccca atcattgat                           279

<210> SEQ ID NO 31
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 31
atggcttccg cttgggctaa aagagctagg ggcaacgttt tcatgtatca cgccccagag     60
aactatggac atggttctct tgagttgctc gctgatgttc aattcgctct cggacttcca    120
ttctatccag cttacgaggg acaattctcc cttgaggaaa agtctctctc cctcaagatc    180
atgcaatact tctctcactt catcagatcc ggcaacccaa actatccata cgagttctct    240
aggaaggttc aactttcgc tactccttgg ccagatttc                            279

<210> SEQ ID NO 32
<211> LENGTH: 279
<212> TYPE: DNA
<213> ORGANISM: Artificial Sequence
<220> FEATURE:
<223> OTHER INFORMATION: regions of the soy optimized thyroglobulin
      protein

<400> SEQUENCE: 32
gttccaagag ctggcggaga gaactacaaa gagttctccg agcttcttcc aaacaggcag     60
ggacttaaga aggctgattg ctccttctgg tccaagtaca tttcttccct caagacctct    120
gctgatggtg ctaagggtgg acaatctgct gagtctgagg aagaggaact tactgctgga    180
tctggactta gagaggatct tctctcccctt caagagccag gatctaagac ctactccaag    240
ggaggacatc accatcacca tcactaatct agagagctc                           279

<210> SEQ ID NO 33
<211> LENGTH: 23
<212> TYPE: DNA
<213> ORGANISM: Artificial Sequence
<220> FEATURE:
<223> OTHER INFORMATION: Artificial Sequence

<400> SEQUENCE: 33
gctcaaccac ttagaccatg cga                                             23

<210> SEQ ID NO 34
<211> LENGTH: 22
<212> TYPE: DNA
<213> ORGANISM: Artificial Sequence
<220> FEATURE:
<223> OTHER INFORMATION: Artificial Sequence

<400> SEQUENCE: 34
tcagcgcagt ggcaatatcc tg                                              22

<210> SEQ ID NO 35
<211> LENGTH: 20
<212> TYPE: DNA
<213> ORGANISM: Artificial Sequence
```

```
<220> FEATURE:
<223> OTHER INFORMATION: Artificial Sequence

<400> SEQUENCE: 35
gcttccacac atgggagcag                                                   20

<210> SEQ ID NO 36
<211> LENGTH: 20
<212> TYPE: DNA
<213> ORGANISM: Artificial Sequence
<220> FEATURE:
<223> OTHER INFORMATION: Artificial Sequence

<400> SEQUENCE: 36
cctctgtggt ctccaagcag                                                   20

<210> SEQ ID NO 37
<211> LENGTH: 4
<212> TYPE: PRT
<213> ORGANISM: human

<400> SEQUENCE: 37

Lys Asp Glu Leu
1
```

UNITED STATES PATENT AND TRADEMARK OFFICE
CERTIFICATE OF CORRECTION

PATENT NO. : 9,551,005 B2
APPLICATION NO. : 13/254704
DATED : January 24, 2017
INVENTOR(S) : Kenneth John Piller and Kenneth Lee Bost It is certified that error appears in the above-identified patent and that said Letters Patent is hereby corrected as shown below:

In the Specification

Please add the new section heading and paragraph shown below Column 1, Line 15 before the section entitled "BACKGROUND OF THE INVENTION":
STATEMENT REGARDING FEDERALLY SPONSORED RESEARCH
This invention was made with government support under contract nos. R43 CA150324 and R44 CA150324 awarded by the National Institutes of Health. The government has certain rights in the invention.

Signed and Sealed this
Eighteenth Day of December, 2018

Andrei Iancu
*Director of the United States Patent and Trademark Office*